(12) United States Patent
Baxter, III et al.

(10) Patent No.: US 10,945,782 B2
(45) Date of Patent: *Mar. 16, 2021

(54) BIPOLAR ELECTROSURGICAL HAND SHEARS

(71) Applicant: ETHICON LLC, Guaynabo, PR (US)

(72) Inventors: Chester O. Baxter, III, Loveland, OH (US); David C. Yates, West Chester, OH (US); Katherine J. Schmid, Loveland, OH (US); Taylor W. Aronhalt, Loveland, OH (US); Jeffrey S. Swayze, West Chester, OH (US); Jeffrey D. Messerly, Cincinnati, OH (US); Michael S. Cropper, Edgewood, KY (US); Jerome R. Morgan, Cincinnati, OH (US); Richard W. Timm, Cincinnati, OH (US); Frederick E. Shelton, IV, Hillsboro, OH (US)

(73) Assignee: Ethicon LLC, Guaynabo, PR (US)

( * ) Notice: Subject to any disclaimer, the term of this patent is extended or adjusted under 35 U.S.C. 154(b) by 690 days.

This patent is subject to a terminal disclaimer.

(21) Appl. No.: 15/437,638

(22) Filed: Feb. 21, 2017

(65) Prior Publication Data
US 2017/0224409 A1 Aug. 10, 2017

Related U.S. Application Data

(63) Continuation of application No. 13/752,588, filed on Jan. 29, 2013, now Pat. No. 9,610,114.

(51) Int. Cl.
*A61B 18/14* (2006.01)
*A61B 18/00* (2006.01)
(Continued)

(52) U.S. Cl.
CPC ...... *A61B 18/1442* (2013.01); *A61B 17/3201* (2013.01); *A61B 2017/2825* (2013.01);
(Continued)

(58) Field of Classification Search
CPC ............ A61B 18/1442; A61B 17/3201; A61B 2018/1457
See application file for complete search history.

(56) References Cited

U.S. PATENT DOCUMENTS 5,388,270 A 2/1995 Hewitt
5,893,878 A 4/1999 Pierce
(Continued)

FOREIGN PATENT DOCUMENTS

CN 102006832 A 4/2011
CN 102056553 A 5/2011
(Continued)

OTHER PUBLICATIONS

International Search Report and Written Opinion dated Aug. 29, 2014 for Application No. PCT/US2014/011647, 18 pgs.
(Continued)

*Primary Examiner* — Linda C Dvorak
*Assistant Examiner* — Annabeth E Rodriguez
(74) *Attorney, Agent, or Firm* — Frost Brown Todd LLC

(57) ABSTRACT

An apparatus comprises a first jaw, a second jaw, a first handle, and a second handle. The second jaw is pivotally coupled with the first jaw. The first jaw and the second jaw are configured to grasp tissue. The jaws provide offset electrode surfaces that are operable to deliver bipolar RF energy to tissue grasped between the jaws. The apparatus is further operable to sever tissue. A lockout feature selectively prevents tissue severing, based on an energization state of the jaws.

19 Claims, 42 Drawing Sheets

(51) Int. Cl.
*A61B 17/3201* (2006.01)
*A61B 17/28* (2006.01)

(52) U.S. Cl.
CPC ............... *A61B 2018/0016* (2013.01); *A61B 2018/00071* (2013.01); *A61B 2018/00678* (2013.01); *A61B 2018/00916* (2013.01); *A61B 2018/00958* (2013.01); *A61B 2018/1455* (2013.01); *A61B 2018/1457* (2013.01)

(56) References Cited

U.S. PATENT DOCUMENTS

| | | | |
|---|---|---|---|
| 6,030,384 A * | 2/2000 | Nezhat | A61B 18/1442 606/48 |
| 6,500,176 B1 | 12/2002 | Truckai et al. | |
| 6,514,252 B2 | 2/2003 | Nezhat et al. | |
| 6,775,575 B2 | 8/2004 | Bommannan et al. | |
| 6,783,524 B2 | 8/2004 | Anderson et al. | |
| 7,112,201 B2 | 9/2006 | Truckai et al. | |
| 7,125,409 B2 | 10/2006 | Truckai et al. | |
| 7,156,846 B2 | 1/2007 | Dycus et al. | |
| 7,169,146 B2 | 1/2007 | Truckai et al. | |
| 7,186,253 B2 | 3/2007 | Truckai et al. | |
| 7,189,233 B2 | 3/2007 | Truckai et al. | |
| 7,220,951 B2 | 5/2007 | Truckai et al. | |
| 7,309,849 B2 | 12/2007 | Truckai et al. | |
| 7,311,709 B2 | 12/2007 | Truckai et al. | |
| 7,354,440 B2 | 4/2008 | Truckai et al. | |
| 7,381,209 B2 | 6/2008 | Truckai et al. | |
| 7,955,332 B2 | 6/2011 | Arts et al. | |
| 8,128,624 B2 * | 3/2012 | Couture | A61B 18/1442 606/50 |
| 8,177,804 B2 | 5/2012 | Weisshaupt et al. | |
| 8,277,447 B2 | 10/2012 | Garrison et al. | |
| 8,430,876 B2 | 4/2013 | Kappus et al. | |
| 8,939,974 B2 | 1/2015 | Boudreaux et al. | |
| 8,968,310 B2 | 3/2015 | Twomey et al. | |
| 9,089,327 B2 | 7/2015 | Worrell et al. | |
| 9,161,803 B2 | 10/2015 | Yates et al. | |
| 9,402,682 B2 | 8/2016 | Worrell et al. | |
| 9,545,253 B2 | 1/2017 | Worrell et al. | |
| 9,566,062 B2 | 2/2017 | Boudreaux | |
| 9,572,622 B2 | 2/2017 | Shelton, IV et al. | |
| 9,610,114 B2 * | 4/2017 | Baxter, III | A61B 18/1442 |
| 9,610,116 B2 | 4/2017 | Twomey et al. | |
| 9,655,672 B2 | 5/2017 | Artale et al. | |
| 9,757,185 B2 | 9/2017 | Ward et al. | |
| 2002/0107517 A1 | 8/2002 | Witt et al. | |
| 2002/0111624 A1 | 8/2002 | Witt et al. | |
| 2005/0261678 A1 * | 11/2005 | Truckai | A61B 18/14 606/51 |
| 2009/0131933 A1 | 5/2009 | Ghabrial et al. | |
| 2011/0087220 A1 | 4/2011 | Felder | |
| 2012/0078243 A1 | 3/2012 | Worrell et al. | |
| 2013/0296843 A1 | 11/2013 | Boudreaux | |
| 2018/0008337 A1 | 1/2018 | Baxter, III et al. | |

FOREIGN PATENT DOCUMENTS

| | | |
|---|---|---|
| EP | 0853922 | 7/1998 |
| EP | 2428177 | 3/2012 |
| JP | 2009-240781 A | 10/2009 |
| JP | 2011-072788 A | 4/2011 |
| JP | 2011-524201 A | 9/2011 |
| JP | 2012-075899 A | 4/2012 |

OTHER PUBLICATIONS

U.S. Appl. No. 15/662,401, filed Jul. 28, 2017.
U.S. Appl. No. 61/410,603, filed Nov. 5, 2010.
U.S. Appl. No. 61/641,443, filed May 2, 2012.
Chinese Office Action, Notification of the First Office Action, dated Feb. 6, 2017 for Application No. 201480006484.9, 13 pgs.
Chinese Office Action, The Second Office Action, dated Oct. 30, 2017 for Application No. CN 201480006484.9, 7 pgs.
Chinese Search Report, Supplemental, dated Dec. 18, 2017 for Application No. CN 201480006484.9, 1 pg.
European Examination Report dated May 12, 2017 for Application No. EP 14703001.9, 4 pgs.
Japanese Office Action, Notification of Reasons for Refusal, dated Oct. 24, 2017 for Application No. 2015-555187, 4 pgs.
Japanese Office Action, Decision to Grant a Patent, dated Mar. 20, 2018 for Application No. JP 2015-555187, 2 pgs.

* cited by examiner

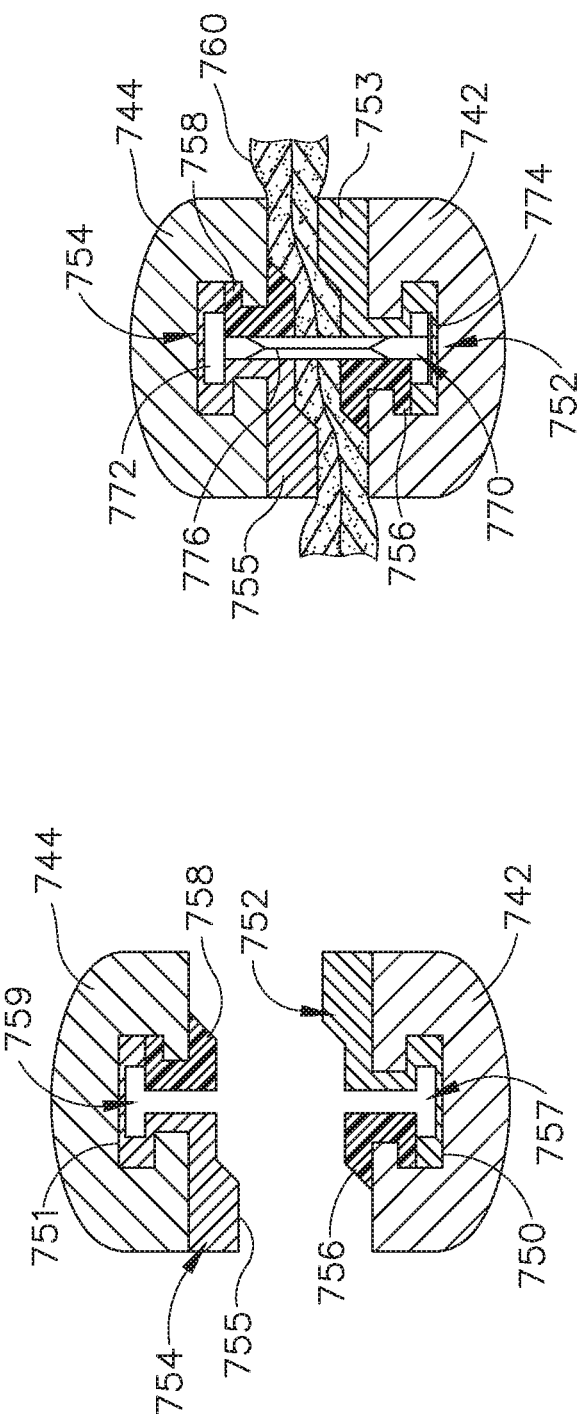

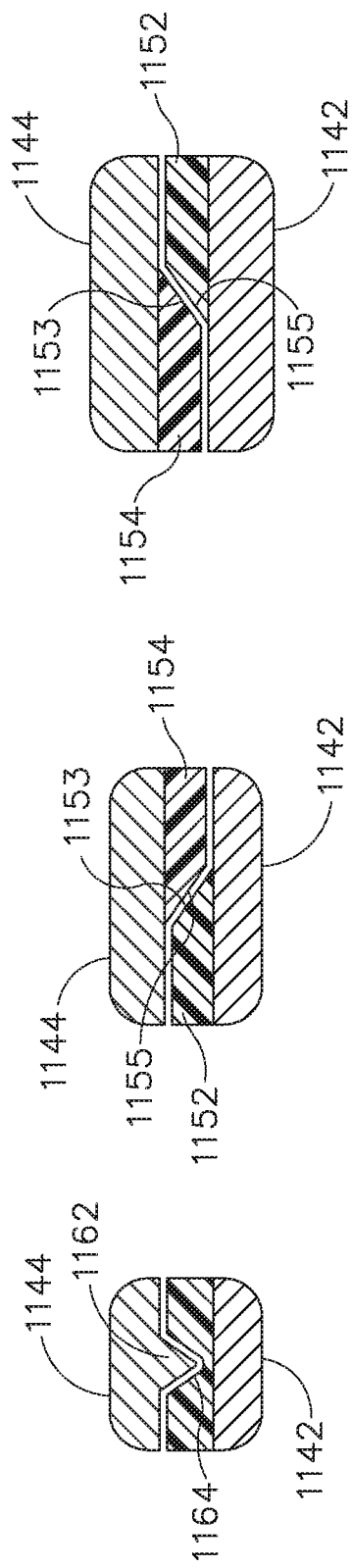

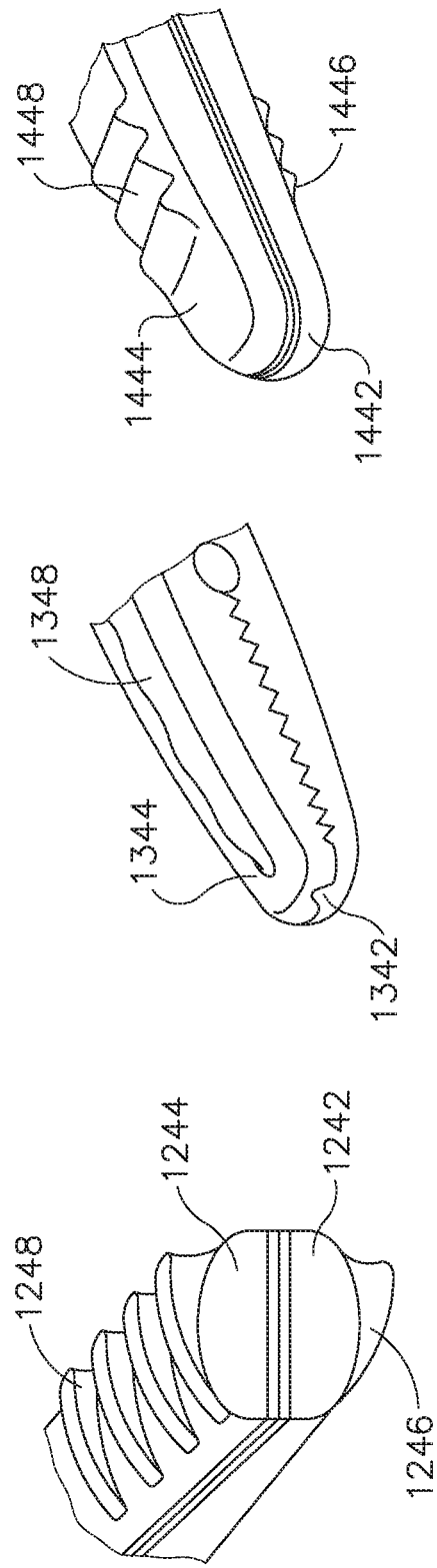

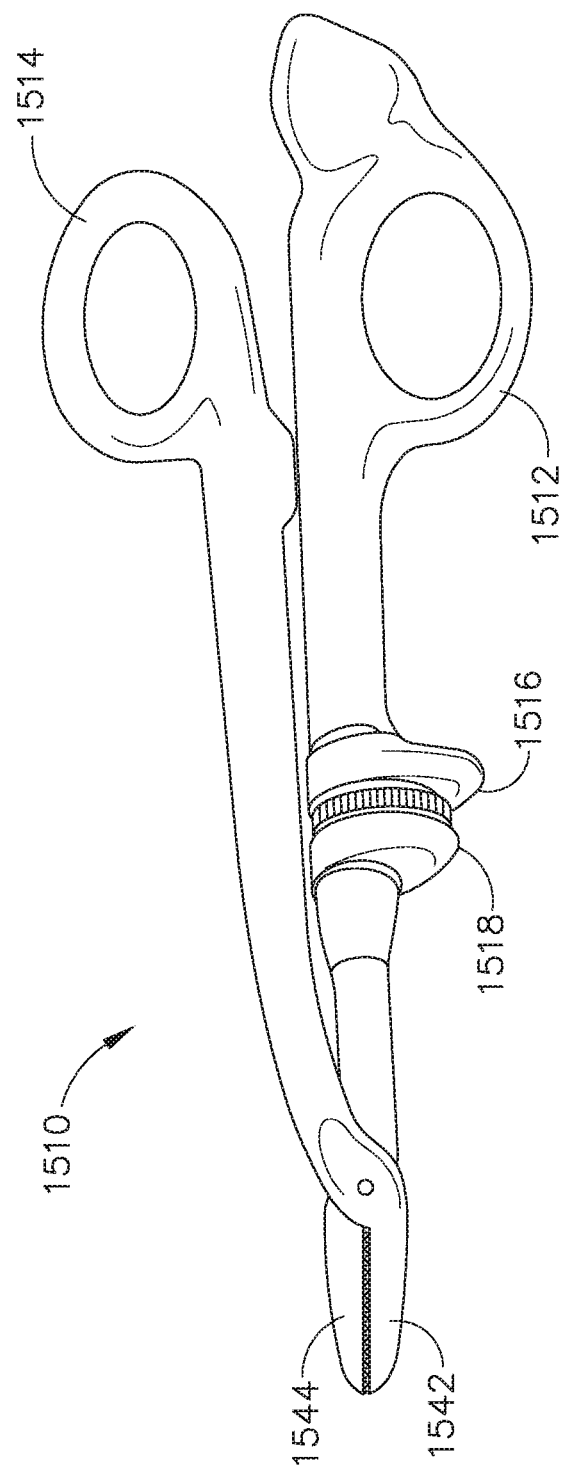

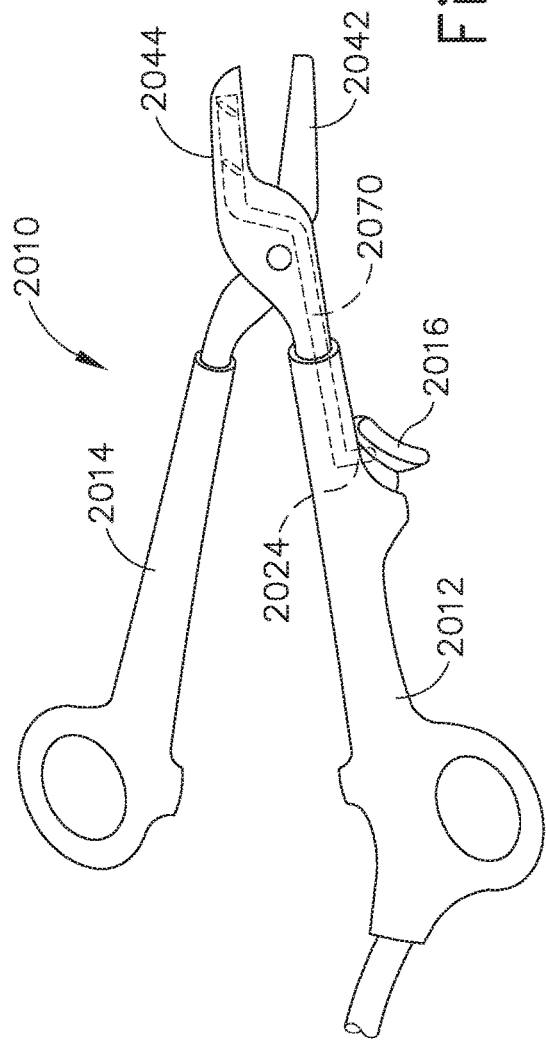
Fig.35
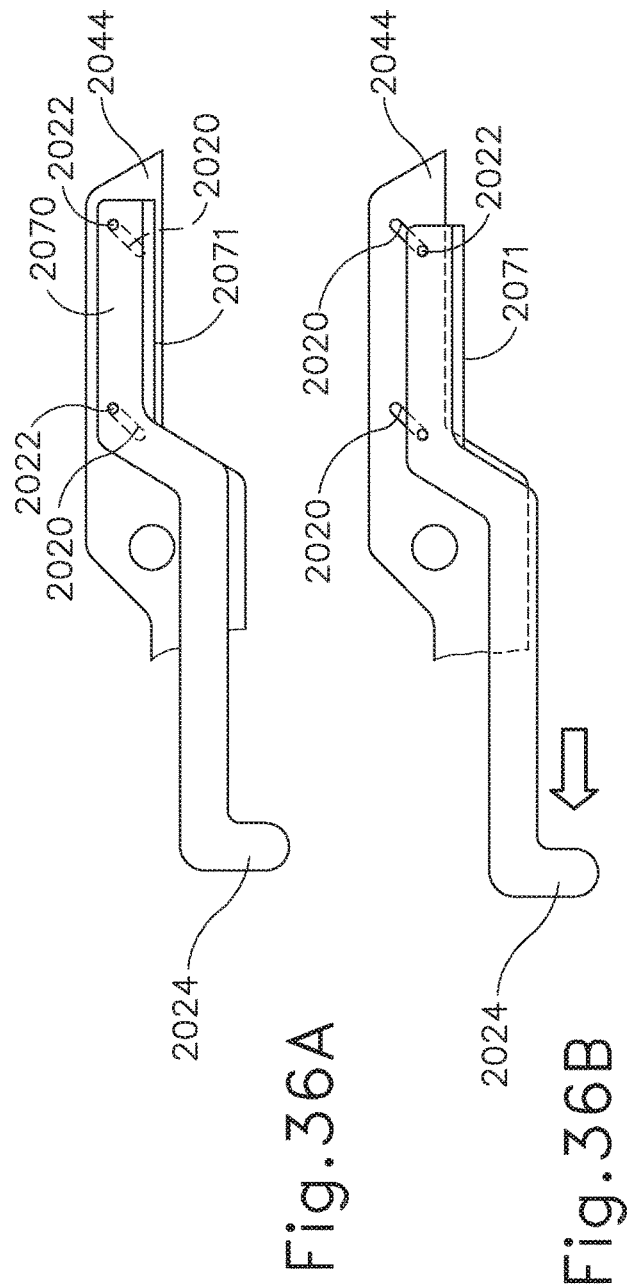
Fig.36A
Fig.36B

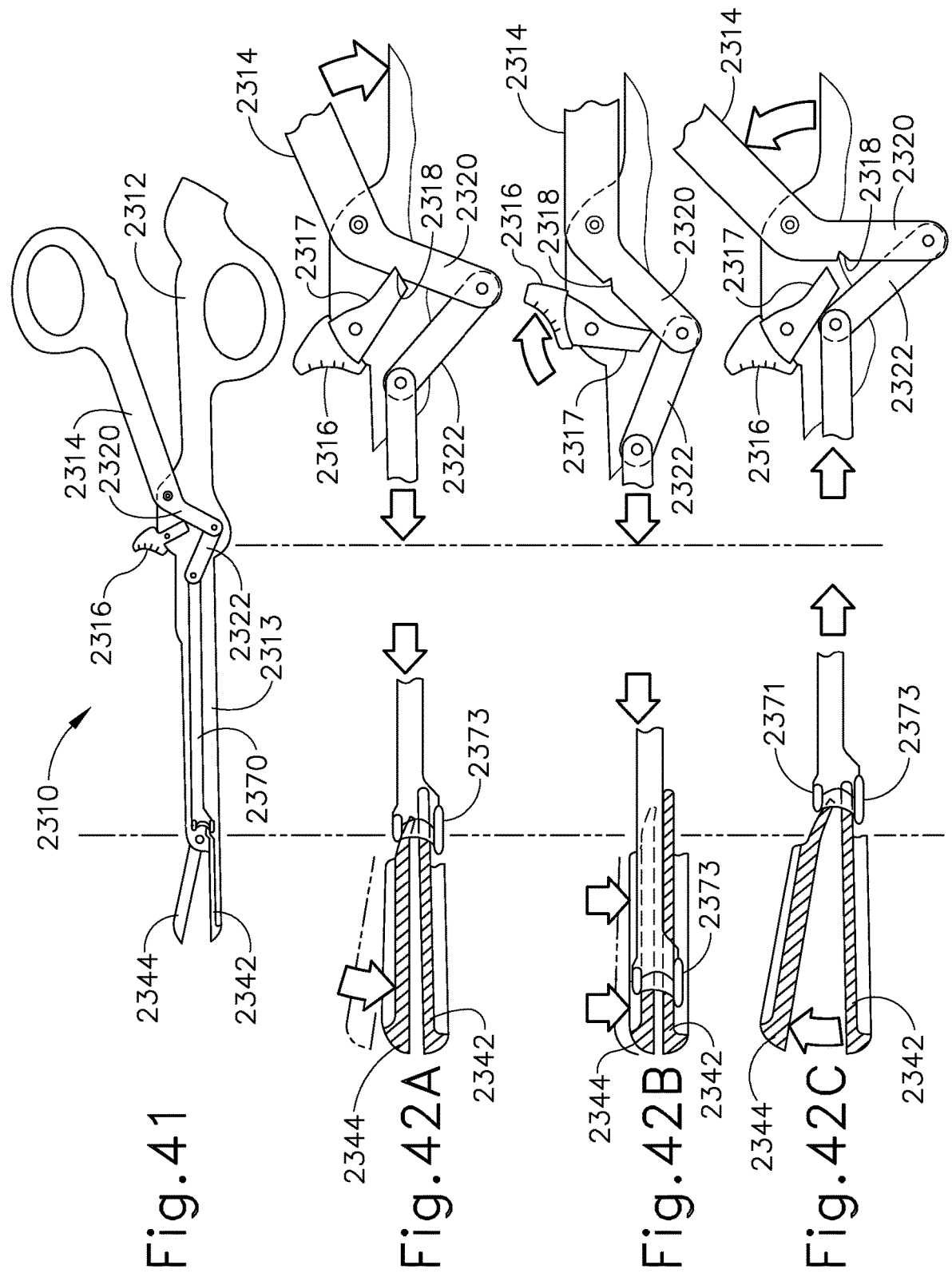

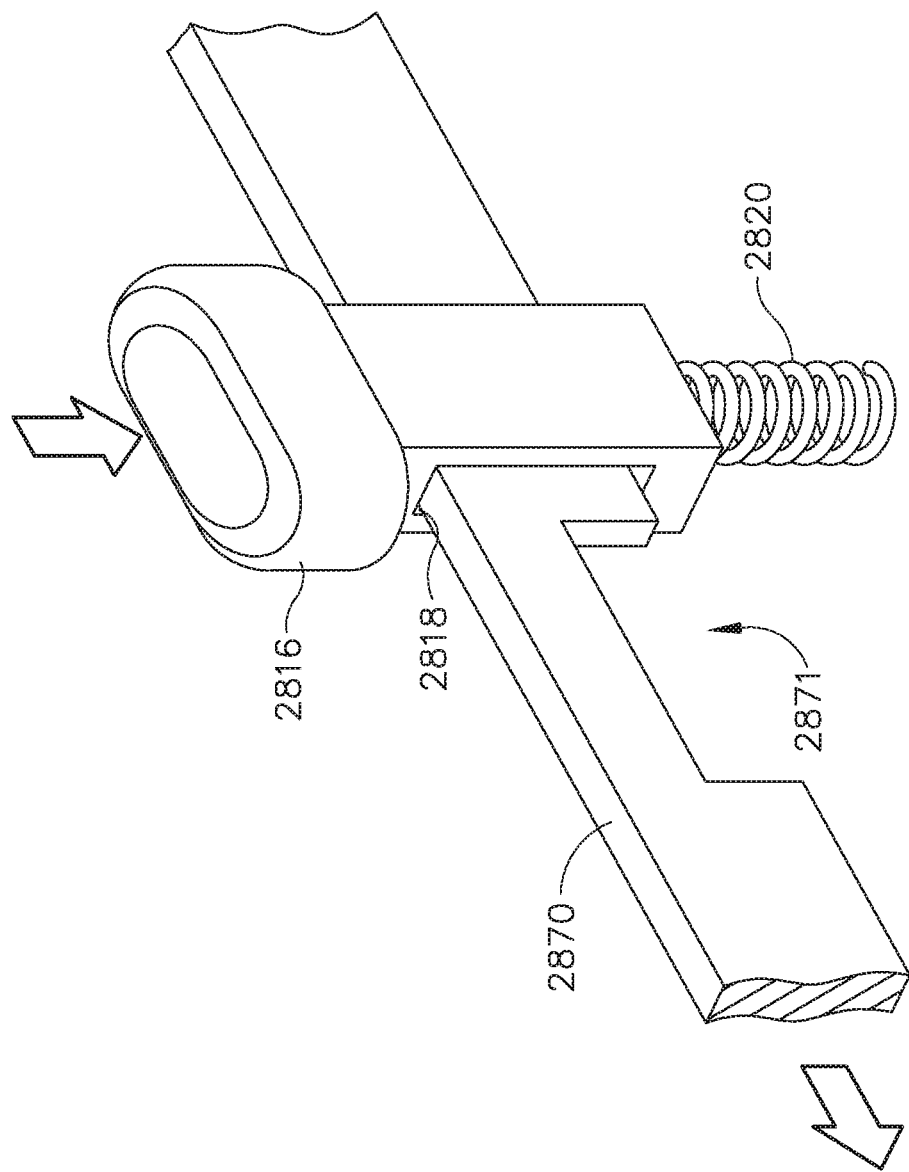

BIPOLAR ELECTROSURGICAL HAND SHEARS

This application is a continuation of U.S. application Ser. No. 13/752,588, filed Jan. 29, 2013, entitled "Bipolar Electrosurgical Hand Shears," issued as U.S. Pat. No. 9,610,114 on Apr. 4, 2017.

BACKGROUND

A variety of surgical instruments include one or more elements that transmit RF energy to tissue (e.g., to coagulate or seal the tissue). Some such instruments comprise a pair of jaws that open and close on tissue, with conductive tissue contact surfaces that are operable to weld tissue clamped between the jaws. In open surgical settings, some such instruments may be in the form of forceps having a scissor grip.

In addition to having RF energy transmission elements, some surgical instruments also include a translating tissue cutting element. An example of such a device is the ENSEAL® Tissue Sealing Device by Ethicon Endo-Surgery, Inc., of Cincinnati, Ohio. Further examples of such devices and related concepts are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein.

Additional examples of electrosurgical cutting instruments and related concepts are disclosed in U.S. Pub. No. 2011/0087218, entitled "Surgical Instrument Comprising First and Second Drive Systems Actuatable by a Common Trigger Mechanism," published Apr. 14, 2011, now U.S. Pat. No. 8,939,974, issued on Jan. 27, 2015, the disclosure of which is incorporated by reference herein; U.S. Pub. No. 2012/0116379, entitled "Motor Driven Electrosurgical Device with Mechanical and Electrical Feedback," published May 10, 2012, now U.S. Pat. No. 9,161,803, issued on Oct. 20, 2015, the disclosure of which is incorporated by reference herein; U.S. Pub. No. 2012/0078243, entitled "Control Features for Articulating Surgical Device," published Mar. 29, 2012, issued as U.S. Pat. No. 9,877,720, on Jan. 30, 2018, the disclosure of which is incorporated by reference herein; U.S. Pub. No. 2012/0078247, entitled "Articulation Joint Features for Articulating Surgical Device," published Mar. 29, 2012, now U.S. Pat. No. 9,402,682, issued on Aug. 2, 2016, the disclosure of which is incorporated by reference herein; U.S. patent application Ser. No. 13/622,729, entitled "Surgical Instrument with Multi-Phase Trigger Bias," filed Sep. 19, 2012, now U.S. Pat. No. 9,089,327, issued on Jul. 28, 2015, the disclosure of which is incorporated by reference herein; and U.S. patent application Ser. No. 13/622,735, entitled "Surgical Instrument with Contained Dual Helix Actuator Assembly," filed Sep. 19, 2012, now U.S. Pat. No. 9,545,253, issued on Jan. 17, 2017, the disclosure of which is incorporated by reference herein.

While several medical devices have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 16 depicts a front, cross sectional view of an exemplary alternative insert in jaws of a forceps instrument shaped to fit a knife;

FIG. 17 depicts a front, cross sectional view of the insert of FIG. 16 clamping tissue with the knife advanced;

FIG. 24 depicts a cross sectional view of the jaws of FIG. 23 taken along line 24-24 in FIG. 23;

FIG. 25 depicts a cross sectional view of the jaws of FIG. 23 taken along line 25-25 in FIG. 23;

FIG. 26 depicts a cross sectional view of the jaws of FIG. 23 taken along line 26-26 in FIG. 23;

FIG. 27 depicts a cross sectional perspective view of exemplary alternative jaws for a forceps instrument;

FIG. 28 depicts a perspective view of exemplary alternative jaws for a forceps instrument;

FIG. 29 depicts a perspective view of exemplary alternative jaws for a forceps instrument;

FIG. 30 depicts a side view of an exemplary alternative forceps instrument with a two button actuation system for energizing and cutting;

FIG. 35 depicts a side view of an exemplary alternative forceps instrument with a cam slot operated knife lock;

FIG. 36A depicts a side view of a knife and jaw of the instrument of FIG. 35 with the knife engaging the cam features;

FIG. 36B depicts a side view of the knife and jaw of FIG. 36A with the knife disengaging the cam features;

FIG. 41 depicts a side view of an exemplary alternative forceps instrument with a knife lockout feature;

FIG. 42A depicts a partial side view of the forceps instrument of FIG. 41 with jaws closed;

FIG. 42B depicts a partial side view of the forceps instrument of FIG. 41 with a trigger disengaging the handle and the knife advancing;

FIG. 42C depicts a partial side view of the forceps instrument of FIG. 41 with the jaws released;

FIG. 49B depicts a perspective view of the spring loaded knife lockout feature of FIG. 48 disengaged and with the knife advanced;

Figure 1:
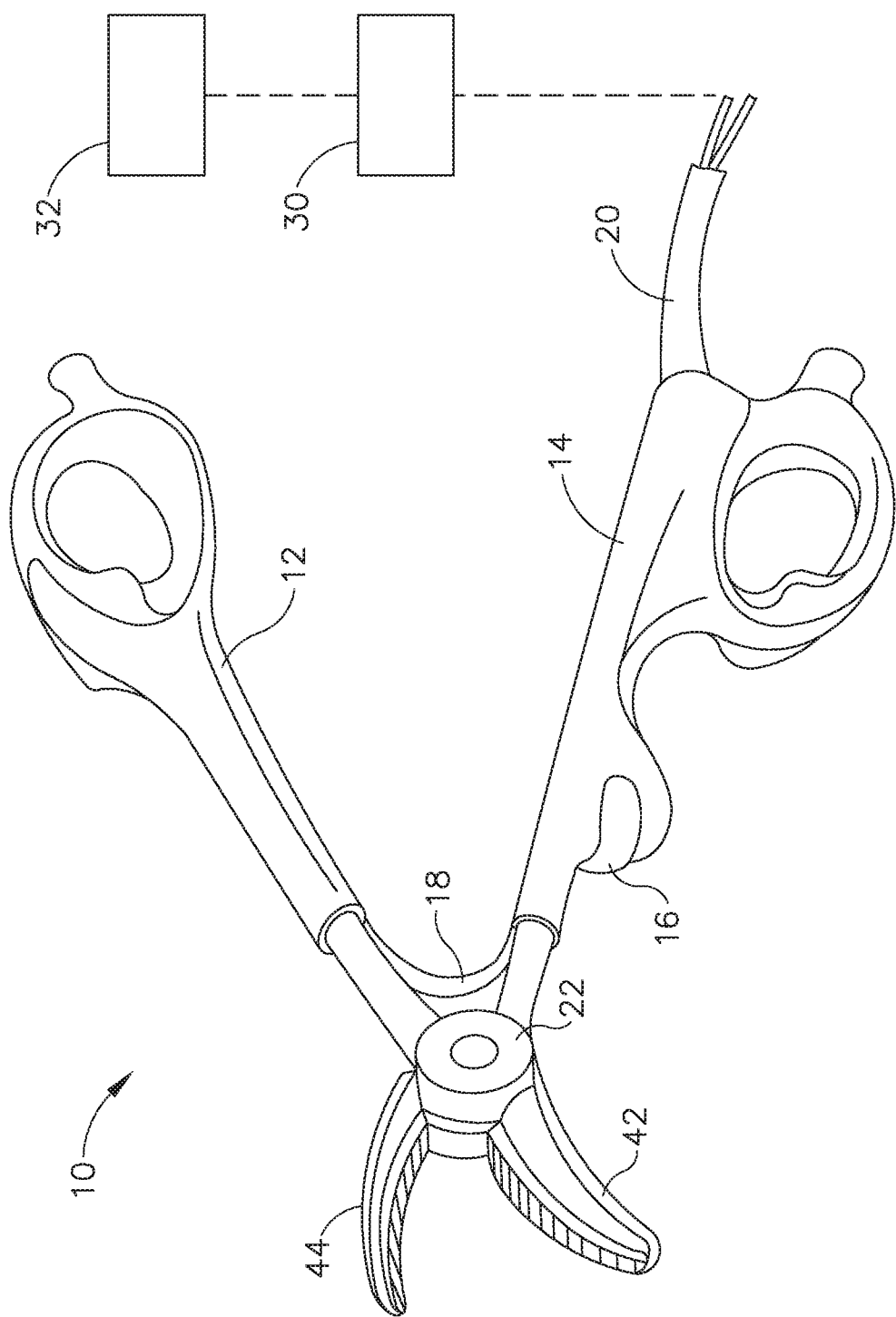
FIG. 1 depicts a perspective view of an exemplary forceps instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Exemplary Forceps Instrument

FIG. 1 shows an exemplary forceps instrument (10) operable to manipulate tissue. Instrument (10) comprises a first handle (12), a second handle (14), and a pivoting joint (22) that couples handles (12, 14) together. Handles (12, 14) may comprise glass filled nylon and/or any other suitable material(s). Handles (12, 14) are electrically isolated from each other in the present example, as will be described in greater detail below. A resilient strip (18) is positioned proximal to pivoting joint (22) and resiliently biases handles (12, 14) to an open configuration as shown in FIG. 1. By way of example only, resilient strip (18) may comprise a leaf spring. Of course, any other suitable component may be used to resiliently bias handles (12, 14). Alternatively, handles (12, 14) may simply lack a resilient bias. Instrument (10) further comprises a first jaw (42) in communication with first handle (12) and a second jaw (44) in communication with second handle (14). A cable (20) is also in communication with second handle (14), with a controller (30), and with a power source (32). Instrument (10) also comprises a trigger button (16) mounted on second handle (14).

Generally, instrument (10) is operable to grasp tissue. It will be understood that grasping tissue may include grasping the tissue with relatively little compressive force as well as grasping tissue with moderate to heavy compressive force. Furthermore, in some instances, it will be appreciated that a mix of compressive forces may be used. For instance, the user may wish to apply light compressive forces to some portions of tissue and heavier forces to other portions of tissue. In some cases, the user may wish to manipulate (pull, push aside, etc.) the tissue. Manipulation of tissue may include pulling or pushing grasped tissue. Furthermore, the user may even wish to use outer facing portions of the distal end of instrument (10) to bluntly move tissue in the surgical area as the user desires. Instrument (10) is further operable to energize the tissue by communicating bipolar RF energy to the tissue, which causes the tissue to weld or seal together. While bipolar RF energy is delivered by instrument (10) in the present example, it should be understood that other suitable forms of energizing the tissue may be used as would be apparent to one of ordinary skill in the art in view of the teachings herein. It should also be understood that before, after, or concurrently with sealing tissue, instrument (10) may be used to cut tissue. In particular, tissue clamped and sealed with instrument (10) may be cut using cutting edges within instrument (10). In addition or in the alternative, instrument (10) may use an actuating knife or other blade that moves relative to instrument (10) to cut grasped tissue. In some versions, other portions of instrument (10) may be moved against tissue in order to cut or pull apart tissue. By way of example only, jaws (42, 44) may themselves be operable to cut tissue simply by squeezing handles (12, 14) toward each other with enough force.

Handles (12, 14) are operable to be grasped by a user and squeezed together in a scissor grip fashion. While the exemplary version shows handles (12, 14) having a scissor grip configuration, it will be understood that other types of grips may be used for handles (12, 14). For instance, handles (12, 14) may have a pistol grip or any other suitable configuration operable to allow a user to close jaws (42, 44) through manual actuation of handles (12, 14); and to allow a user to manipulate instrument (10) once tissue is grasped between jaws (42, 44). Jaws (42, 44) have a curved configuration in the present example, but it will be understood that jaws (42, 44) may have any suitable configuration operable to grasp and manipulate tissue as would be apparent to one of ordinary skill in the art in view of the teachings herein. For instance, in some versions, jaws (42, 44) may have a straight configuration.

Figure 2:
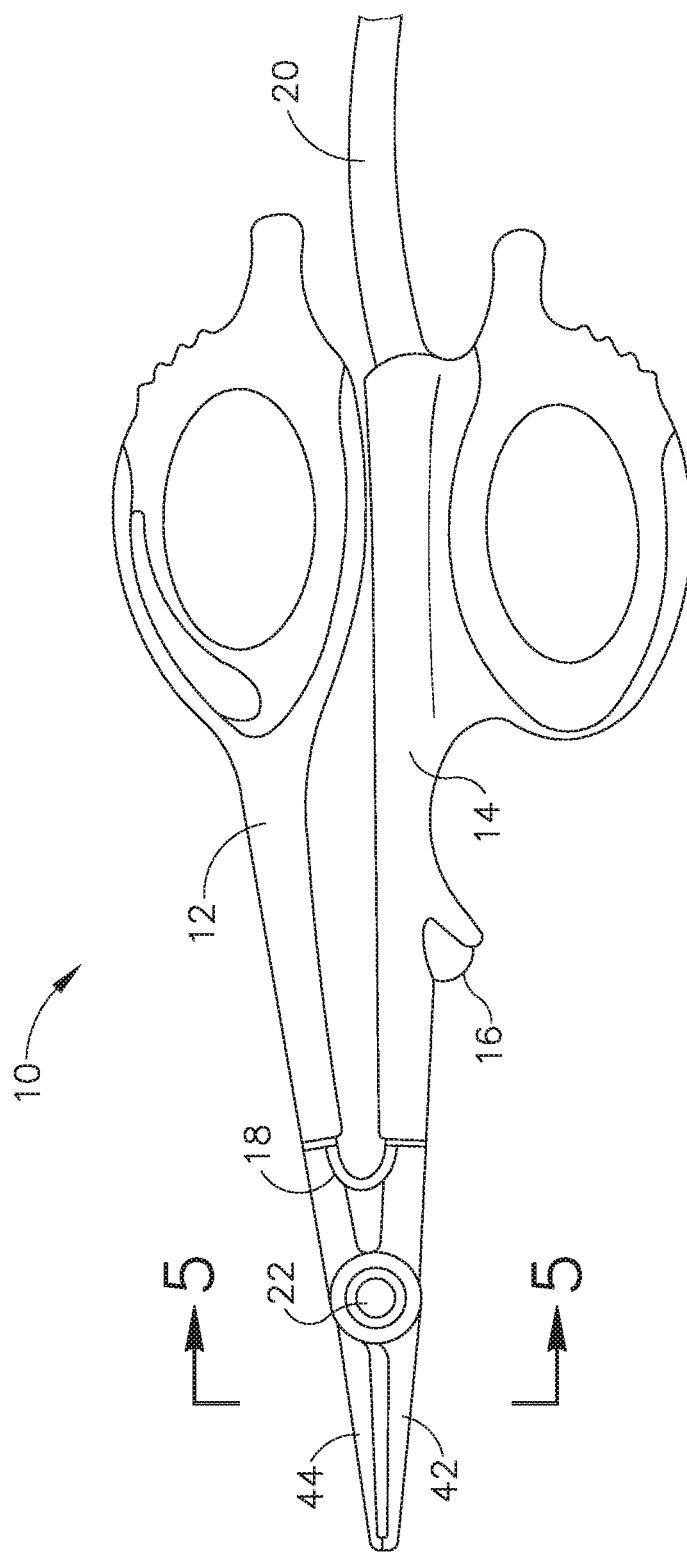
FIG. 2 depicts a side view of the instrument of FIG. 1 in a closed position.

Pivoting joint (22) is operable to allow jaws (42, 44) to open and close in response to a user actuating handles (12, 14). It will be understood that pivoting joint (22) may comprise any suitable joint or mechanism operable to allow the closure of jaws (42, 44) in response to user actuation of handles (12, 14) as would be apparent to one of ordinary skill in the art in view of the teachings herein. Resilient strip (18) is positioned near pivoting joint (22) and engages handles (12, 14) such that handles (12, 14) are biased to remain in the open position as seen in FIG. 1. When instrument (10) is in the closed position shown in FIG. 2, resilient strip (18) bends as seen in FIG. 2. When the user releases handles (12, 14) or simply loosens his or her grip on handles (12, 14), resilient strip (18) pushes apart handles (12, 14) to return instrument (10) to the state shown in FIG. 1.

Trigger button (16) is positioned on second handle (14) and is further positioned close enough to where a user might grip second handle (14) such that a user can grab handles (12, 14) and actuate trigger button (16) with the same hand that grasps handles (12, 14), thereby allowing single handed operation of instrument (10). Trigger button (16) may comprise a single push button as shown in the exemplary version but it will be understood that trigger button (16) may comprise multiple buttons or one or more buttons having multiple actuation stages.

Cable (20) comprises an electrically insulated cable in communication with controller (30). Cable (20) is further in communication with power source (32). Cable (20) comprises any suitable structure operable to deliver energy to jaws (42, 44) of instrument (10). In particular, cable (20) comprises at least two wires within cable (20) such that the wires are operable to deliver bipolar energy to jaws (42, 44). One or more wires may be in communication with first jaw (42) such that first jaw (42) acts as a positive lead whereas another set of one or more wires extending through cable (20) are in communication with second jaw (44) to act as a negative lead. As such, when jaws (42, 44) clamp tissue and deliver energy, bipolar energy is delivered to the tissue by passing from one jaw (42) through the tissue to the other jaw (44). While cable (20) connects to handle (14), it will be understood that cable (20) may be in communication with instrument (10) at any suitable portion of instrument (10).

Controller (30) and power source (32) are operable to deliver energy to instrument (10) through cable (20). In particular, controller (30) may comprise a circuit, processor, memory, and/or any other suitable components operable to start, stop, or otherwise control power source (32). Power source (32) is operable to deliver bipolar energy to jaws (42, 44) through cable (20).

Figure 3:
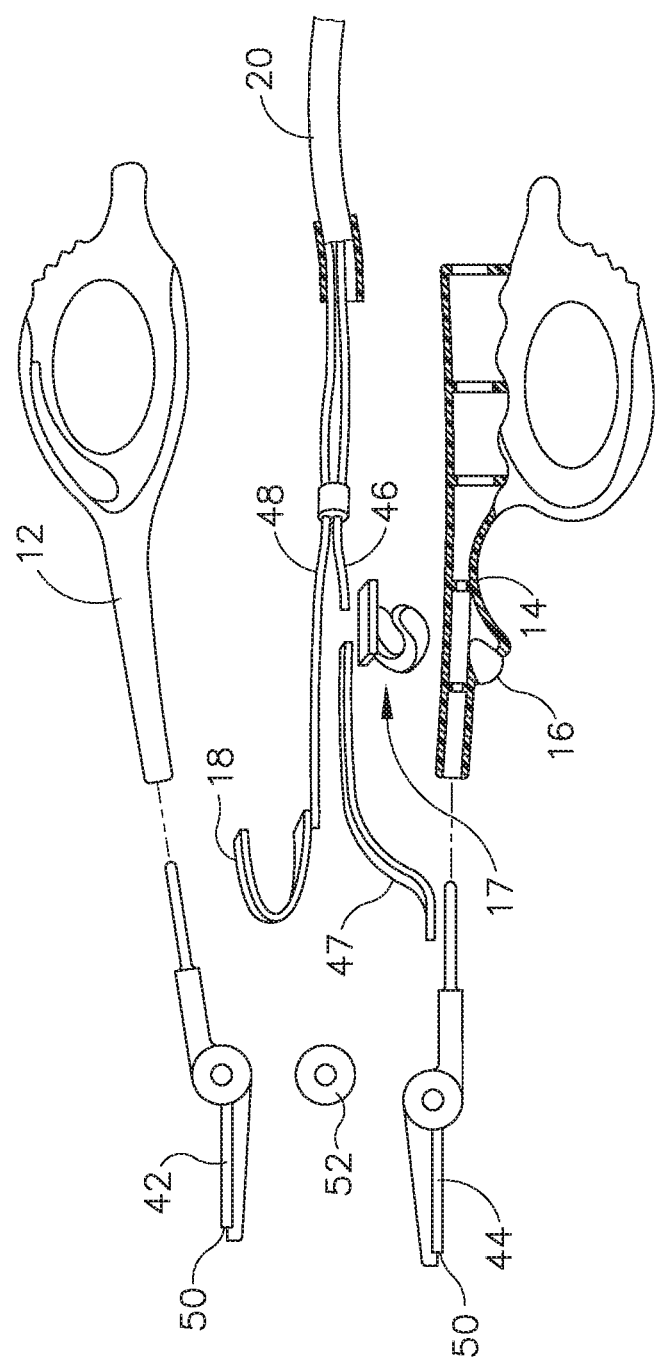
FIG. 3 depicts a side exploded view of the instrument of FIG. 1.

FIG. 3 shows an exploded view of instrument (10) to show generally how energy is transmitted from power source (32) and controller (30) to cable (20) and then to jaws (42, 44). In particular, cable (20) splits into a first wire (46) and a second wire (48). First wire (46) is coupled with a trigger switch (17), which is selectively opened and closed by actuation of trigger button (16). Of course, trigger button (16) is just one merely illustrative example of how the circuit may be selectively opened and closed. Any other suitable feature may be used. Trigger switch (17) is resiliently biased to the open position, such that a user must push trigger button (16) to close trigger switch (17); and such that trigger switch (17) will again open when the user thereafter releases trigger button (16). Trigger switch (17) is also coupled with a third wire (47), which is directly coupled with jaw (44). In some versions, trigger switch (17) is moved to the proximal region of handles (12, 14) and trigger button (16) is omitted. Such a proximal trigger switch (17) may be positioned between surfaces of handles (12, 14) that face each other and are moved toward each other when handles (12, 14) are squeezed together. By way of example only, trigger switch (17) may comprise a dome switch that is closed only when handles (12, 14) are squeezed together fully, indicating sufficient clamping of tissue between jaws (42, 44) before RF energy may be applied to the tissue. Other suitable positions and variations for trigger switch (17) will be apparent to those of ordinary skill in the art in view of the teachings herein.

Second wire (48) is directly coupled with resilient strip (18), which is electrically conductive and is further coupled with jaw (42) to provide an electrical path to jaw. It should be understood that resilient strip (18) does not contact any conductive regions of handle (14) or jaw (44). While resilient strip (18) itself provides an electrical path in this example, it should be understood that resilient strip (18) may alternatively just provide mechanical support to some other electrical conduit. For instance, a wire may be affixed to the proximal face of resilient strip (18).

Figure 4:
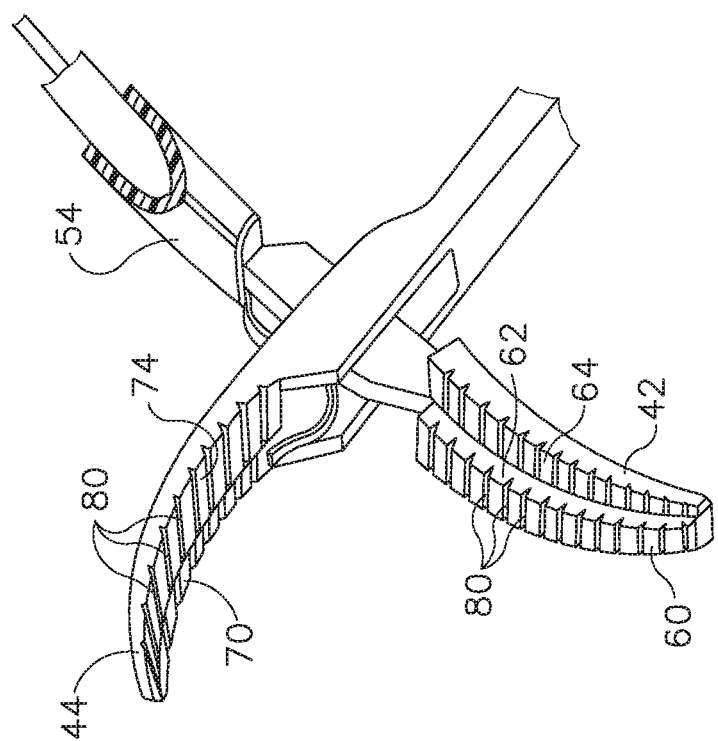
FIG. 4 depicts an enlarged perspective view of the jaws of the instrument of FIG. 1.

Instrument (10) further comprises insulating pads (50) and insulating washer (52). Insulating pads (50) and insulating washer (52) are operable to electrically insulate first wire (46) and associated components from second wire (48) and associated components in parts of instrument (10) where such positive and negative components are in particularly close proximity, thereby preventing positive and negative components from short circuiting. Furthermore, as seen in FIG. 4, it will be understood that portions of handle (12, 14) are constructed of an insulating exterior (54) such that as wires (46, 48) run through instrument (10), wires (46, 48) do not in create short circuits. Insulating exterior (54), insulating washer (52), and/or any other insulating features may be used to insulate handles (12, 14) from each other. It will be understood that jaws (42, 44) must be clamped against tissue and trigger button (16) must be actuated in order to close a circuit. Upon closing the circuit, bipolar RF energy is provided to the tissue.

Figure 5:
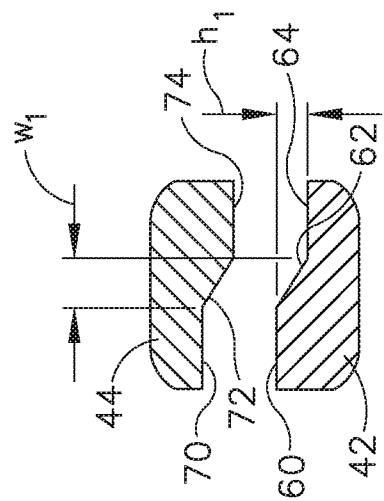
FIG. 5 depicts a front, cross sectional view of the jaws of FIG. 4, with the cross section taken along line 5-5 of FIG. 2.

Jaws (42, 44) can be seen in cross section in FIG. 5. Jaws (42, 44) define a clamping region therebetween having an asymmetric, stretched out stair step shape profile such that jaw (42) complements jaw (44). In particular, jaw (42) includes a first generally flat region (60), a sloped transition region (62), and a second generally flat region (64). Jaw (44) includes a first generally flat region (70), a sloped transition region (72), and a second generally flat region (74). Transition regions (62, 72) each have the same width ($w_1$) and a height ($h_1$). Regions (60, 70) are configured to complement each other, regions (62, 72) are configured to complement each other, and regions (64, 74) are configured to complement each other. Regions (60, 62, 64) thus nest with corresponding regions (70, 72, 74) when jaws (42, 44) are closed together. It should be understood that jaws (42, 44) may contact tissue across all regions (60, 62, 64, 70, 72, 74). Depending on how much force the user applies to handles (12, 14), this contact may simply clamp the tissue or cut the tissue.

In the present example, regions (64, 70) are conductive and apply RF energy to tissue while regions (60, 62, 72, 74) provide non-conductive tissue contact surfaces. For instance, regions (60, 62, 72, 74) may be coated with electrically insulative material while regions (64, 70) present exposed electrically conductive material (e.g., exposed metal). Regions (64, 70) may thus act as discrete, bipolar electrode surfaces. While jaws (42, 44) are generally formed of electrically conductive material in this example, regions (60, 62, 72, 74) include an electrically insulative coating. It should be understood that this configuration may provide electrode surfaces that are both vertically offset from each other and laterally offset from each other when jaws (42, 44) are closed. It should also be understood that this configuration may provide transmission of RF energy along a path that is oblique relative to the longitudinal axis of jaws (42, 44) in the vertical and lateral dimensions, with the path being generally parallel to regions (62, 72). In other words, the region of tissue that actually receives bipolar RF energy will only be the tissue that is contacting and between regions (62, 72). Thus, the tissue will not receive RF energy across the entire lateral width of jaws (42, 44). This configuration may thus minimize the thermal spread of heat caused by the application of bipolar RF energy to the tissue. Such minimization of thermal spread may in turn minimize potential collateral damage to tissue that is adjacent to the particular tissue region that the surgeon wishes to weld/seal/coagulate and/or cut.

In some other versions, regions (60, 62, 72, 74) are conductive and apply RF energy to tissue while regions (64, 70) provide non-conductive tissue contact surfaces. In still other versions, regions (62, 64, 70, 72) are conductive and apply RF energy to tissue while regions (60, 74) provide non-conductive tissue contact surfaces. In yet other versions, regions (60, 74) are conductive and apply RF energy to tissue while regions (62, 64, 70, 72) provide non-conductive tissue contact surfaces. Alternatively, all regions (60, 62, 64, 70, 72, 74) may be conductive and apply RF energy to tissue. In any of the foregoing examples, one jaw (42) may be associated with a first polarity while the other jaw (44) may be associated with a second polarity in order to apply bipolar RF energy to tissue.

As can be seen in FIG. 4, jaws (42, 44) of the present example also include sets of laterally oriented notches (80) in regions (60, 62, 64, 70, 72, 74). It should be understood that notches (80) are merely optional. It should also be understood that jaws (42, 44) may have a variety of alternative features and configurations. Several merely illustrative examples of such alternative features and configurations will be described in greater detail below, while additional examples will be apparent to those of ordinary skill in the art in view of the teachings herein.

II. Exemplary Alternative Jaw Features

Figure 7:
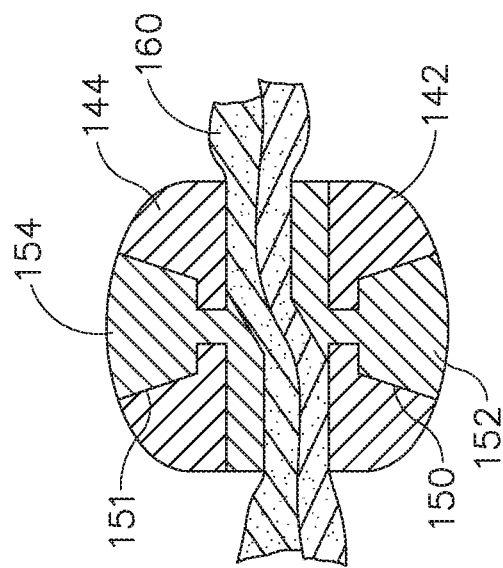
FIG. 7 depicts a front, cross sectional view of the jaw of FIG. 6.
Figure 6:
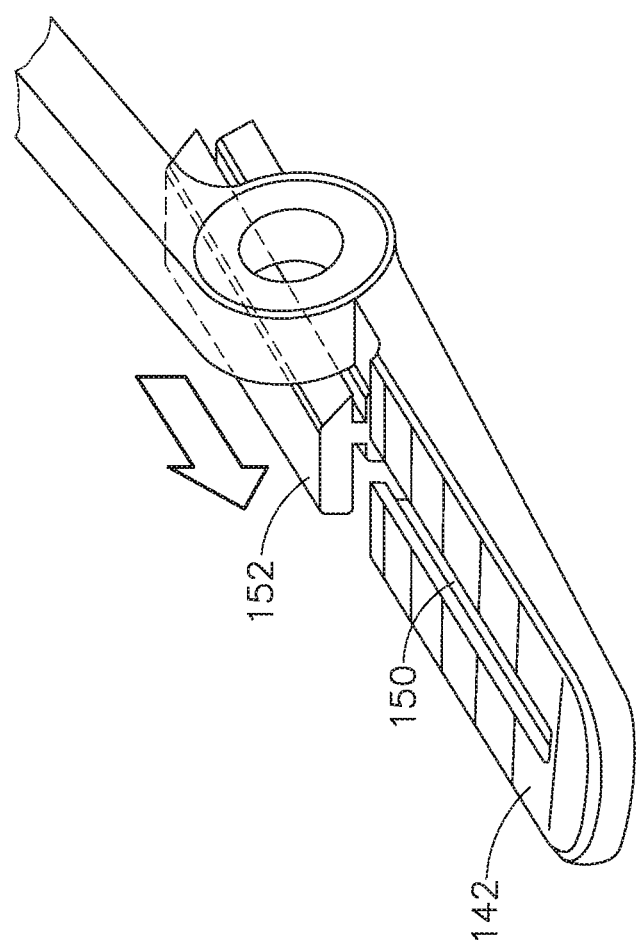
FIG. 6 depicts a perspective view of an exemplary alternative jaw with an insert.

FIGS. 6-29 show various examples of alternative forms that jaws (42, 44) may take. It should be understood that the various examples described below may be readily incorporated into instrument (10) and may apply bipolar RF energy to tissue. FIG. 6 in particular shows an exemplary jaw (142) having a longitudinally extending slot (150). Slot (150) extends longitudinally through the center of jaw (142) in this example. An insert (152) is slidably received in jaw (142) by sliding insert (152) into slot (150). FIG. 7 shows jaw (142) with insert (152) positioned within slot (150). Upper jaw (144) also comprises slot (151) similar to slot of lower jaw (142). A second insert (154) is configured to fit in slot (151). Inserts (152, 154) placed in slots (150, 151) are shaped and oriented such that tissue (160) clamped between inserts (152, 154) is obliquely compressed as shown in FIG. 7. Inserts (152, 154) form a dovetail fitting with jaws (142, 144) and are slidable into jaws (142, 144) from the rear of jaws (142, 144) in the present example. Of course, any other suitable alternative to a dovetail configuration may be used; and/or inserts (152, 154) may slide in from the distal end of jaws (142, 144) if desired.

Inserts (152, 154) of the present example are formed of an electrically insulative material, while jaws (142, 144) are formed of an electrically conductive material. By way of example only, inserts (152, 154) may be formed of a surgical grade plastic and/or a positive temperature coefficient (PTC) thermistor polymer, etc. In versions where inserts (152, 154) comprise a PTC thermistor polymer, it should be understood that inserts (152, 154) may be electrically conductive when the temperature of inserts (152, 154) is below a certain threshold; while inserts (152, 154) may be electrically insulative when the temperature of inserts (152, 154) is above a certain threshold. Other materials that may be used to form inserts (152, 154) will be apparent to those of ordinary skill in the art in view of the teachings herein. By way of example only, jaws (142, 144) may be formed of titanium or aluminum that is anodized or coated with a conductive material such as diamond-like carbon (DLC), grade 5 titanium, and/or some other material. Other materials that may be used to form jaws (142, 144) will be apparent to those of ordinary skill in the art in view of the teachings herein.

In the present example, inserts (152, 154) fit within jaws (142, 144) such that only a portion of each jaw (142, 144) is covered by the respective insert (152, 154). The tissue contacting regions of jaws (142, 144) that are left exposed by inserts (152, 154) will act as electrode surfaces, such that the exposed surfaces of jaws (142, 144) are operable to deliver bipolar RF energy to tissue (160). Such delivery of RF energy may effectively weld/seal/coagulate the tissue (160) as described above, and may further assist with the severing of tissue (160) depending on how much force the user applies to jaws (142, 144) by squeezing handles (12, 14) toward each other.

In an exemplary use, a user first places inserts (152, 154) into slots (150, 151). In some instances, jaws (142, 144) must be completely separated from each other (e.g., completely decoupled at pivoting joint (22), etc.) in order for inserts (152, 154) to slide into slots (150, 151). In such versions, jaws (142, 144) are coupled together (e.g., at pivoting joint (22)) after inserts (152, 154) are inserted into slots (150, 151); and the coupling of jaws (142, 144) prevents inserts (152, 154) from thereafter sliding out of jaws (142, 144) during use. In addition or in the alternative, a snapping feature, interference fit, clip, and/or other feature/technique may be used to secure inserts (152, 154) relative to their respective jaws (142, 144). Once jaws (142, 144) are assembled with inserts (152, 154), the user may squeeze handles (12, 14) to clamp jaws (142, 144) with inserts (152, 154) against the tissue (160). RF energy is then delivered to the tissue (160) through the tissue contacting surfaces of jaws (142, 144) that are left exposed by inserts (152, 154), thereby welding/sealing/coagulating the tissue (160). The user may then squeeze handles (12, 14) further, eventually pinching the tissue (160) to the point of cutting the tissue (160) along where inserts (152, 154) meet.

Figure 9:
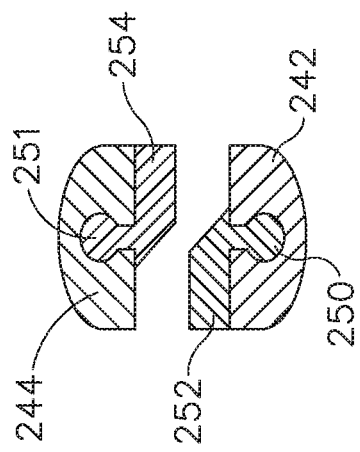
FIG. 9 depicts a front, cross sectional view of the jaw of FIG. 8.
Figure 8:
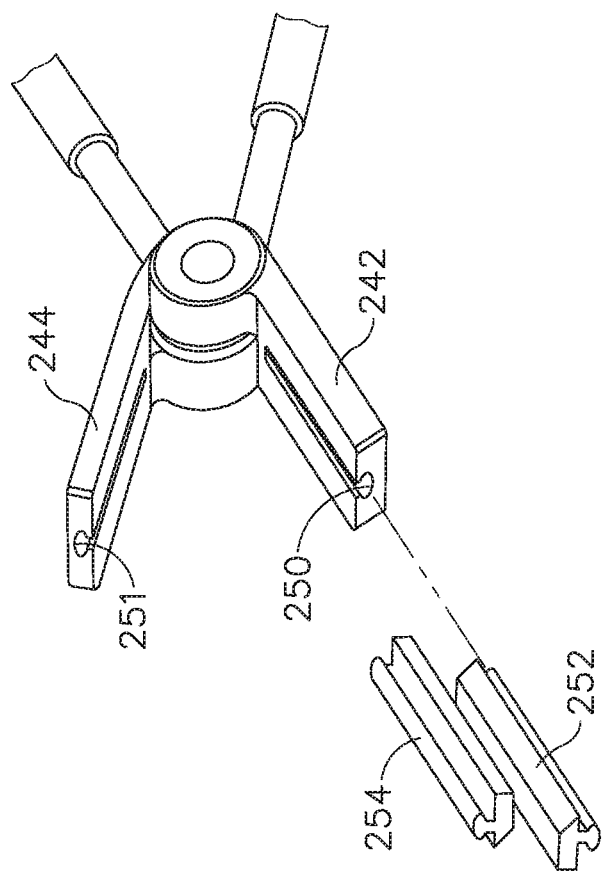
FIG. 8 depicts a perspective view of exemplary alternative jaws with inserts.

FIGS. 8-9 show exemplary alternative inserts (252, 254) that are configured to fit in slots (250, 251) of jaws (242, 244). In this example, inserts (252, 254) are insertable into jaws (242, 244) through the front of jaws (242, 244), though it should be understood that jaws (242, 244) may alternatively receive inserts (252, 254) from the proximal ends of jaws (242, 244). FIG. 9 shows inserts (252, 254) positioned within jaws (242, 244). Inserts (252, 254) and jaws (242, 244) are substantially identical to inserts (152, 154) and jaws (142, 144) described above, except that slots (251) and the complementary features of inserts (152, 154) have a bulb-shaped profile in this example instead of having a dovetail-shaped profile. Of course, any other suitable interface configuration may be used.

Figures 10A, 10B, 10C:
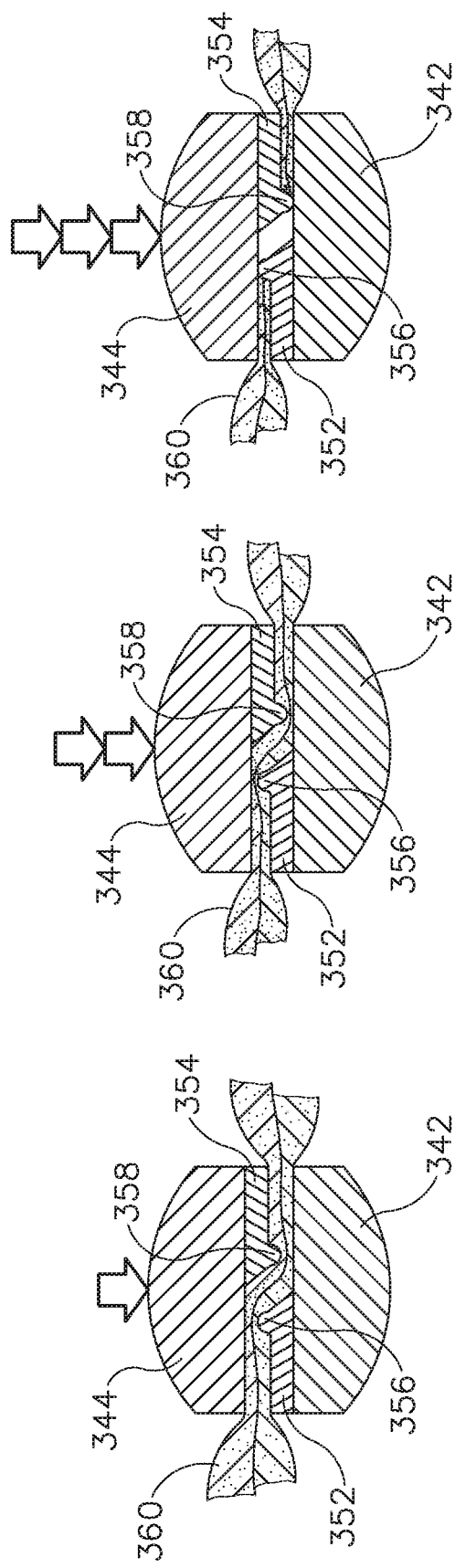
FIG. 10A depicts a front, cross sectional view of an exemplary alternative version of an insert for jaws of a forceps instrument, with the jaws clamping tissue.
FIG. 10B depicts a front, cross sectional view of the insert of FIG. 10A with the jaws welding tissue.
FIG. 10C depicts a front, cross sectional view of the insert of FIG. 10A with the jaws cutting tissue.

FIGS. 10A-10C show yet other set of exemplary alternative inserts (352, 354) and jaws (342, 344) that are operable to clamp, weld/seal/coagulate, and cut tissue (360). Inserts (352, 354) of this example are welded to jaws (342, 344), though it should be understood that inserts (352, 354) may alternatively be secured to jaws (342, 344) using any suitable features and/or techniques. Again, inserts (352, 354) of this example are formed of an electrically insulative material; while jaws (342, 344) are formed of an electrically conductive material. Inserts (352, 354) comprise ridges (356, 358) that extend along the longitudinal length of inserts (352, 354). FIG. 10A shows jaws (342, 344) urged toward each other to a point where jaws (342, 344) are merely clamping on tissue (360). FIG. 10B shows jaws (342, 344) urged further toward each other, with jaws (342, 344) being energized with RF energy, to a point where jaws (342, 344) are welding/sealing/coagulating tissue (360). FIG. 10C shows jaws (342, 344) urged further toward each other to a point where ridges (356, 358) are severing tissue (360).

It should be understood that the configuration of ridges (356, 358) assist in concentrating the pressure applied through jaws (342, 344) and inserts (352, 354) along the lines of tissue contact established by ridges (356, 358). This concentration of pressure may facilitate the severing of tissue (360) without requiring the user to apply significant forces at handles (12, 14). In the present example, ridges (356, 358) have a generally rounded profile, though it should be understood that ridges (356, 358) may alternatively have a profile that is square, triangular, sharp, or of any other suitable configuration.

Figure 11C:
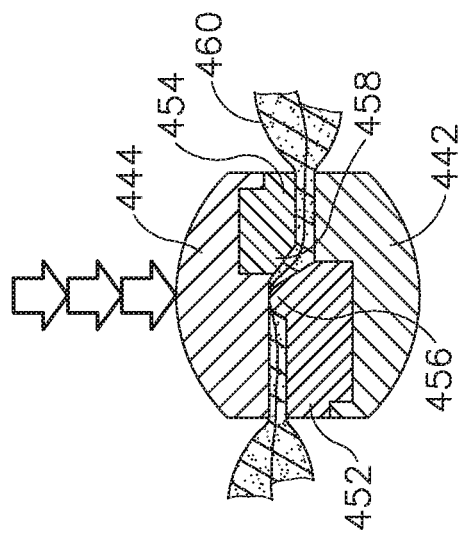
FIG. 11C depicts a front, cross sectional view of the insert of FIG. 11A, with the jaws cutting tissue.
Figure 11B:
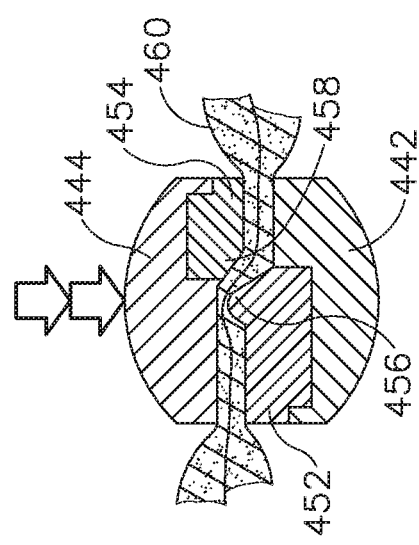
FIG. 11B depicts a front, cross sectional view of the insert of FIG. 11A, with the jaws welding tissue.
Figure 11A:
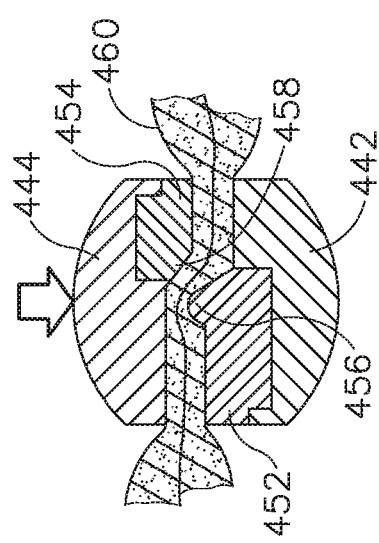
FIG. 11A depicts a front, cross sectional view of an exemplary alternative insert for jaws of a forceps instrument, with the jaws clamping tissue.

FIGS. 11A-11C show yet another set of exemplary alternative inserts (452, 454) and jaws (442, 444) that are operable to clamp, weld/seal/coagulate, and cut tissue (460). Inserts (452, 454) of this example fit in shallow slots (450, 451) of jaws (442, 444), though it should be understood that inserts (452, 454) may alternatively be secured to jaws (442, 444) using any suitable features and/or techniques. Inserts (452, 454) comprise humps (456, 458) that extend along the longitudinal length of inserts (452, 454). FIG. 11A shows jaws (442, 444) urged toward each other to a point where jaws (442, 444) are merely clamping on tissue (460). FIG. 11B shows jaws (442, 444) urged further toward each other, with jaws (442, 444) being energized with RF energy, to a point where jaws (442, 444) are welding/sealing/coagulating tissue (460). FIG. 11C shows jaws (442, 444) urged further toward each other to a point where ridges (456, 458) are severing tissue (460). Humps (456, 458) are configured to generally concentrate pressure being applied to tissue (460), such that humps (456, 458) may be viewed as a substitute for ridges (356, 358) described above.

Figure 13:
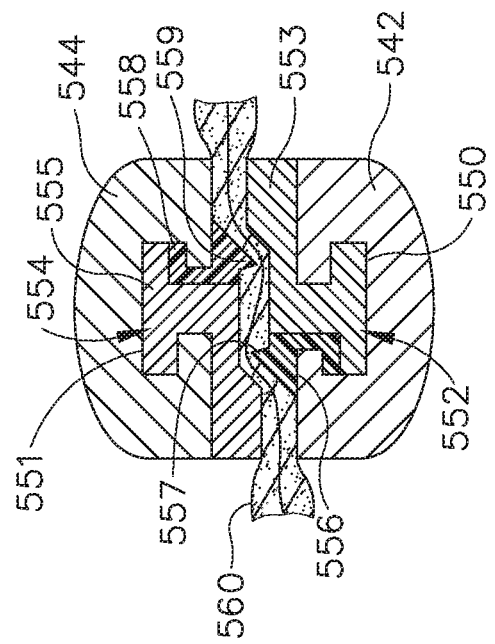
FIG. 13 depicts a front, cross sectional view of the insert of FIG. 12 inserted into jaws.
Figure 12:
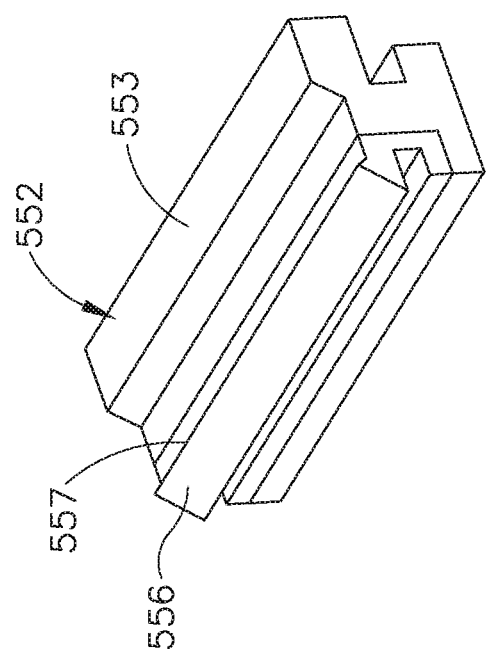
FIG. 12 depicts a perspective view of an exemplary alternative insert for a jaw of a forceps instrument with a pressure edge.

FIGS. 12-13 show yet another set of exemplary alternative inserts (552, 554) and jaws (542, 544) that are operable to clamp, weld/seal/coagulate, and cut tissue (560). Inserts (552, 554) of this example slidably fit in respective "T"-shaped slots (550, 551) of jaws (542, 544). Insert (552) comprises a plastic, electrically insulative portion (553) and a positive temperature coefficient (PTC) thermistor polymer portion (556). PTC thermistor polymer portion (556) defines a raised edge (557). Insert (554) comprises a plastic, electrically insulative portion (555) and a PTC thermistor polymer portion (558). PTC thermistor polymer portion (558) defines a raised edge (559). As can be seen in FIG. 13, PTC thermistor polymer portions (556, 558) extend partially into respective "T"-shaped slots (550, 551), adjacent to plastic, electrically insulative portions (553, 555).

It should be understood that PTC thermistor polymer portions (556, 558) may be electrically conductive when the temperature of PTC thermistor polymer portions (556, 558) is below a certain threshold; while PTC thermistor polymer portions (556, 558) may be electrically insulative when the temperature of PTC thermistor polymer portions (556, 558) is above a certain threshold. Thus, when the temperature of PTC thermistor polymer portions (556, 558) is below a certain threshold and RF energy is applied to jaws, RF energy may flow through tissue (560) from PTC thermistor polymer portion (556) to PTC thermistor polymer portion (558). It should be understood that this RF energy flow path through tissue (560) is oblique, similar to the oblique RF energy path described above with respect to jaws (42, 44). RF energy may also flow through tissue (560) from the tissue contacting surface of jaw (542) to the tissue contacting surface of jaw (544) when the temperature of PTC thermistor polymer portions (556, 558) is below the threshold, still being along an oblique path. Once the temperature of PTC thermistor polymer portions (556, 558) exceeds the threshold, PTC thermistor polymer portions (556, 558) become electrically insulative. At that stage, to the extent that RF energy continues to flow through tissue (560) at all, the RF energy only flows through tissue (560) from the tissue contacting surface of jaw (542) to the tissue contacting surface of jaw (544). In some other versions, the entirety of each insert (552, 554) consists of insulative plastic, such that a PTC thermistor polymer is not used. In such versions, RF energy may simply flow through tissue (560) from the tissue contacting surface of jaw (542) to the tissue contacting surface of jaw (544), again along an oblique path.

It should also be understood that raised edges (557, 559) may act as pressure concentration features, concentrating the pressure applied through jaws (542, 544) and inserts (552, 554) along the lines of tissue contact established by raised edges (557, 559). This concentration of pressure may facilitate the severing of tissue (560) without requiring the user to apply significant forces at handles (12, 14). Raised edges (557, 559) are thus similar to ridges (356, 358) and humps (456, 458) described above, though raised edges (557, 559) of this example present a generally sharper edge than ridges (356, 358) and humps (456, 458). Raised edges (557, 559) are nevertheless not sharp enough to cut tissue (560) in the absence of significant pressure being applied to the tissue (560) in the present example.

Figure 15:
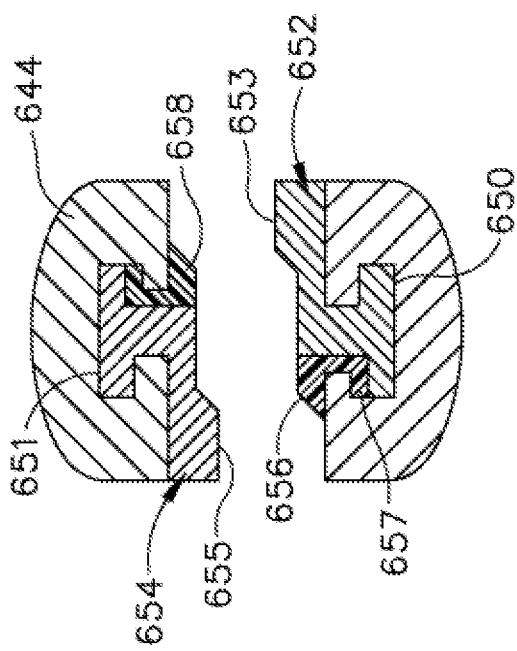
FIG. 15 depicts a front, cross sectional view of the insert of FIG. 14 inserted into jaws.
Figure 14:
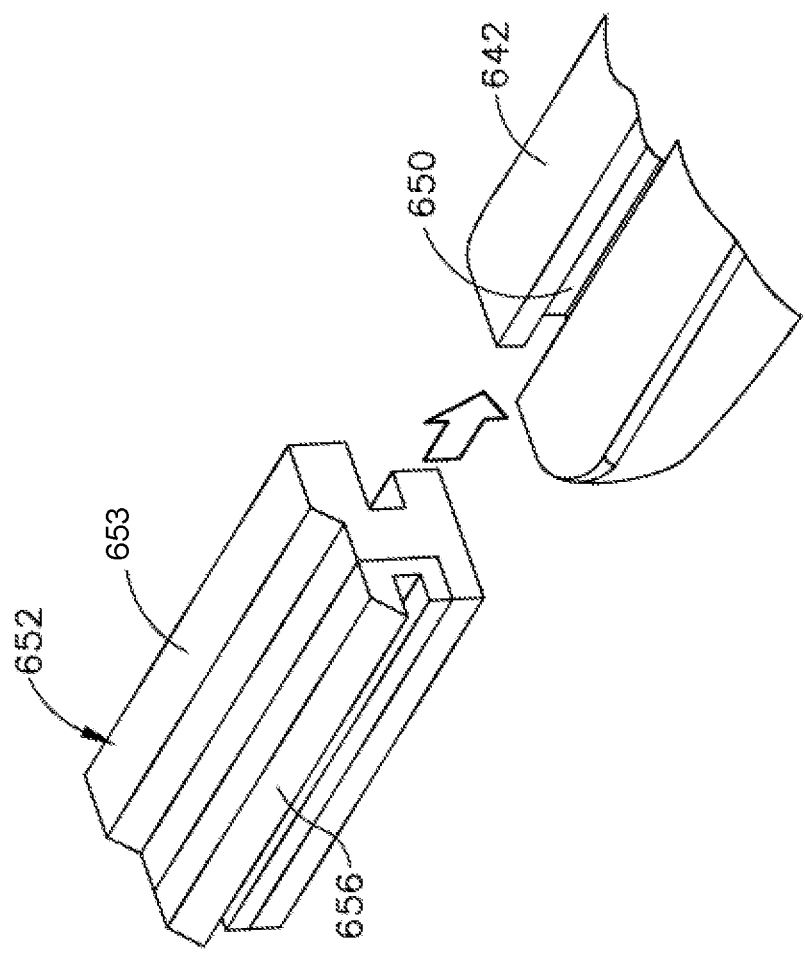
FIG. 14 depicts a perspective view of an exemplary alternative insert for a jaw of a forceps instrument being inserted into a jaw.

Of course, raised edges (557, 559) are merely optional. For instance, FIGS. 14-15 show a set of exemplary alternative inserts (652, 654) and jaws (642, 644) that are similar to inserts (552, 554) and jaws (542, 544); and that are operable to clamp, weld/seal/coagulate, and cut tissue. Inserts (652, 654) of this example sidably fit in respective "T"-shaped slots (650, 651) of jaws (642, 644). Insert (652) comprises a plastic, electrically insulative portion (653) and a positive temperature coefficient (PTC) thermistor polymer portion (656). PTC thermistor polymer portion (656) of this example does not define a raised edge or other type of pressure concentration feature. Insert (654) comprises a plastic, electrically insulative portion (655) and a PTC thermistor polymer portion (658). PTC thermistor polymer portion (658) also does not define a raised edge or other type of pressure concentration feature. As can be seen in FIG. 15, PTC thermistor polymer portions (656, 658) extend partially into respective "T"-shaped slots (650, 651), adjacent to plastic, electrically insulative portions (653, 655).

It should be understood that PTC thermistor polymer portions (656, 658) may be electrically conductive when the temperature of PTC thermistor polymer portions (656, 658) is below a certain threshold; while PTC thermistor polymer portions (656, 658) may be electrically insulative when the temperature of PTC thermistor polymer portions (656, 658) is above a certain threshold. Thus, when the temperature of PTC thermistor polymer portions (656, 658) is below a certain threshold and RF energy is applied to jaws, RF energy may flow through tissue from PTC thermistor polymer portion (656) to PTC thermistor polymer portion (658). It should be understood that this RF energy flow path through tissue is oblique, similar to the oblique RF energy path described above with respect to jaws (42, 44). RF energy may also flow through tissue from the tissue contacting surface of jaw (642) to the tissue contacting surface of jaw (644) when the temperature of PTC thermistor polymer portions (656, 658) is below the threshold, still being along an oblique path. Once the temperature of PTC thermistor polymer portions (656, 658) exceeds the threshold, PTC thermistor polymer portions (656, 658) become electrically insulative. At that stage, to the extent that RF energy continues to flow through tissue at all, the RF energy only flows through tissue from the tissue contacting surface of jaw (642) to the tissue contacting surface of jaw (644). In some other versions, the entirety of each insert (652, 654) consists of insulative plastic, such that a PTC thermistor polymer is not used. In such versions, RF energy may simply flow through tissue from the tissue contacting surface of jaw (642) to the tissue contacting surface of jaw (644), again along an oblique path.

It should also be understood that jaws (642, 644) and inserts (652, 654) may still be operable to cut tissue in the absence of raised edges or other tissue concentration features. For instance, jaws (642, 644) and inserts (652, 654) may sever tissue captured between jaws (642, 644) and inserts (652, 654) when handles (12, 14) are squeezed together with sufficient force. In some instances, such tissue may be more easily severed after RF energy has been applied to the tissue. By way of example only, the user may first partially clamp down on the tissue with jaws (642, 644) and inserts (652, 654), apply RF energy to the tissue for a certain period of time, then clamp down further on the tissue with jaws (642, 644) and inserts (652, 654) to sever the tissue. Other suitable features and methods of use will be apparent to those of ordinary skill in the art in view of the teachings herein.

III. Exemplary Jaws with Movable Tissue Cutting Feature

In some instances, an alternative cutting feature such as a movable knife may be used to sever tissue, instead of using clamping pressure through a variation of jaws (42, 44) to sever tissue. FIGS. 16-17 show an exemplary version of jaws (742, 744) having inserts (752, 754) and an I-beam knife (770). Inserts (752, 754) of this example are substantially similar to inserts (652, 654) described above, except that inserts (752, 754) of this example each define "T"-shaped slots (757, 759). Insert (752) comprises a plastic, electrically insulative portion (753) and a positive temperature coefficient (PTC) thermistor polymer portion (756). Insert (754) comprises a plastic, electrically insulative portion (755) and a PTC thermistor polymer portion (758). PTC thermistor polymer portions (756, 758) extend partially into respective "T"-shaped slots (750, 751) of jaws (742, 744), adjacent to plastic, electrically insulative portions (753, 755).

It should be understood that PTC thermistor polymer portions (756, 758) may be electrically conductive when the temperature of PTC thermistor polymer portions (756, 758) is below a certain threshold; while PTC thermistor polymer portions (756, 758) may be electrically insulative when the temperature of PTC thermistor polymer portions (756, 758) is above a certain threshold. Thus, when the temperature of PTC thermistor polymer portions (756, 758) is below a certain threshold and RF energy is applied to jaws, RF energy may flow through tissue (760) from PTC thermistor polymer portion (756) to PTC thermistor polymer portion (758). It should be understood that this RF energy flow path through tissue (760) is oblique, similar to the oblique RF energy path described above with respect to jaws (42, 44). RF energy may also flow through tissue (760) from the tissue contacting surface of jaw (742) to the tissue contacting surface of jaw (744) when the temperature of PTC thermistor polymer portions (756, 758) is below the threshold, still being along an oblique path. Once the temperature of PTC thermistor polymer portions (756, 758) exceeds the threshold, PTC thermistor polymer portions (756, 758) become electrically insulative. At that stage, to the extent that RF energy continues to flow through tissue (760) at all, the RF energy only flows through tissue (760) from the tissue contacting surface of jaw (742) to the tissue contacting surface of jaw (744). In some other versions, the entirety of each insert (752, 754) consists of insulative plastic, such that a PTC thermistor polymer is not used. In such versions, RF energy may simply flow through tissue from the tissue contacting surface of jaw (742) to the tissue contacting surface of jaw (744), again along an oblique path.

I-beam knife (770) of the present example includes a pair of outwardly directed upper transverse pins (772) and a pair of outwardly directed lower transverse pins (774). In some other versions, pins (772, 774) are substituted with transverse flanges and/or some other structure(s). The vertical distance between pins (772, 774) is fixed in the present example. I-beam knife (770) further includes a vertically extending sharp cutting edge (776). I-beam knife (770) is operable to translate longitudinally through jaws (742, 744), which would be into and out of the page in the views depicted in FIGS. 16-17. Pins (772) are disposed in the upper portion of "T"-shaped slot (759) of insert (754); while pins (774) are disposed in the lower portion of "T"-shaped slot (757) of insert (752).

In use, jaws (742, 744) may be closed on tissue (760) to compress tissue (760) and then weld/seal/coagulate tissue (760) as described above. Then, I-beam knife (770) may be driven distally to cut tissue (760) as shown in FIG. 17. Several merely illustrative examples of how I-beam knife (770) may be driven distally will be described in greater detail below; while further examples will be apparent to those of ordinary skill in the art in view of the teachings herein. In the event that jaws (742, 744) are not fully compressing tissue (760) when I-beam knife (770) is driven distally, pins (772, 774) may act as cams against inserts (752, 754) to thereby drive jaws (742, 744) to fully compressed positions.

In some versions, I-beam knife (770) is conductive and provides a return path for RF current from one or both of jaws (742, 744). Thus, if RF energy is applied when I-beam knife (770) is adjacent to tissue (e.g., during and/or after distal advancement of I-beam knife (770)), RF energy may flow through tissue (760) from the tissue contacting surface of jaw (742) to I-beam knife (770); and/or from the tissue contacting surface of jaw (744) to I-beam knife (770). At such a stage of operation, PTC thermistor polymer portions (756, 758) may have been heated to an electrically insulative state, such that PTC thermistor polymer portions (756, 758) would not serve as a short circuit path between I-beam knife (770) and jaws (742, 744). Alternatively, I-beam knife (770) may be insulative or may otherwise play no role in RF energy transmission. For instance, in some instances no RF energy is applied through jaws (742, 744) or I-beam knife (770) at the stage where I-beam knife (770) is driven through tissue (760).

Figure 19:
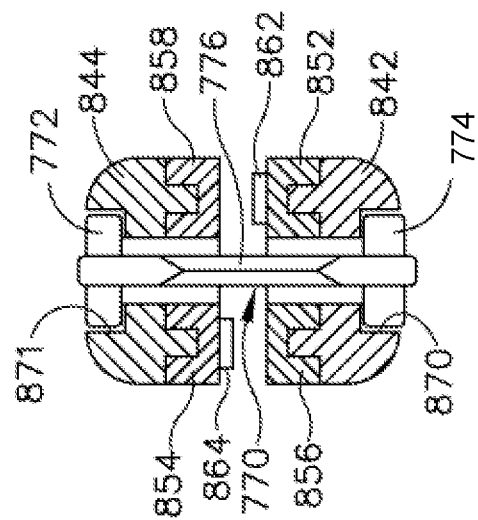
FIG. 19 depicts a front, perspective view of the jaws of FIG. 18.
Figure 18:
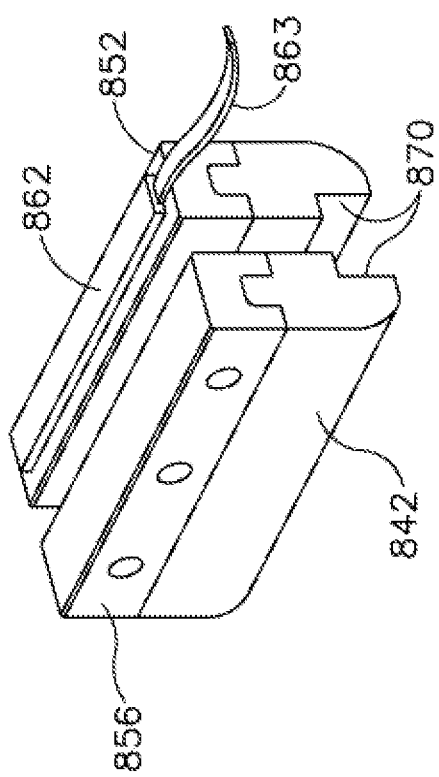
FIG. 18 depicts a perspective view of an exemplary alternative version of jaws of a forceps instrument with diagonally positioned electrodes.

FIGS. 18-19 show I-beam knife (770) combined with an exemplary alternative pair of jaws (842, 844). Jaws (842, 844) of this example have respective plastic, electrically insulative portions (852, 854), respective positive temperature coefficient (PTC) thermistor polymer portions (856, 858), and respective electrode strips (862, 864). Insulative portions (852, 854) are arranged on opposite sides of a vertical plane passing through the center of jaws (842, 844). PTC thermistor portions (856, 858) are also arranged on opposite sides of a vertical plane passing through the center of jaws (842, 844). Electrode strip (862) is secured to the top of insulative portion (852); while electrode strip (864) is secured to the top of insulative portion (854). By way of example only, electrode strips (862, 864) may be heat-staked, pinned, glued, overmolded, or otherwise secured to respective insulative portions (852, 854). Insulative portions (852, 854) may also be heat-staked, pinned, glued, overmolded, or otherwise secured to respective jaws (842, 844). Likewise, PTC thermistor portions (856, 858) may be heat-staked, pinned, glued, overmolded, or otherwise secured to respective jaws (842, 844). Other suitable ways in which the above-described components may be secured together will be apparent to those of ordinary skill in the art in view of the teachings herein.

While FIG. 18 only shows a flexible conduit (863) for providing power to electrode strip (862), it should be understood that a similar conduit may be coupled with electrode strip (864). It should also be understood that such conduits (863) may be coupled with wires (46, 48) described above, for activation in response to actuation of trigger button (16), etc.

It should be understood that PTC thermistor polymer portions (856, 858) may be electrically conductive when the temperature of PTC thermistor polymer portions (856, 858) is below a certain threshold; while PTC thermistor polymer portions (856, 858) may be electrically insulative when the temperature of PTC thermistor polymer portions (856, 858) is above a certain threshold. Thus, when the temperature of PTC thermistor polymer portions (856, 858) is below a certain threshold and RF energy is applied to jaws, RF energy may flow through tissue (not shown) from PTC thermistor polymer portion (856) to PTC thermistor polymer portion (858). It should be understood that this RF energy flow path through tissue is oblique, similar to the oblique RF energy path described above with respect to jaws (42, 44). RF energy may also flow through the tissue from electrode strip (862) to electrode strip (864), which is another oblique path. Furthermore, RF energy may also flow through the tissue from electrode strip (862) to PTC thermistor polymer portion (858); and from electrode strip (864) to PTC thermistor polymer portion (856). It should therefore be understood that RF energy may flow through tissue along four different paths when PTC thermistor polymer portions (856, 858) are in electrically conductive states.

Once the temperature of PTC thermistor polymer portions (856, 858) exceeds the threshold. PTC thermistor polymer portions (856, 858) become electrically insulative. At that stage, to the extent that RF energy continues to flow through the tissue at all, the RF energy only flows through the tissue from electrode strip (862) to electrode strip (864). In some other versions, PTC thermistor polymer portions (856, 858) are substituted with insulative plastic. In such versions, RF energy may simply flow through the tissue from electrode strip (862) to electrode strip (864), again along an oblique path. As another merely illustrative example, electrode strips (862, 864) may be omitted and RF energy may flow through tissue from PTC thermistor polymer portion (856) to PTC thermistor polymer portion (858) until the temperature exceeds a threshold, at which point RF energy stops flowing through the tissue.

As noted above, I-beam knife (770) of the present example includes a pair of outwardly directed upper transverse pins (772) and a pair of outwardly directed lower transverse pins (774). Pins (772) are disposed in a recess (871) defined in jaw (844); while pins (774) are disposed in a recess (870) defined in jaw (842). I-beam knife (770) is operable to translate longitudinally through jaws (842, 844), which would be into and out of the page in the view depicted in FIG. 19. In use, jaws (842, 844) may be closed on tissue to compress the tissue and then weld/seal/coagulate the tissue as described above. Then, I-beam knife (770) may be driven distally to cut the tissue. Again, several merely illustrative examples of how I-beam knife (770) may be driven distally will be described in greater detail below; while further examples will be apparent to those of ordinary skill in the art in view of the teachings herein. In the event that jaws (842, 844) are not fully compressing the tissue when I-beam knife (770) is driven distally, pins (772, 774) may act as cams against jaws (842, 844) to thereby drive jaws (842, 844) to fully compressed positions.

IV. Exemplary Jaws with External Tissue Sealing Features

Figure 20:
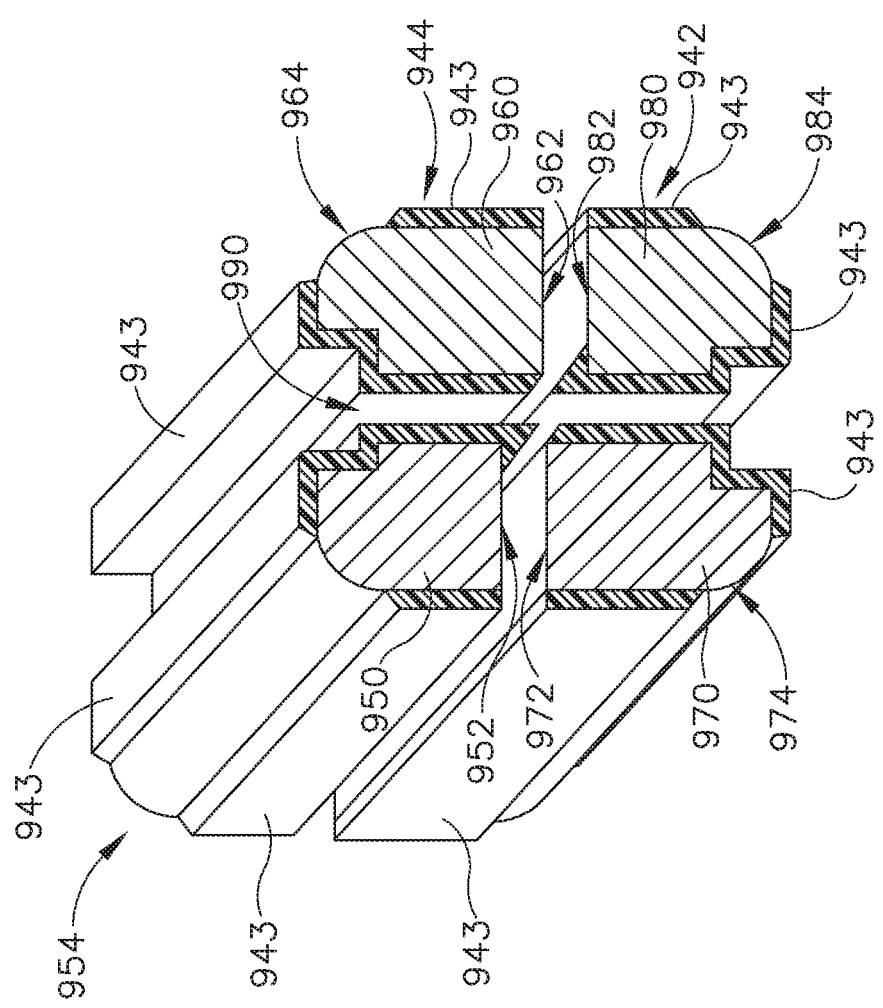
FIG. 20 depicts a perspective cross sectional view of an exemplary alternative version of jaws with externally facing electrodes.
Figure 22:
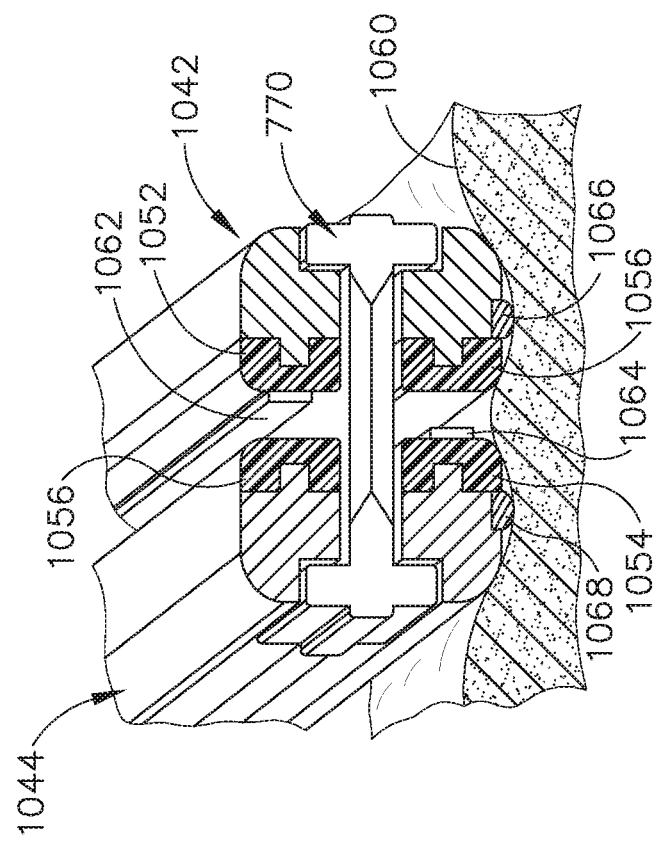
FIG. 22 depicts a perspective cross sectional view of the jaws of FIG. 21 rotated ninety degrees counterclockwise and pressed against tissue.
Figure 21:
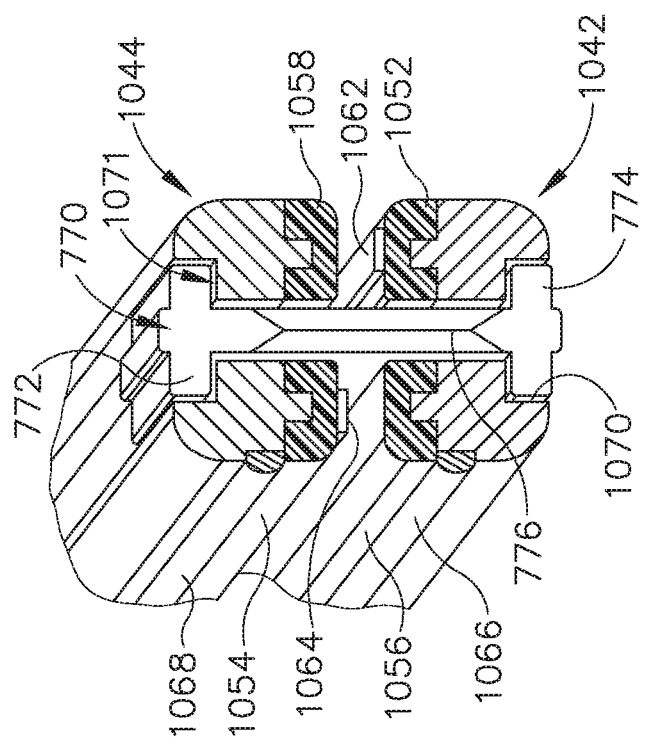
FIG. 21 depicts a perspective cross sectional view of an exemplary alternative version of jaws for a forceps instrument with external electrodes and a vertically oriented I-beam.
Figure 23:
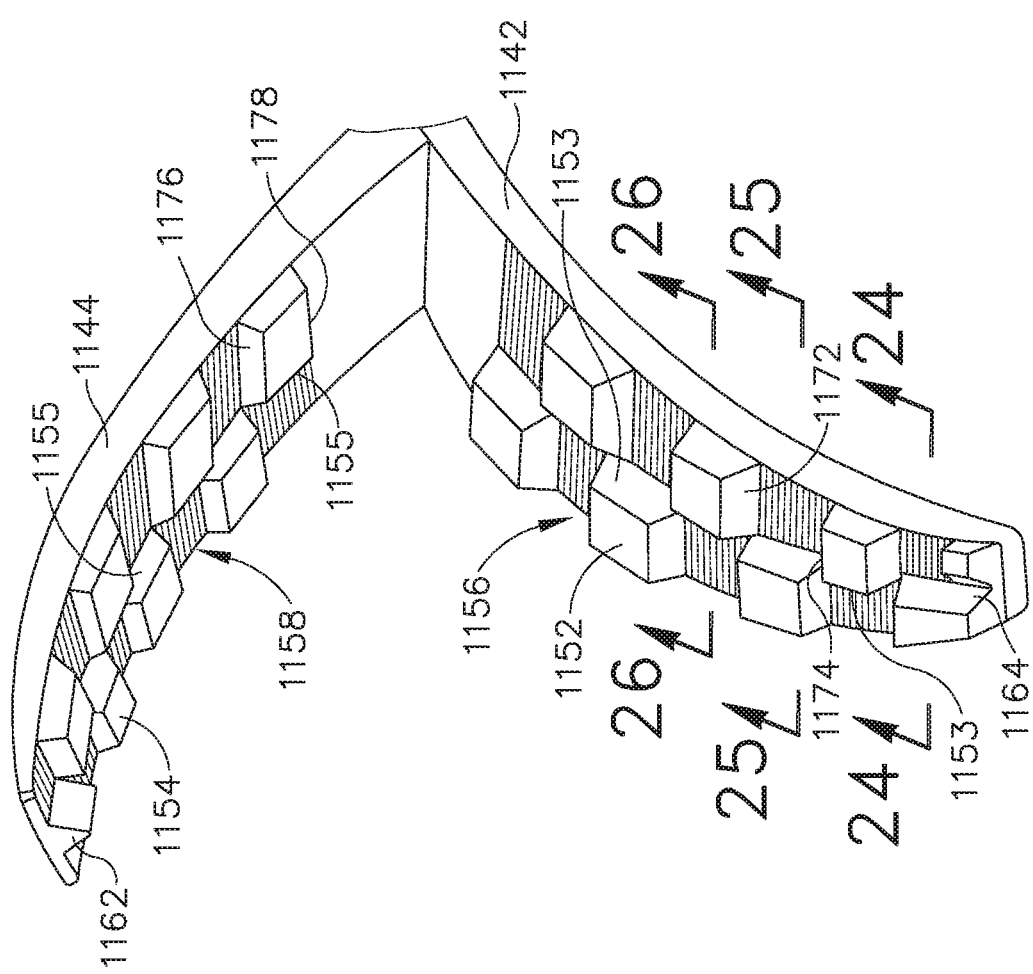
FIG. 23 depicts a perspective view of exemplary alternative jaws for a forceps instrument having checkerboard style contours.

The exemplary variations of jaws (42, 44) described above are operable to weld/seal/coagulate tissue that is captured between jaws (42, 44). In some instances, it may be desirable to weld/seal/coagulate tissue that is not captured between jaws (42, 44). For instance, after some version of jaws (42, 44) has been used to sever tissue, after an I-beam knife (770) has been used to sever tissue, and/or after some other feature has been used to sever or otherwise manipulate tissue, there may be a portion of tissue that continues to bleed. It may therefore be desirable to press an exterior portion of one or both of jaws (42, 44) against such a bleeding portion of tissue, to apply bipolar RF energy to seal/coagulate the tissue, without having to grasp the bleeding portion of tissue between jaws (42, 44). FIGS. 20-22 show merely illustrative variations of jaws (42, 44) that have exterior portions that are operable to apply bipolar RF energy to tissue. These examples will be described in greater detail below, while other examples will be apparent to those of ordinary skill in the art in view of the teachings herein.

FIG. 20 shows a pair of jaws (942, 944) that are each formed of an electrically conductive material (e.g., metal) and that each include a selectively applied electrically insulative coating (943). Various suitable materials that may be used to form insulative coating (943) will be apparent to those of ordinary skill in the art in view of the teachings herein. Upper jaw (944) comprises a negative polarity portion (950) and a positive polarity portion (960). Similarly, lower jaw (942) comprises a negative polarity portion (970) and a positive polarity portion (980).

Insulative coating (943) covers part of negative polarity portion (950), but leaves an internal tissue contact surface (952) exposed and an external tissue contact surface (954) exposed. Insulative coating (943) also covers part of positive polarity portion (960), leaving an internal tissue contact surface (962) exposed and an external tissue contact surface (964) exposed. Similarly, insulative coating (943) covers part of negative polarity portion (970), leaving an internal tissue contact surface (972) exposed and an external tissue contact surface (974) exposed. And likewise, insulative coating (943) covers part of positive polarity portion (980), leaving an internal tissue contact surface (982) exposed and an external tissue contact surface (984) exposed. It should be understood from the foregoing that surfaces (962, 964, 982, 984) are operable to provide a positive pole for RF energy communication through tissue; while surfaces (952, 954, 972, 974) are operable to provide a negative pole for RF energy communication through tissue. In some other versions, one or more of surfaces (952, 954, 962, 964, 972, 974, 982, 984) are covered by insulative coating (943). By way of example only, surfaces (962, 972) may be covered by insulative coating (943).

In the present example, surfaces (952, 962, 972, 982) are operable to communicate RF energy through tissue that is clamped between jaws (942, 944), to thereby weld/seal/coagulate the tissue. In particular, RF energy may be communicated through tissue from surface (962) to surface (972); and/or from surface (982) to surface (952). As shown in FIG. 20, surfaces (962, 972) are laterally and vertically offset from each other in this example, such that the RF energy will travel along an oblique path through tissue from surface (962) to surface (972), similar to the oblique path described above with respect to jaws (42, 44). Similarly, surfaces (952, 982) are also laterally and vertically offset from each other in this example, such that the RF energy will travel along an oblique path through tissue from surface (982) to surface (952).

Jaws (942, 944) of the present example also together define a slot (990) that is configured to receive I-beam knife (770). Thus, I-beam knife (770) may be used to sever tissue between jaws (942, 944) before, during, or after surfaces (952, 962, 972, 982) are activated to weld/seal/coagulate the tissue. It should be understood that inclusion of I-beam knife (770) is merely optional. By way of example only, jaws (942, 944) may instead include ridges, humps, sharp edges, and/or any other suitable features that are configured to concentrate pressure on tissue when jaws (942, 944) are sufficiently clamped on the tissue to sever the tissue.

Before or after jaws (942, 944) are used to weld/seal/coagulate tissue captured between jaws (942, 944), and perhaps before or after tissue is severed by an I-beam knife (770) that is driven distally through slot (990), the user may rotate jaws (942, 944) approximately ninety degrees about their longitudinal axis and press the exterior of one of jaws (942, 944) against tissue to seal/coagulate the tissue. For instance, the user may press the exterior of jaw (942) against tissue to place surfaces (974, 984) in contact with the tissue. Positive and negative polarity portions (970, 980) may then be energized to apply bipolar RF energy to the tissue through surfaces (974, 984), thereby welding/sealing the tissue along a region between the tissue contact points of surfaces (974, 984). Similarly, the user may press the exterior of jaw (944) against tissue to place surfaces (954, 964) in contact with the tissue. Positive and negative polarity portions (950, 960) may then be energized to apply bipolar RF energy to the tissue through surfaces (954, 964), thereby sealing/coagulating the tissue along a region between the tissue contact points of surfaces (954, 964). As with the other variations described herein, it will be appreciated that energy may be supplied via control (30) and power source (32) as shown in FIG. 1. However other suitable power sources may be used as would be apparent to one of ordinary skill in the art in view of the teachings herein. It should also be understood that surfaces (954, 964, 974, 984) may be used to seal/coagulate tissue in instances where neither surfaces (952, 962, 972, 982) are used to weld/seal/coagulate tissue nor an I-beam knife (770) (or other feature) is used to sever tissue.

FIGS. 21-22 depict another exemplary set of jaws (1042, 1044) that are operable to selectively either weld/seal/coagulate tissue between jaws (1042, 1044) or seal/coagulate tissue that is external to jaws (1042, 1044). Jaws (1042, 1044) of this example are substantially similar to jaws (842, 844) described above, except that jaws (1042, 1044) of this example include exterior electrode strips (1066, 1068). Jaws (1042, 1044) of this example have respective plastic, electrically insulative portions (1052, 1054), respective positive temperature coefficient (PTC) thermistor polymer portions (1056, 1058), and respective interior electrode strips (1062, 1064). Insulative portions (1052, 1054) are arranged on opposite sides of a vertical plane passing through the center of jaws (1042, 1044). PTC thermistor portions (1056, 1058) are also arranged on opposite sides of a vertical plane passing through the center of jaws (1042, 1044). Interior electrode strip (1062) is secured to the top of insulative portion (1052); while interior electrode strip (1064) is secured to the top of insulative portion (1054). Various suitable ways in which the above-described components may be secured together will be apparent to those of ordinary skill in the art in view of the teachings herein.

It should be understood that PTC thermistor polymer portions (1056, 1058) may be electrically conductive when the temperature of PTC thermistor polymer portions (1056, 1058) is below a certain threshold; while PTC thermistor polymer portions (1056, 1058) may be electrically insulative when the temperature of PTC thermistor polymer portions (1056, 1058) is above a certain threshold. Thus, when the temperature of PTC thermistor polymer portions (1056, 1058) is below a certain threshold and RF energy is applied to jaws, RF energy may flow through tissue (not shown) from PTC thermistor polymer portion (1056) to PTC thermistor polymer portion (1058). It should be understood that this RF energy flow path through tissue is oblique, similar to the oblique RF energy path described above with respect to jaws (42, 44). RF energy may also flow through the tissue from electrode strip (1062) to electrode strip (1064), which is another oblique path. Furthermore, RF energy may also flow through the tissue from electrode strip (1062) to PTC thermistor polymer portion (1058); and from electrode strip (1064) to PTC thermistor polymer portion (1056). It should therefore be understood that RF energy may flow through tissue along four different paths when PTC thermistor polymer portions (1056, 1058) are in electrically conductive states.

Once the temperature of PTC thermistor polymer portions (1056, 1058) exceeds the threshold, PTC thermistor polymer portions (1056, 1058) become electrically insulative. At that stage, to the extent that RF energy continues to flow through the tissue at all, the RF energy only flows through the tissue from electrode strip (1062) to electrode strip (1064). In some other versions, PTC thermistor polymer portions (1056, 1058) are substituted with insulative plastic. In such versions, RF energy may simply flow through the tissue from electrode strip (1062) to electrode strip (1064), again along an oblique path. As another merely illustrative example, electrode strips (1062, 1064) may be omitted and RF energy may flow through tissue from PTC thermistor polymer portion (1056) to PTC thermistor polymer portion (1058) until the temperature exceeds a threshold, at which point RF energy stops flowing through the tissue.

As noted above, I-beam knife (770) of the present example includes a pair of outwardly directed upper transverse pins (772) and a pair of outwardly directed lower transverse pins (774). Pins (772) are disposed in a recess (1071) defined in jaw (1044); while pins (774) are disposed in a recess (1070) defined in jaw (1042). I-beam knife (770) is operable to translate longitudinally through jaws (1042, 1044). In use, jaws (1042, 1044) may be closed on tissue to compress the tissue and then weld/seal/coagulate the tissue as described above. Then, I-beam knife (770) may be driven distally to cut the tissue. Again, several merely illustrative examples of how I-beam knife (770) may be driven distally will be described in greater detail below; while further examples will be apparent to those of ordinary skill in the art in view of the teachings herein. In the event that jaws (1042, 1044) are not fully compressing the tissue when I-beam knife (770) is driven distally, pins (772, 774) may act as cams against jaws (1042, 1044) to thereby drive jaws (1042, 1044) to fully compressed positions.

Before or after jaws (1042, 1044) are used to weld/seal/coagulate tissue captured between jaws (1042, 1044), and perhaps before or after tissue is severed by an I-beam knife (770), the user may rotate jaws (1042, 1044) approximately ninety degrees about their longitudinal axis and press the exterior of jaws (1042, 1044) against tissue to seal/coagulate the tissue. In particular, the user may press exterior electrode strips (1066, 1068) against tissue, which may be energized with bipolar RF energy to seal/coagulate the tissue along a region between the tissue contact points of exterior electrode strips (1066, 1068). It should also be understood that exterior electrode strips (1066, 1068) may be used to seal/coagulate tissue in instances where neither any interior portions of jaws (1042, 1044) are used to weld/seal/coagulate tissue nor an I-beam knife (770) (or other feature) is used to sever tissue.

V. Exemplary Jaws with Staggered Teeth

In some instances, it may be desirable to have jaws with teeth with positioning that alternates along the length of the jaws. Such configurations may provide enhanced capabilities for grasping and holding tissue between the jaws. Such configurations may also provide enhanced tissue welding/sealing/coagulating capabilities. In addition or in the alternative, such configurations may facilitate severing of tissue between jaws, such as by reducing the force needed in squeezing handles (12, 14) to sever tissue. FIGS. 23-26 show an exemplary variation of jaws (1142, 1144) having teeth (1152, 1154) with positions that alternate along the length of jaws (1142, 1144). In particular, teeth (1152) are asymmetrically positioned opposing sides of a longitudinal line extending along the center of lower jaw (1142). Teeth (1154) are asymmetrically positioned on opposing sides of a longitudinal line extending along the center of upper jaw (1142). A series of recesses (1156) separate teeth (1152) along lower jaw (1142), creating a checkerboard type of pattern; while a similar series of recesses (1158) separate teeth (1154) along upper jaw (1144), also creating a checkerboard type of pattern.

As best seen in FIGS. 25-26, the spacing of teeth (1152, 1154) and recesses (1156, 1158) is configured such that teeth (1152) nest in complementary recesses (1158), and such that teeth (1154) nest in complementary recesses (1156), when jaws (1142, 1144) are closed together. In the present example, each tooth (1152, 1154) comprises an electrically insulative material, while recesses (1156, 1158) are present electrically conductive surfaces. For instance, jaws (1142, 1144) may be generally formed of an electrically conductive material (e.g., metal), with teeth (1152, 1154) being formed as unitary features of jaws (1142, 1144), and with teeth (1152, 1154) being coated in an electrically insulative material (e.g., plastic) leaving the conductive material of recesses (1156, 1158) exposed. As yet another merely illustrative example, jaws (1142, 1144) may be generally formed of an electrically conductive material (e.g., metal) presenting flat inner jaw surfaces, with teeth (1152, 1154) being formed entirely of electrically insulative material (e.g., plastic) then secured to the flat inner surfaces of jaws (1142, 1144), leaving the conductive material of recesses (1156, 1158) exposed. Other suitable ways in which teeth (1152, 1154) may be formed will be apparent to those of ordinary skill in the art in view of the teachings herein. It should also be understood that one or more edges of each tooth (1152, 1154) includes a pressure concentration feature, such as a ridge, hump, raised edge, etc.

As also seen in FIGS. 25-26, the lateral interior faces (1153, 1155) of teeth (1152, 1154) are obliquely angled, similar to regions (62, 72) described above. Recess (1156) surfaces of lower jaw (1142) have a negative bias while recess (1158) surfaces of upper jaw (1144) have a positive bias. This configuration provides an oblique lateral path for RF energy traveling from recess (1156) surface to the laterally associated recess (1158) surface through tissue clamped between jaws (1142, 1144). In addition, the distal faces (1172) of teeth (1152) and the proximal faces (1174) of teeth (1152), as well as the distal faces (1176) of teeth (1154) and the proximal faces (1178) of teeth (1154), are all obliquely angled. These configurations thus provide an oblique longitudinal path for RF energy traveling from recess (1156) surface to the longitudinally associated recess (1158) surfaces through tissue clamped between jaws (1142, 1144). In other words, RF energy may travel distally/proximally along oblique paths between recess (1156, 1158) surfaces and laterally along oblique paths between recess (1156, 1158) surfaces. In some other versions, teeth (1152, 1154) are spaced such that greater gaps are located between faces (1153, 1155), between faces (1172, 1178), and/or between faces (1174, 1176) when jaws (1142, 1144) are closed together, such that corresponding faces (1153, 1155), faces (1172, 1178), and/or faces (1174, 1176) would not tend to contact each other when jaws (1142, 1144) are closed together. Other suitable configurations and arrangements for teeth (1152, 1154) will be apparent to those of ordinary skill in the art in view of the teachings herein.

Jaws (1142, 1144) further comprise a distal tooth (1162) and distal tooth nest (1164). Tooth (1162) has a triangular profile in this example and fits within tooth nest (1164) when jaws (1142, 1144) are closed together, as shown in FIG. 24. In some instances, the combination of distal tooth (1162) and distal tooth nest (1164) may provide greater tissue gripping control with jaws (1142, 1144) and/or fine tearing dissection capabilities, similar to a Maryland dissector, etc. In addition or in the alternative, the combination of distal tooth (1162) and distal tooth nest (1164) may provide opposed electrode fine cautery (e.g., as contrasted to offset electrode gross transaction cautery provided by teeth (1152, 1154). Of course, distal tooth (1162) and distal tooth nest (1164) may have any other suitable configurations and capabilities. It should also be understood that distal tooth (1162) and/or distal tooth nest (1164) may simply be omitted, if desired.

VI. Exemplary Jaws with External Blunt Dissection Features

In some settings, a user may wish to use jaws (42, 44) to perform blunt dissections. For instance, a user may wish to drive jaws (42, 44) into tissue to separate one tissue portion from another tissue portion, within the same anatomical structure. As another example, a user may wish to drive jaws (42, 44) between one anatomical structure and an adjacent anatomical structure, to effectively peel away the tissue of one anatomical structure from the adjacent anatomical structure. Such blunt dissection operations may be performed with jaws (42, 44) being kept closed together. In addition, the user may perform blunt dissection by opening jaws (42, 44) within or between tissue, such that opening jaws (42, 44) may assist in separating tissue and/or anatomical structures. FIGS. 27-28 show exemplary features that may be provided to enhance blunt dissection capabilities of jaws (42, 44). Other examples of blunt dissection features will be apparent to those of ordinary skill in the art in view of the teachings herein. It should be understood that the blunt dissection features described herein may be readily applied to any of the jaws described herein. Furthermore, it should be understood that the blunt dissection features described herein may be used before or after the jaws are used to weld/seal/coagulate and/or sever tissue.

FIG. 27 shows a pair of jaws (1242, 1244) having respective sets of exemplary exterior lateral wedge features (1246, 1248). Lateral wedge features (1246, 1248) are formed as angled fins that define respective laterally opening angles. These angles all have respective vertexes that are positioned along an axis that is parallel to and laterally offset from the longitudinal axis of jaws (1242, 1244). Lateral wedge features (1246, 1248) may enhance blunt dissection capabilities when jaws (1242, 1244) are moved into/between tissue along a path of movement that is transverse to the longitudinal axis of jaws (1242, 1244). When jaws (1242, 1244) are positioned in tissue or between tissue structures and jaws (1242, 1244) are then opened while being held laterally/longitudinally stationary, lateral wedge features (1246, 1248) may substantially prevent jaws (1242, 1244) from slipping out of position relative to the tissue. Lateral wedge features (1248) may also be used to scrape tissue and/or perform other acts. Furthermore, lateral wedge features (1246, 1248) may be used to manipulate tissue when jaws (1242, 1244) are moved into/between tissue along a path of movement that is parallel to the longitudinal axis of jaws (1242, 1244). Other suitable variations and uses of lateral wedge features (1246, 1248) will be apparent to those of ordinary skill in the art in view of the teachings herein.

FIG. 28 shows a pair of jaws (1342, 1344) where upper jaw (1344) has an exterior upper crest (1348) extending longitudinally along the outer surface of upper jaw (1344). While not shown, it should be understood that lower jaw (1342) may also have a crest. Crest (1348) extends along the full length of upper jaw (1344) in this example, though it should be understood that crest (1348) may extend along any suitable length. In addition, crest (1348) extends along a path that is parallel to the longitudinal axis of jaws (1342, 1344), though crest (1348) may alternatively extend along any other suitable path. Crest (1348) is pointed in the present example, though crest (1348) may instead be rounded or have any other suitable configuration. Other suitable configurations for crest (1348) will be apparent to those of ordinary skill in the art in view of the teachings herein. It should be understood that crest (1348) may provide a pressure concentration region against tissue, such as by concentrating a substantial amount of pressure applied by the exterior of jaws (1342, 1344) along crest (1348). Crest (1348) may also assist in maintaining the lateral positioning of jaws (1342, 1344) relative to tissue when jaws (1342, 1344) are opened while being disposed in tissue or between tissue structures. Crest (1348) may also be used to scrape tissue and/or perform other acts. Other suitable variations and uses of crest (1348) will be apparent to those of ordinary skill in the art in view of the teachings herein.

FIG. 29 shows a pair of jaws (1442, 1444) having respective sets of exemplary exterior sawtooth features (1446, 1448). Sawtooth features (1446, 1448) are formed as angled teeth that define respective proximally opening angles. These angles all have respective vertexes that are positioned along the longitudinal axis of jaws (1442, 1444). Sawtooth features (1446, 1448) may enhance blunt dissection capabilities when jaws (1442, 1444) are moved into/between tissue along a path of movement that is parallel to the longitudinal axis of jaws (1442, 1444). When jaws (1442, 1444) are positioned in tissue or between tissue structures and jaws (1442, 1444) are then opened while being held laterally/longitudinally stationary, sawtooth features (1446, 1448) may substantially prevent jaws (1442, 1444) from slipping out of position relative to the tissue. Sawtooth features (1446, 1448) may also be used to scrape tissue and/or perform other acts. Furthermore, sawtooth features (1446, 1448) may be used to manipulate tissue when jaws (1442, 1444) are moved into/between tissue along a path of movement that is transverse to the longitudinal axis of jaws (1442, 1444). Other suitable variations and uses of sawtooth features (1446, 1448) will be apparent to those of ordinary skill in the art in view of the teachings herein.

VII. Exemplary Forceps Controls

As noted above with respect to FIGS. 1-3, a single button (16) may be used to selectively activate electrode surfaces to deliver RF energy to tissue clamped between jaws (42, 44). In some such versions, the single button (16) simply turns the RF energy on, at one set of operational parameters (e.g., frequency, amplitude, etc.), when button (16) is actuated. The RF energy simply turns off when button (16) is released. In some instances, it may be desirable to provide more than one set of parameters for the RF energy, based on the particular operation to be performed. For instance, tissue welding operations may warrant a first combination of RF energy parameters (e.g., lower amplitude, etc.) while tissue cutting operations may warrant a second combination of RF energy parameters (e.g., higher amplitude, etc.). To that end, it may be desirable to provide one or more user input features that are operable to selectively activate RF energy at the energy parameter combinations that are best suited to the task at hand. Several merely illustrative examples of such user input features will be described in greater detail below, while additional examples will be apparent to those of ordinary skill in the art in view of the teachings herein. It should be understood that the below teachings may be readily combined with any of the above teachings in numerous permutations.

FIG. 30 shows an exemplary forceps instrument (1510) that includes a pair of jaws (1542, 1544) and a pair of handles (1512, 1514) that provide a scissor grip. Lower handle (1512) includes a pair of textured trigger buttons (1516, 1518). Proximal trigger button (1516) is operable to activate electrode surfaces of jaws (1542, 1544) with RF energy at a first combination of operational parameters; while distal trigger button (1518) is operable to activate electrode surfaces of jaws (1542, 1544) with RF energy at a second combination of operational parameters. By way of example only, proximal trigger button (1516) may activate electrode surfaces of jaws (1542, 1544) with RF energy at a combination of parameters associated with tissue welding/sealing/coagulating; while distal trigger button (1518) may activate electrode surfaces of jaws (1542, 1544) with RF energy at a combination of parameters associated with tissue cutting. As shown, proximal trigger button (1516) is larger than distal trigger button (1518), providing the user with the ability to differentiate between trigger buttons (1516, 1518) based solely on the sense of touch, without having to look at trigger buttons (1516, 1518).

Of course, trigger buttons (1516, 1518) may take a variety of alternative forms as will be apparent to those of ordinary skill in the art in view of the teachings herein. For instance, trigger buttons (1516, 1518) may be configured as proximally and distally positioned flexible bubbles, buttons having differing sizes, buttons having differing shapes, a slider switch, a switch having a plurality of movable positions, buttons having different colors, or any other suitable variations as would be apparent to one of ordinary skill in the art in view of the teachings herein. It should also be understood that instrument (1510) may have more than two trigger buttons (e.g., to provide selective activation of more than two combinations of RF energy parameters, etc.). Furthermore, distal trigger button (1518) may be operable to actuate an I-beam knife or other movable cutting feature, in addition to or in lieu of activating RF energy at a second combination of parameters.

Figure 31:
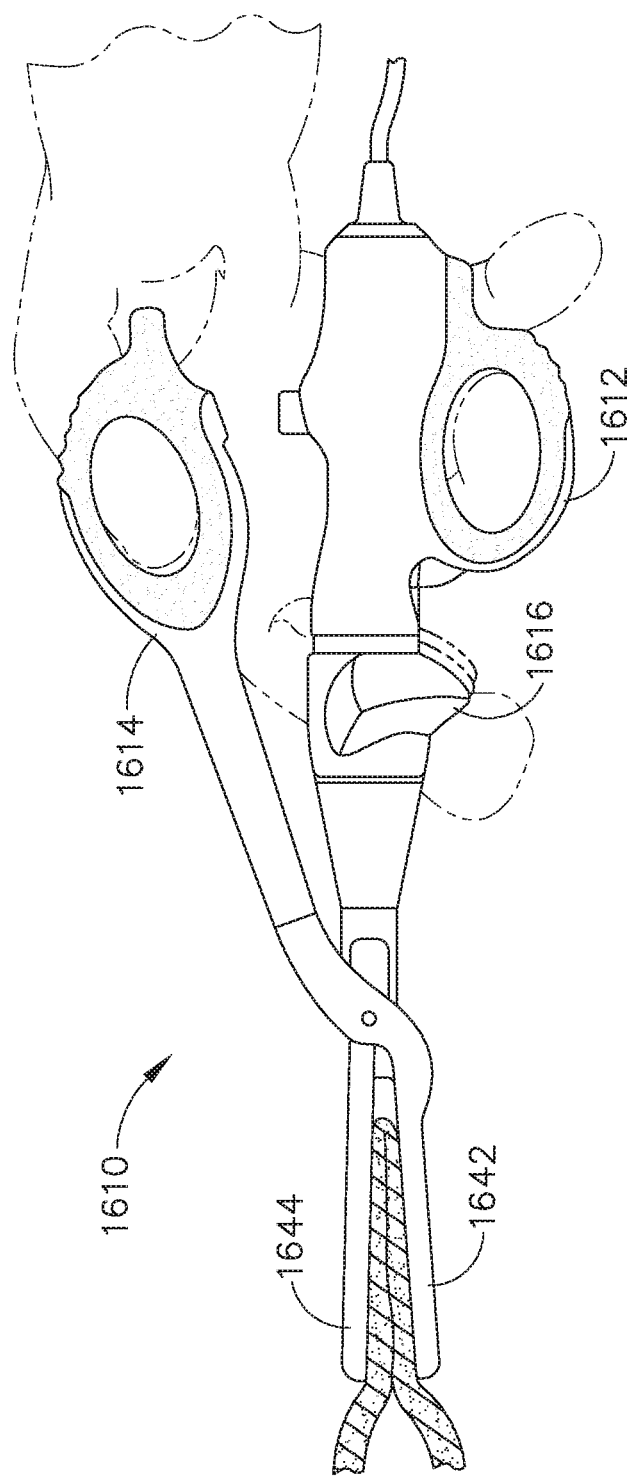
FIG. 31 depicts a side view of an exemplary alternative forceps instrument with a two stage actuation trigger.

FIG. 31 shows an exemplary forceps instrument (1610) that includes a pair of jaws (1642, 1644), a pair of handles (1612, 1614) that provide a scissor grip, and a single textured trigger button (1616). Trigger button (1616) is movable proximally through a progressive series of two ranges of motion in two separate stages. In particular, trigger button (1616) is movable proximally from a distal position to a transition position. At this stage, trigger button (1616) activates electrode surfaces of jaws (1642, 1644) with RF energy at a first combination of operational parameters. By way of example only, this first combination of operational parameters may be associated with tissue welding/sealing/coagulating. Trigger button (1616) is further movable proximally from the transition position to a proximal position. At this stage, trigger button (1616) activates electrode surfaces of jaws (1642, 1644) with RF energy at a second combination of operational parameters. By way of example only, this second combination of operational parameters may be associated with tissue cutting.

It should be understood that a detent and/or other feature(s) may be used to provide the user with feedback indicating the completion of the first range of motion (i.e., indicating that the user has reached the transition position). Such feedback features may provide tactile and/or audible feedback to the user. In addition or in the alternative, a light or other form of visual feedback may be used as a form of feedback to the user. Of course, trigger button (1616) may take a variety of alternative forms as will be apparent to those of ordinary skill in the art in view of the teachings herein. It should also be understood that trigger button (1616) may have more than two activation positions within its range of motion (e.g., to provide selective activation of more than two combinations of RF energy parameters, etc.). Furthermore, the proximal position of trigger button (1616) may actuate an I-beam knife or other movable cutting feature, in addition to or in lieu of activating RF energy at a second combination of parameters.

Figure 32:
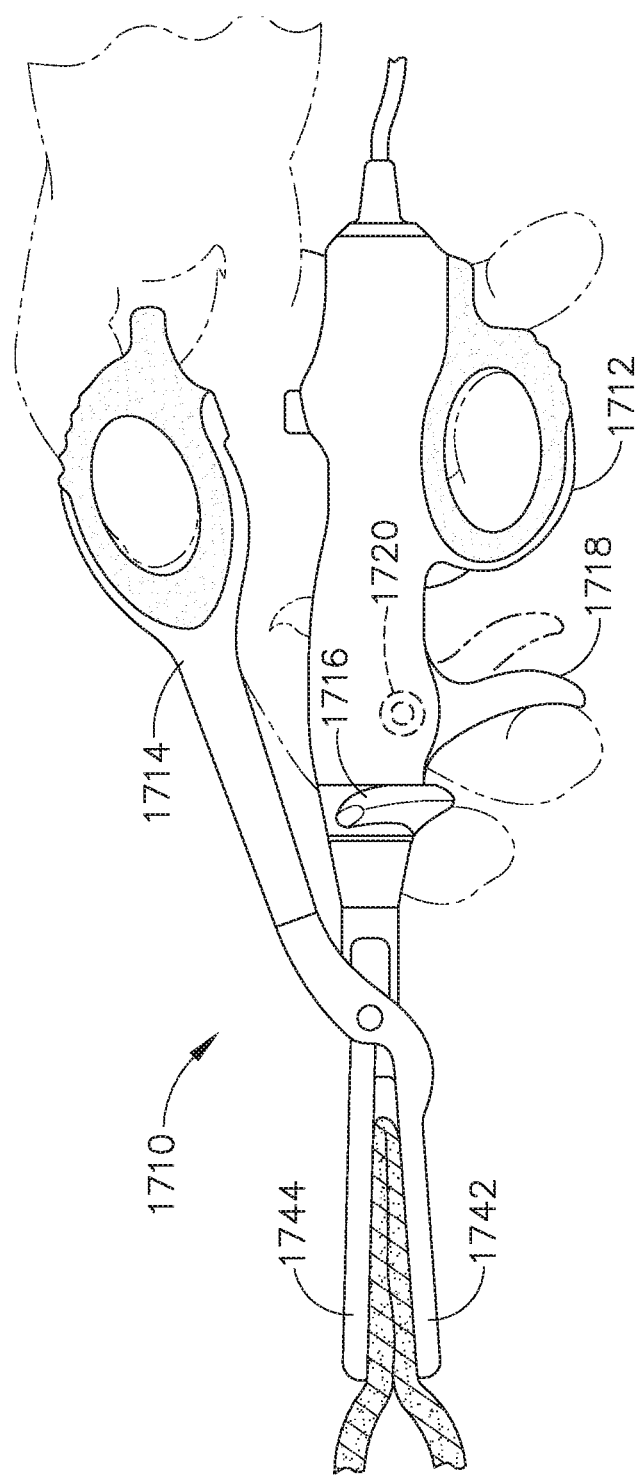
FIG. 32 depicts a side view of an exemplary alternative forceps instrument with an energizing button and a cutting trigger.

It should be understood that instruments (1510, 1610) are configured such that a user may readily perform separate acts of tissue welding/sealing/coagulating and cutting using the same single finger of the hand that grips instrument (1510, 1610). In some instances, it may be desirable to use separate fingers to perform the separate acts of welding/sealing/coagulating and cutting. FIG. 32 shows an exemplary forceps instrument (1710) that facilitates the use of separate fingers to perform the separate acts of welding/sealing/coagulating and cutting, though it should be understood that a user may nevertheless use the same single finger to perform the separate acts of welding/sealing/coagulating and cutting with instrument (1710), if desired. Instrument (1710) of this example includes a pair of jaws (1742, 1744), a pair of handles (1712, 1714) that provide a scissor grip, a distal trigger button (1716), and a proximal pivoting trigger (1718). As shown, distal trigger button (1716) is positioned to be actuated by the user's index finger; while proximal pivoting trigger (1718) is positioned to be actuated by the middle finger of the same hand. Proximal pivoting trigger (1718) is configured to pivot relative to handle (1712) at a pivotal coupling (1720).

Distal trigger button (1716) is operable to activate electrode surfaces of jaws (1742, 1744) with RF energy at a first combination of operational parameters; while proximal pivoting trigger (1718) is operable to activate electrode surfaces of jaws (1742, 1744) with RF energy at a second combination of operational parameters. By way of example only, distal trigger button (1716) may activate electrode surfaces of jaws (1742, 1744) with RF energy at a combination of parameters associated with tissue welding/sealing/coagulating; while proximal pivoting trigger (1718) may activate electrode surfaces of jaws (1742, 1744) with RF energy at a combination of parameters associated with tissue cutting. It should be understood that proximal pivoting trigger (1718) may be operable to actuate an I-beam knife or other movable cutting feature, in addition to or in lieu of activating RF energy at a second combination of parameters.

Figure 33A:
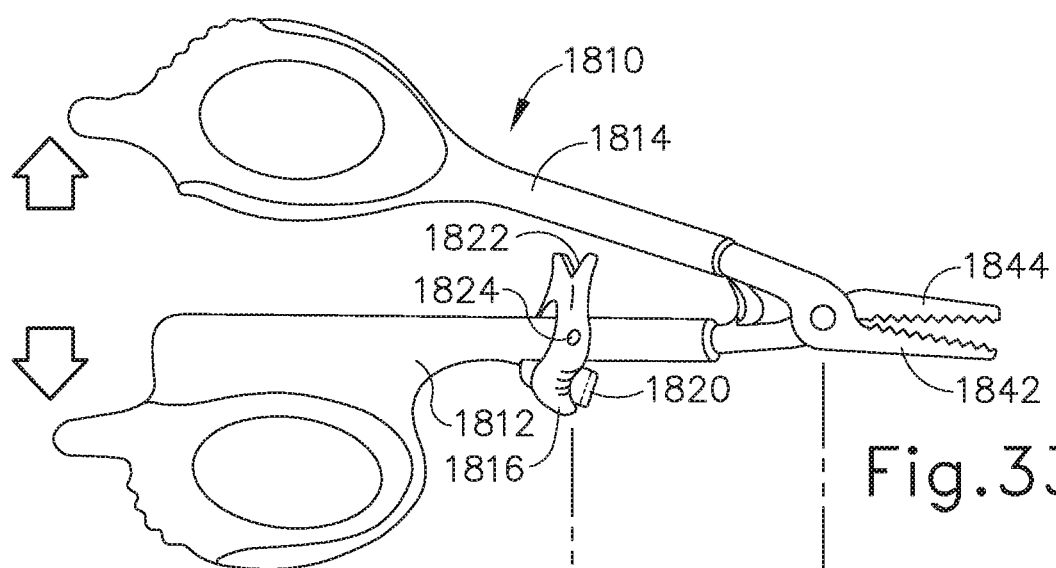
FIG. 33A depicts a side view of an exemplary alternative forceps instrument with a knife lock out trigger integrated with an energizing button.
Figure 33B:
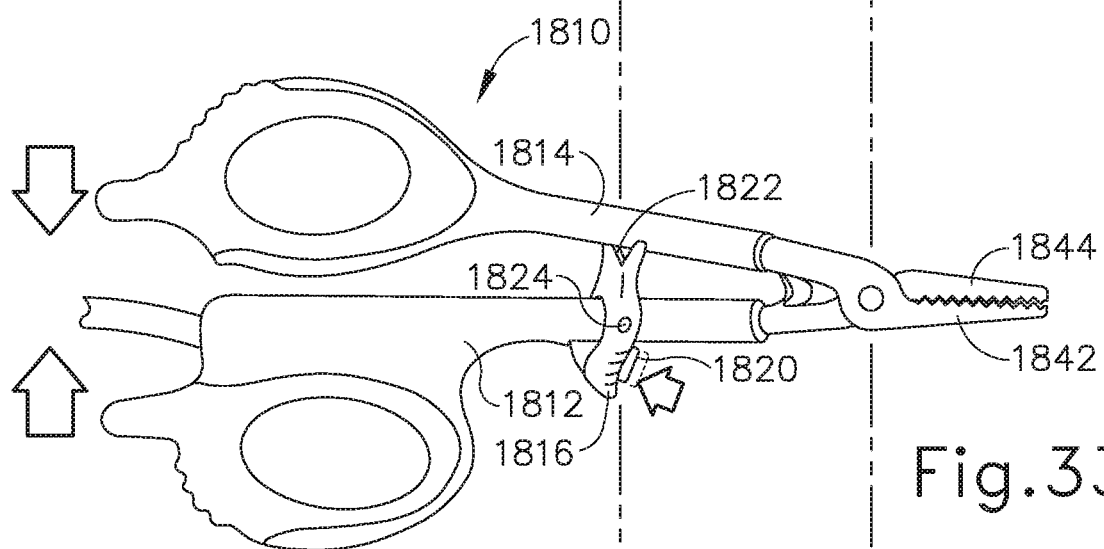
FIG. 33B depicts a side view of the forceps instrument of FIG. 33A with the energizing button pressed.
Figure 33C:
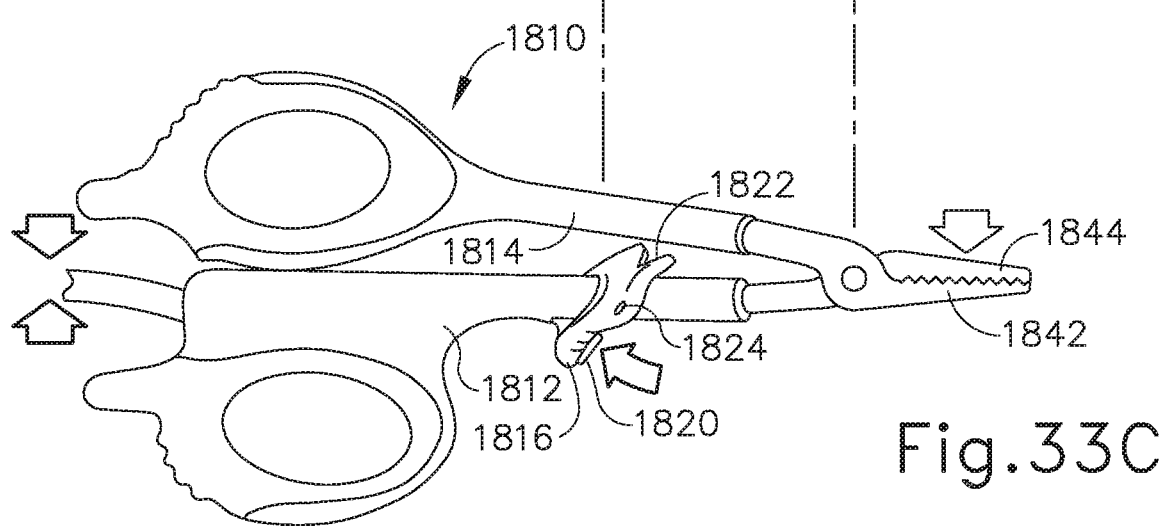
FIG. 33C depicts a side view of the forceps instrument of FIG. 33A with the energizing button pressed and the lockout trigger pulled.

FIGS. 33A-33C show an exemplary forceps instrument (1810) with handles (1812, 1814) and jaws (1842, 1844) that are operable to clamp and seal tissue. Instrument (1810) of this example further comprises a trigger member (1816) that is operable to control energization of jaws (1842, 1844) and that is also operable to restrict movement of jaws (1842, 1844). Trigger member (1816) is pivotally coupled with handle (1812) by a pin (1824); and is pivotable relative to handle (1812) about pin (1824). Trigger member (1816) also comprises a button (1820) that may be pressed by a user. Button (1820) is operable to activate electrode surfaces of jaws (1842, 1844) with RF energy as described above, to thereby weld/seal/coagulate tissue captured between jaws (1842, 1844).

An upper portion of trigger member (1816) includes a seat (1822) that is shaped to complement the underside of upper handle (1814). Trigger member (1816) is pivotable about pin (1824) through the range of motion depicted in FIGS. 33A-33C. In particular, when trigger member (1816) is in the generally upright position, trigger member (1816) enables handles (1812, 1814) to be partially pivoted toward each other as shown in the transition from FIG. 33A to FIG. 33B. This provides partial closure of jaws (1842, 1844). When handles (1812, 1814) and jaws (1842, 1844) reach the position shown in FIG. 33B, handle (1814) is received in seat (1822) and trigger member (1816) blocks further pivoting of handles (1812, 1814) and jaws (1842, 1844). The length of trigger member (1816) is selected to provide a particular gap between jaws (1842, 1844) at this stage. This gap is associated with a degree of tissue compression associated with tissue welding/sealing/coagulating. For instance, this gap may be similar to the distance between jaws (342, 344) shown in FIG. 10B. At this stage, the user may depress button (1820) to activate electrode surfaces of jaws (1842, 1844) with RF energy to thereby weld/seal/coagulate tissue captured between jaws (1842, 1844).

After the user has depressed button (1820) to activate electrode surfaces of jaws (1842, 1844) with RF energy as described above, and the tissue between jaws has been sufficiently welded/sealed/coagulated, the user may press on trigger member (1816) with additional force to pivot trigger member (1816) from the position shown in FIG. 33B to the position shown in FIG. 33C. This moves seat (1822) out of engagement with upper handle (1814), providing clearance for handles (1812, 1814) to be drawn closer together, thereby enabling jaws (1842, 1844) to be driven further toward each other. In particular, the user may now drive jaws (1842, 1844) toward each other with sufficient distance and force to sever tissue captured between jaws (1842, 1844). For instance, with trigger member (1816) pivoted from the position shown in FIG. 33B to the position shown in FIG. 33C, jaws (1842, 1844) may reach a position similar to the positioning of jaws (342, 344) shown in FIG. 10C. It should be understood from the foregoing that trigger member (1816) may be used to ensure that tissue is suitably welded/sealed/coagulated before the tissue is cut. In other words, the temporary arrest of upper handle (1814) by trigger member (1816) may remind the user to activate button (1820), to thereby weld/seal/coagulate the tissue, before completing the act of cutting the tissue. In the present example, trigger member (1816) is resiliently biased to the position shown in FIG. 33A, to thereby block full closure of jaws (1842, 1844) by default.

Figure 34A:
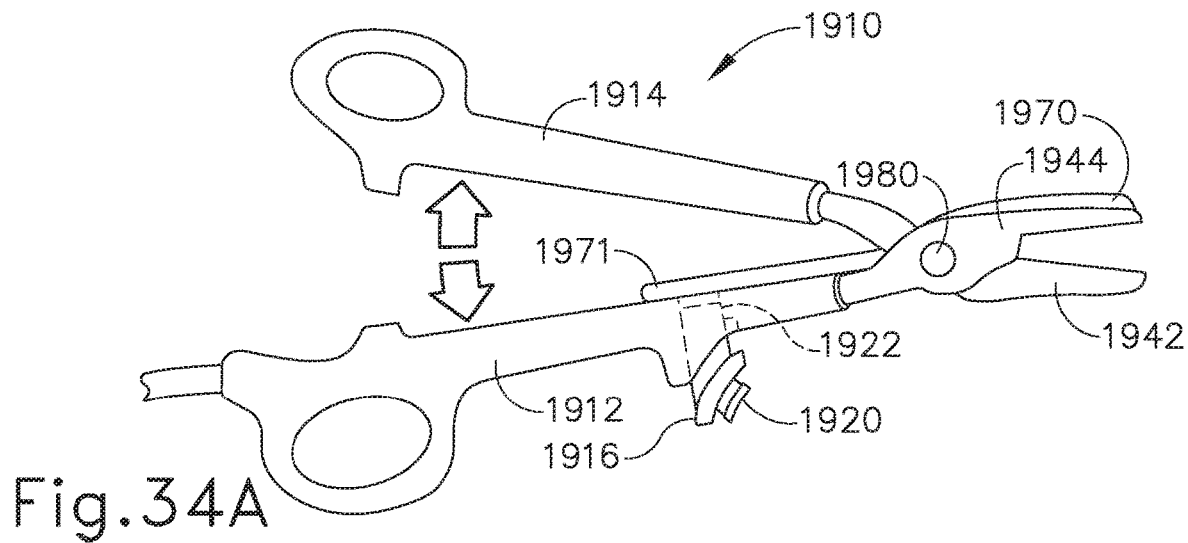
FIG. 34A depicts a side view of an exemplary alternative forceps instrument with a knife lock out trigger integrated with an energizing button.
Figure 34B:
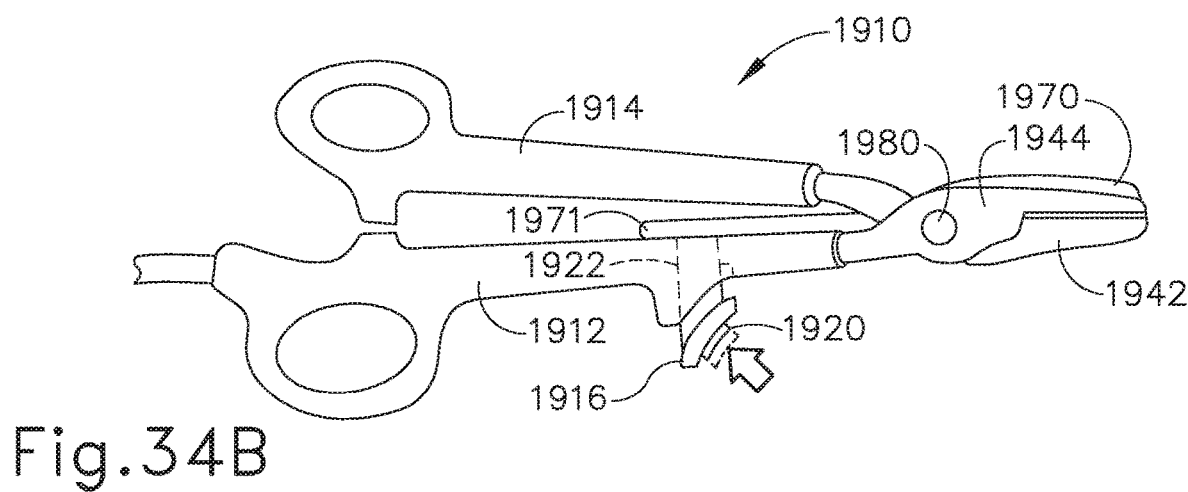
FIG. 34B depicts a side view of the forceps instrument of FIG. 34A with the energizing button pressed.
Figure 34C:
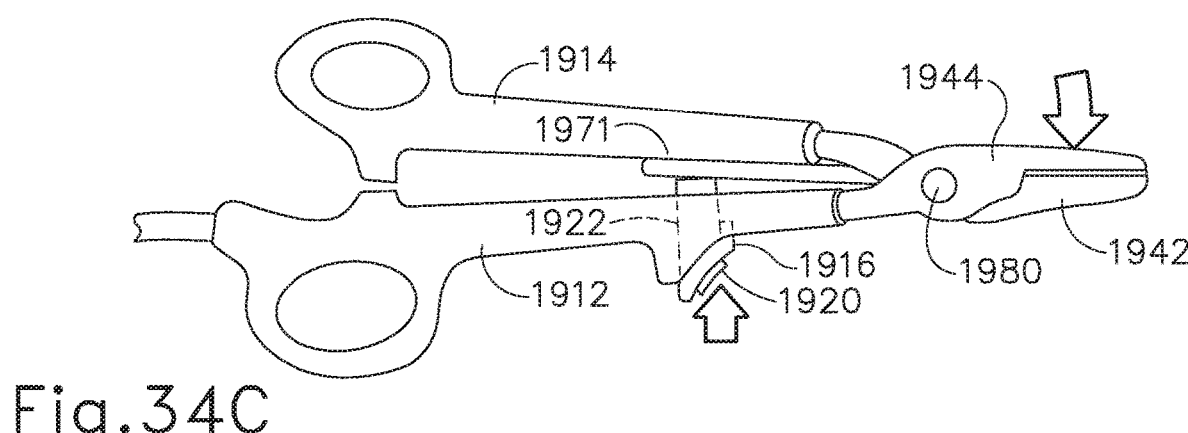
FIG. 34C depicts a side view of the forceps instrument of FIG. 34A with the energizing button pressed and the lockout trigger pulled.

FIGS. 34A-34C show yet another exemplary forceps instrument (1910) having jaws (1942, 1944) and handles (1912, 1914). Instrument (1910) further comprises a trigger (1916) with a button (1920). Trigger (1916) is positioned within a slot (1922) of handle (1912) such that trigger (1916) is slidable within slot (1922). FIG. 34B shows handles (1912, 1914) urged toward each other to close jaws (1942, 1944); and button (1920) depressed. Button (1920) is operable to activate electrode surfaces of jaws (1942, 1944) with RF energy, to weld/seal/coagulate tissue captured between jaws (1942), when button (1920) is depressed as shown in FIG. 34B. Instrument (1910) of this example further comprises a pivoting knife (1970). Knife (1970) comprises a blade that is configured to pass through a longitudinally extending slot formed in upper jaw (1944), such that knife (1970) is pivotable from an upper position (FIG. 34B) to a lower position (FIG. 34C). Knife (1970) is pivotally coupled at the same joint (1980) that couples jaws (1942, 1944) and handles (1912, 1914) in this example, though it should be understood that a separate coupling may be used.

The proximal end of knife (1970) presents a lever arm (1971) that is engaged by trigger (1916). In particular, as trigger (1916) is pushed upwardly relative to handle (1912), trigger (1916) pushes upwardly on lever arm (1971). Due to the pivot provided at joint (1980), this upward movement of lever arm (1971) provides downward movement of the blade of knife (1970) as seen in the transition from FIG. 34B to FIG. 34C. This downward movement of the blade of knife (1970) severs tissue captured between jaws (1942, 1944). In some versions, lower jaw (1942) provides a cutting board against which the blade of knife (1970) acts in order to sever tissue captured between jaws (1942, 1944). In the present example, spring biases are selected such that the amount of force required to move button (1920) from the position shown in FIG. 34A to the position shown in FIG. 34B is substantially less than the amount of force required to move trigger (1916) from the position shown in FIGS. 34A-34B to the position shown in FIG. 34C. Thus, when a user presses upwardly on button (1920) and trigger (1916), button (1920) will be fully depressed before trigger (1916) moves within slot (1922), such that the electrode surfaces of jaws (1942, 1944) will provide bipolar RF energy to tissue captured between jaws (1942, 1944) before knife (1970) severs that tissue.

In the example shown in FIGS. 34A-34C, knife (1970) is actuated by pushing trigger (1916) along a path that is generally transverse to handle (1912). In some other versions, a trigger is pushed along a path that is generally parallel to a handle in order to actuate a knife. For instance, FIGS. 35-36B show an exemplary forceps instrument (2010) with a pair of handles (2012, 2014), a pair of jaws (2042, 2044), and a longitudinally sliding trigger (2016). Instrument (2010) also includes a knife (2070) having a sharp edge (2071) that is operable to sever tissue clamped between jaws (2042, 2044). Knife (2070) of this example further includes a pair of laterally extending pins (2022) and a proximal engagement leg (2024). Pins (2022) are disposed in obliquely angled slots (2020) that are formed in upper jaw (2044). The configuration of slots (2020) and the relationship between slots (2020) and pins (2022) provide movement of knife (2070) along a vertical plane when knife (2070) is driven distally/proximally. In particular, knife (2070) will move downwardly when knife (2070) moves from a distal position to a proximal position; and will move upwardly when knife (2070) moves from a proximal position to a distal position. FIG. 36A shows knife (2070) in an upper, distal position. FIG. 36B shows knife (2070) in a lower, proximal position, which is where knife (2070) would be severing tissue captured between jaws (2042, 2044).

As shown in FIG. 35, proximal engagement leg (2024) of knife (2070) is coupled with trigger (2016). Trigger (2016) is slidable proximally relative to handle (2012). Thus, a user may pull trigger (2016) proximally relative to handle (2012) to pull knife (2070) proximally, thereby driving knife (2070) downwardly to sever tissue. Trigger (2016) of the present example is resiliently biased distally, thereby biasing knife (2070) to the upper position shown in FIG. 36A. It should be understood that trigger (2016) may include an activation feature similar to button (1920) described above, to selectively activate electrode surfaces of jaws (2042, 2044) with bipolar RF energy. Such a button may be configured for staged actuation with trigger (2016) such that RF energy is applied to tissue before the tissue is severed by knife (2070).

FIGS. 35-36B show an exemplary alternative version of a forceps instrument (2010) having an alternative way of using a knife (2070) to cut tissue clamped between jaws (2042, 2044). Jaw (2044) comprises a cam feature (2022) operable to engage cam slots (2020) of knife (2070). Knife (2070) has a shape that generally follows the contour of jaw (2044) in an angular fashion. Knife (2070) further comprises an engagement leg (2024) operable to engage trigger (2016). In particular, trigger (2016) may be actuated by a user to move knife (2070) from the position shown in FIG. 36A to the position of knife (2070) shown in FIG. 36B. Trigger (2016) moves proximally against engagement leg (2024) which pulls knife (2070) proximally. As knife (2070) moves proximally, knife (2070) also slices downward such that any tissue between jaws (2042, 2044) would be cut by knife (2070). It will be understood that in some versions, knife (2070) may be spring biased to assume the position shown in FIG. 36A.

Figure 37:
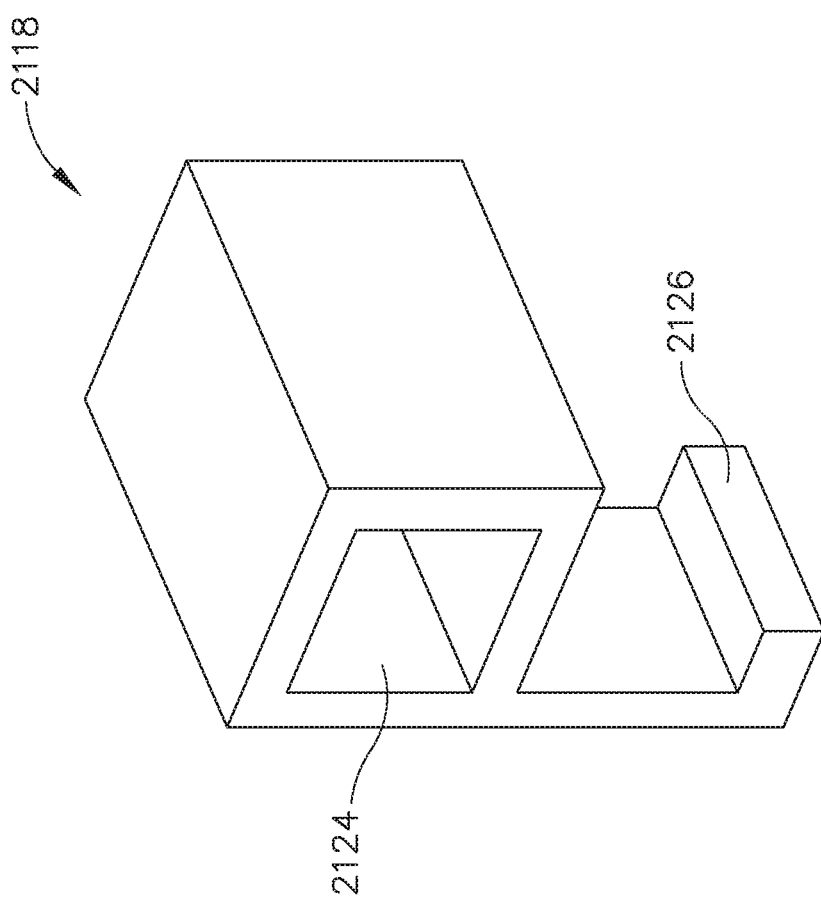
FIG. 37 depicts a perspective view of a coupler of an exemplary alternative forceps instrument.
Figure 38:
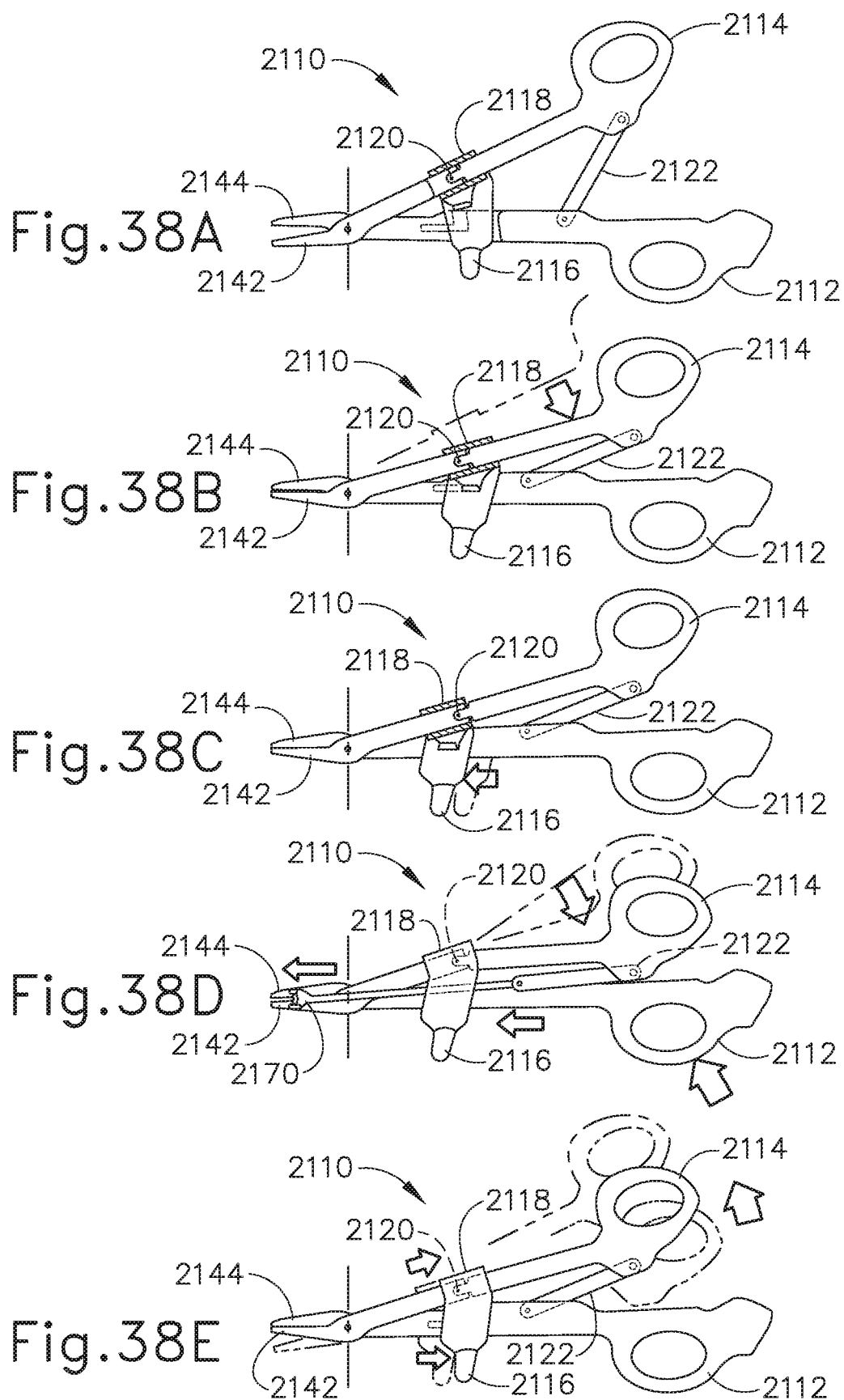
FIG. 38A depicts a side view of an exemplary forceps instrument incorporating the coupler of FIG. 37 with jaws open.
FIG. 38B depicts a side view of the forceps instrument of FIG. 38A with the jaws clamped.
FIG. 38C depicts a side view of the forceps instrument of FIG. 38A with the jaws energized.
FIG. 38D depicts a side view of the forceps instrument of FIG. 38A with a knife advancing.
FIG. 38E depicts a side view of the forceps instrument of FIG. 38A with the jaws released.

FIGS. 37-38E show another exemplary alternative version of a forceps instrument (2110) along with features to energize and cut tissue. Instrument (2110) of this example comprises a pair of handles (2112, 2114) and a corresponding pair of jaws (2142, 2144) that are operable to clamp and energize tissue that is captured between jaws (2142, 2144). Instrument (2110) further comprises a trigger (2116) that is in communication with a coupler (2118) and that is operable to move along handles (2112, 2114) with coupler (2118). As best seen in FIG. 37, coupler (2118) defines a channel (2124) and a coupling arm (2126). Handle (2114) is slidably disposed in channel (2124) such that coupler (2118) can slide along handle (2114). Coupling arm (2126) is coupled with trigger (2116) such that when a user presses trigger (2116), coupler (2118) slides along handle (2114). It will be appreciated that coupler (2118) and trigger (2116) may be biased to assume the position shown in FIG. 38A.

Handle (2114) of the present example comprises a pair of segments that are joined at a joint (2120) and that are operable to pivot relative to each other at joint (2120). Handle (2114) further comprises a pivoting link (2122) that is in pivotal communication with a translating knife (2170), such that link (2122) is operable to advance knife (2170) distally in response to handle (2114) pivoting toward handle (2112). FIG. 38B shows handle (2114) pivoted to a position where jaws (2142, 2144) are fully closed and are thereby positioned to clamp tissue. It should be noted that coupler (2118) is positioned over joint (2120) during the transition from FIG. 38A to FIG. 38B, and thereby prevents the segments of handle (2114) from pivoting at joint (2120). In other words, coupler (2118) keeps handle (2114) substantially straight during the transition from FIG. 38A to FIG. 38B.

After jaws (2142, 2144) have clamped on tissue, trigger (2116) may then be actuated distally, as seen in FIG. 38C, to apply bipolar RF energy to jaws (2142, 2144) to weld/seal/coagulate the tissue. The distally positioned trigger (2116) also locks jaws (2142, 2144) together in the closed position. When trigger (2116) is actuated distally, coupler (2118) is also slid distally along handle (2114), such that coupler (2118) no longer encompasses joint (2120). With coupler (2118) in a distal position and with joint (2120) being effectively freed, the user may then squeeze handles (2112, 2114) further toward each other, thereby pivoting the proximal segment of handle (2114) relative to the distal segment of handle (2112) at joint (2120). This further pivoting of the proximal segment of handle (2114) drives the distal end of link (2122) distally, which in turn drives knife (2170) distally to sever tissue captured between jaws (2142, 2144). Knife (2170) may have an I-beam configuration or any other suitable configuration. After tissue has been severed, the user may release handle (2114) and pull trigger (2116) back proximally, resetting instrument (2110) to the position shown in FIG. 38E.

Figures 39, 40A, 40B:
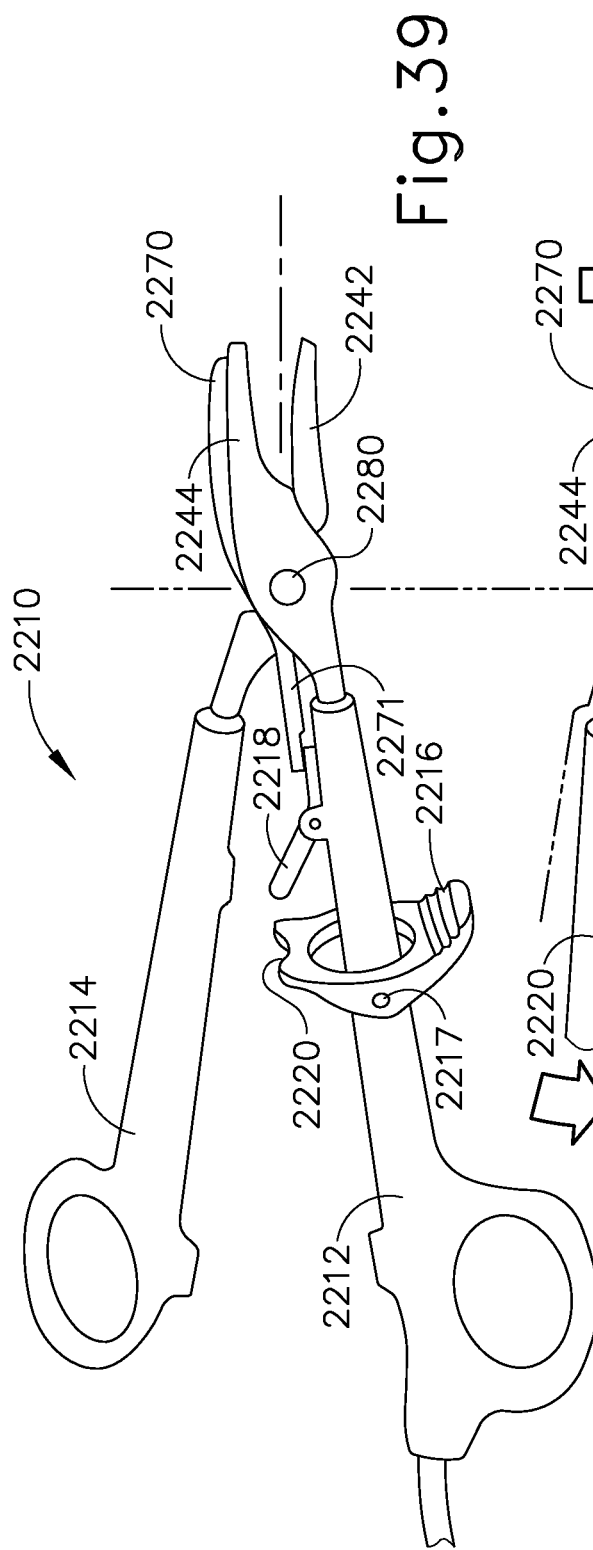
FIG. 39 depicts a side view of an exemplary alternative forceps instrument with a knife lock out trigger.
FIG. 40A depicts a partial side view of the forceps instrument of FIG. 39 with jaws closed.
FIG. 40B depicts a partial side view of the forceps instrument of FIG. 39 with the lockout trigger actuated.

The forceps instrument (2210) shown in FIGS. 39-40B combines features of forceps instrument (1810) of FIGS. 33A-33C with features of forceps instrument (1910) of FIGS. 34A-34C. In particular, instrument (2210) of this example includes handles (2212, 2214), jaws (2242, 2244), a pivoting trigger member (2216), and a pivoting knife (2270). Trigger member (2216) is pivotally coupled with handle (2212) by a pin (2217) and is operable to selectively restrict movement of jaws (2242, 2244) by selectively arresting movement of handle (2212) toward handle (2214). While not depicted in FIGS. 39-40B, it should be understood that trigger member (2216) may also include a feature similar to button (1820) described above, which may selectively activate electrode surfaces of jaws (2242, 2244) with RF energy as described above, to thereby weld/seal/coagulate tissue captured between jaws (2242, 2244).

An upper portion of trigger member (2216) includes a seat (2220) that is shaped to complement the underside of upper handle (2214). Trigger member (2216) is pivotable about pin (2217) through the range of motion depicted in FIGS. 40A-40B. In particular, when trigger member (2016) is in the generally upright position, trigger member (2216) enables handles (2212, 2214) to be partially pivoted toward each other as shown in the transition from FIG. 39 to FIG. 40A. This provides partial closure of jaws (2242, 2244). When handles (2212, 2214) and jaws (2242, 2244) reach the position shown in FIG. 40A, handle (2214) is received in seat (2220) and trigger member (2216) blocks further pivoting of handles (2212, 2214) and jaws (2242, 2244). The length of trigger member (2216) is selected to provide a particular gap between jaws (2242, 2244) at this stage. This gap is associated with a degree of tissue compression associated with tissue welding/sealing/coagulating. For instance, this gap may be similar to the distance between jaws (342, 344) shown in FIG. 10B. At this stage, the user may activate electrode surfaces of jaws (2242, 2244) with RF energy to thereby weld/seal/coagulate tissue captured between jaws (2242, 2244).

After the user has activated electrode surfaces of jaws (2242, 2244) with RF energy as described above, and the tissue between jaws has been sufficiently welded/sealed/coagulated, the user may press on trigger member (2216) to pivot trigger member (2216) from the position shown in FIG. 40A to the position shown in FIG. 40B. This moves seat (2220) out of engagement with upper handle (2214), providing clearance for handles (2212, 2214) to be drawn closer together, thereby enabling jaws (2242, 2244) to be driven further toward each other. This additional clearance also enables upper handle (2214) to actuate pivoting knife (2270) as will be described in greater detail below.

Knife (2270) of the present example comprises a blade that is configured to pass through a longitudinally extending slot formed in upper jaw (2244), such that knife (2270) is pivotable from an upper position (FIG. 40A) to a lower position (FIG. 40B). Knife (2270) is pivotally coupled at the same joint (2280) that couples jaws (2242, 2244) and handles (2212, 2214) in this example, though it should be understood that a separate coupling may be used. The proximal end of knife (2270) presents a lever arm (2271) that is engaged by an actuation arm (2218), which is pivotally secured to lower handle (2212). Actuation arm (2218) is bent at an obtuse angle in this example, with a distal portion contacting the underside of lever arm (2271). The proximal portion of actuation arm (2218) is positioned for engagement by a protrusion (2215) of upper handle (2214). In particular, as upper handle (2214) is pivoted from the position shown in FIG. 40A to the position shown in FIG. 40B, protrusion (2215) drives the proximal portion of actuation arm (2218) downwardly. This causes the distal portion of actuation arm (2218) to pivot upwardly, which in turn drives lever arm (2271) of knife (2270) upwardly. This upward movement of lever arm (2271) provides downward movement of the blade of knife (2270) as seen in the transition from FIG. 40A to FIG. 40B. This downward movement of the blade of knife (2270) severs tissue captured between jaws (2242, 2244). In some versions, lower jaw (2242) provides a cutting board against which the blade of knife (2270) acts in order to sever tissue captured between jaws (2242, 2244).

FIGS. 41-42C show yet another exemplary version of a forceps instrument (2310) operable to prevent inadvertent actuation of a knife (2370). Instrument (2310) of this example comprises handles (2312, 2314) and jaws (2342, 2344). Knife (2370) extends longitudinally through a shaft (2313) and is operable to advance distally to cut tissue clamped in between jaws (2342, 2344). The distal portion of knife (2370) has an I-beam configuration in this example, though it should be understood that any other suitable configuration may be used. Handle (2314) has a bent distal portion (2320) that is pivotally coupled with a link (2322), which is further pivotally coupled with the proximal end of knife (2370). Instrument (2310) further comprises a trigger (2316) that is operable to selectively prevent movement of handle (2314) toward handle (2312). In particular, and as best seen in FIG. 42A, a stem (2317) of trigger (2316) engages a notch (2318) formed in distal portion (2320) of handle (2314), such that trigger (2316) is operable to block movement of handle (2314).

As shown in FIG. 42B, trigger (2316) may be pivoted to disengage stem (2317) from notch (2318), to thereby release handle (2314). With handle (2314) released from trigger (2316), the user may pivot handle (2314) toward handle (2312), as also shown in FIG. 42B. This movement of handle (2312) drives knife (2370) distally via link (2322). Knife (2370) has upper and lower flanges (2371, 2373) that interact with jaws (2342, 2344) to drive upper jaw (2344) toward lower jaw (2342), such that jaws (2342, 2344) close in response to distal advancement of knife (2370). Jaws (2342, 2344) and knife (2370) may thus clamp and sever tissue as knife (2370) is driven distally. In some versions, jaws (2342, 2344) also include electrode surfaces that are operable to deliver bipolar RF energy to tissue clamped between jaws (2342, 2344), to thereby weld/seal/coagulate the tissue. By way of example only, an RF activation button may be incorporated into trigger (2316) and/or elsewhere within instrument (2310). After (2310) instrument has performed the desired operations on tissue, the user may release trigger (2316) to the original position shown in FIG. 41. This pulls knife (2370) back proximally, ultimately opening jaws (2342, 2344) back up as shown in FIG. 42C. If desired, the user may pivot trigger (2316) to re-engage stem (2317) in notch (2318), to thereby re-lock handle (2314) as shown in FIG. 42A.

FIGS. 43A-43D show another exemplary forceps instrument (2410) having jaws (2442, 2444) and handles (2412, 2414). A knife (2470) is operable to advance distally through handle (2412) to cut tissue clamped between jaws (2442, 2444). The distal portion of knife (2470) has an I-beam configuration in this example, though it should be understood that any other suitable configuration may be used. Knife (2470) is pivotally coupled with a link (2422), which is further pivotally coupled with handle (2414). A trigger (2416) is operable to selectively block distal movement of knife (2470). In particular, trigger (2416) is configured to selectively engage a lateral notch (2424) formed in knife (2470). When trigger (2416) engages notch (2424), knife (2470) is unable to move distally. When trigger (2416) is disengaged from notch (2424), knife (2470) is free to move distally.

Figure 43A:
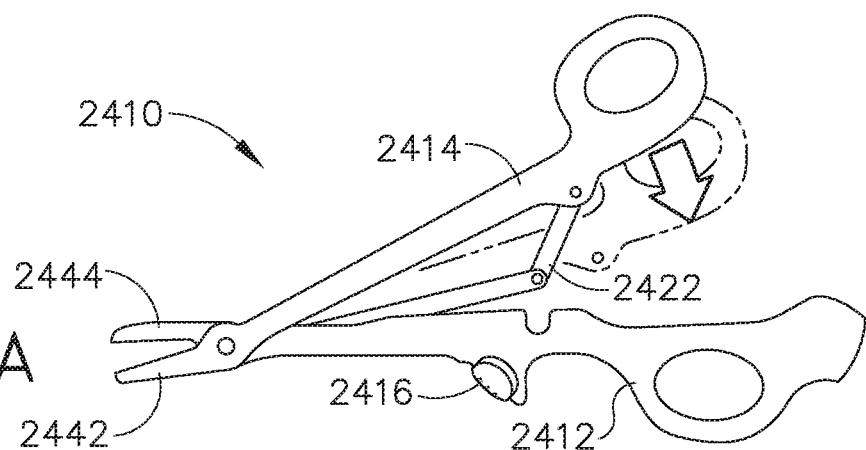
FIG. 43A depicts a side view of an exemplary alternative forceps instrument with a knife lockout trigger.
Figure 43B:
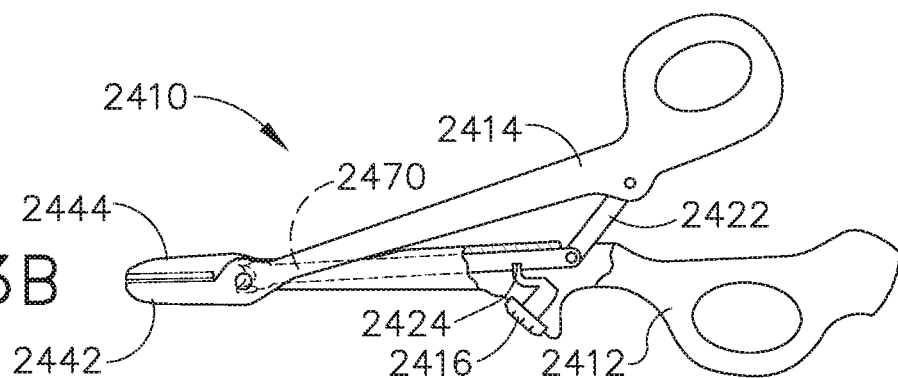
FIG. 43B depicts a side view of the forceps instrument of FIG. 43A with the jaws closed and the knife lockout trigger engaged.
Figure 43C:
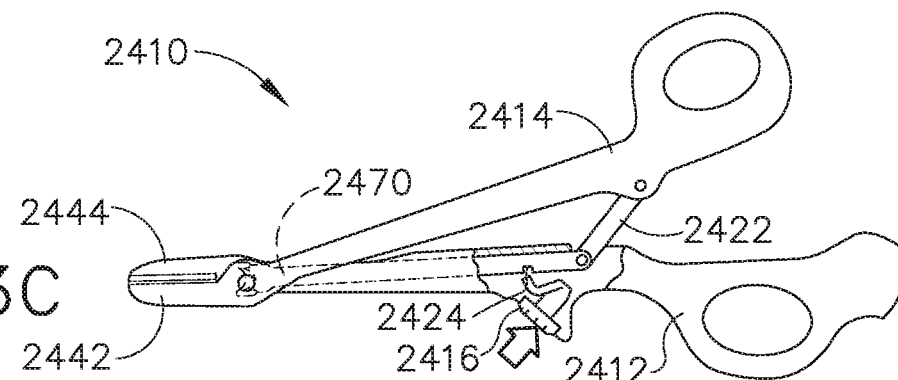
FIG. 43C depicts a side view of the forceps instrument of FIG. 43A with the knife lockout trigger pressed and disengaging the knife.
Figure 43D:
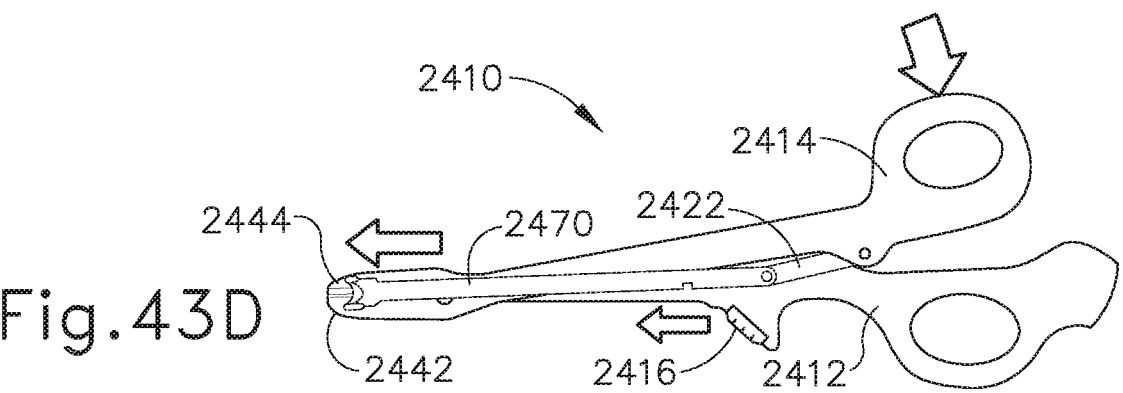
FIG. 43D depicts a side view of the forceps instrument of FIG. 43A with the knife advanced.

FIG. 43A shows jaws (2442, 2444) open. The user closes jaws (2442, 2444) by squeezing handles (2412, 2414) together as seen in FIG. 43B. As knife (2470) closes into handle (2412), trigger (2416) engages notch (2424) of knife (2470) such that knife (2470) cannot advance. Jaws (2442, 2444) clamp on tissue that might be positioned between jaws (2442, 2444). The user may then activate electrode surfaces that are operable to deliver bipolar RF energy to tissue clamped between jaws (2442, 2444), to thereby weld/seal/coagulate the tissue. By way of example only, an RF activation button may be incorporated into trigger (2416) and/or elsewhere within instrument (2410). Regardless of whether pulling trigger (2416) activates electrode surfaces, the user may pull trigger (2416) to disengage trigger (2416) from notch (2424) of knife (2470), as shown in FIG. 43C. With trigger (2416) disengaged from notch (2424), the user may complete the pivoting of handle (2414) toward handle (2412), thereby driving knife (2470) distally via link (2422), as shown in FIG. 43D. This distal advancement of knife (2470) severs tissue captured between jaws (2442, 2444).

Figure 44A:
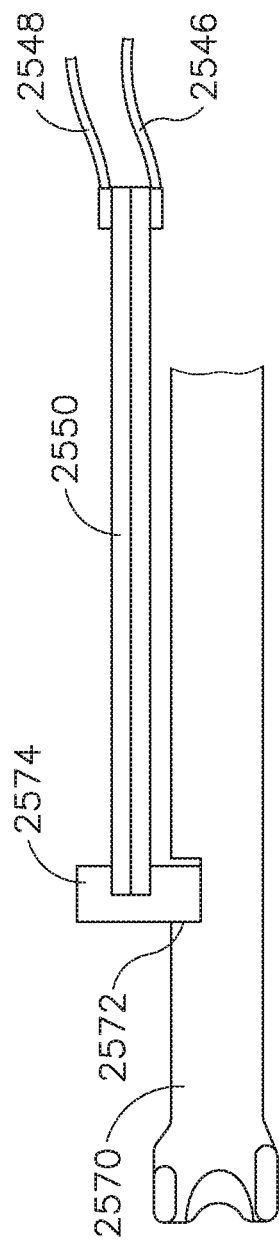
FIG. 44A depicts a side partial view of an exemplary alternative knife with an energy sensitive beam.
Figure 44B:
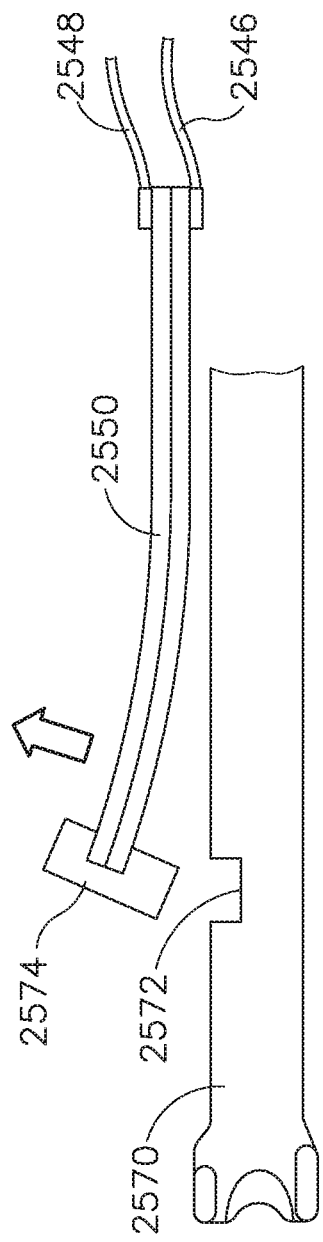
FIG. 44B depicts a side partial view of the knife shown in FIG. 44A with the lockout energized.

FIGS. 44A-44B show an alternative assembly that may be used to selectively prevent distal advancement of a knife. In particular, FIGS. 44A-44B show a knife (2570) having an I-beam distal end configuration and a lateral notch (2572). A pin (2574) is operable to selectively engage notch (2572), to thereby selectively prevent knife (2570) from being advanced distally. Pin (2574) is secured to the distal end of an electroactive laminate (2550), which is coupled with a pair of wires (2546, 2548).

In some versions, electroactive laminate (2550) comprises a layer of heat sensitive material that expands or contracts in response to heat, with the heat being generated when a current is communicated through wires (2546, 2548). In some other versions, electroactive laminate (2550) comprises a layer of electroactive polymer that expands or contracts in response to current being communicated through wires (2546, 2548). Other suitable materials and constructions for electroactive laminate (2550) will be apparent to those of ordinary skill in the art in view of the teachings herein. As can be seen in FIG. 44B, passing current through wires (2546, 2548) causes electroactive laminate (2550) to bend, driving pin (2574) out of engagement with notch (2572), thereby freeing knife (2570) to translate distally. It should be understood that this configuration (and variations thereof) may be used in any of the examples described herein with movable knives. It should also be understood that a logic circuit may be provided to prevent current from flowing through wires (2546, 2548) until electrodes have applied bipolar RF energy to tissue. By way of example only, the circuit may prevent current from flowing through wires (2546, 2548) until an impedance value associated with the tissue reaches a level indicating sufficient welding/sealing of the tissue by the RF energy. Other suitable variations will be apparent to those of ordinary skill in the art in view of the teachings herein.

Figure 45:
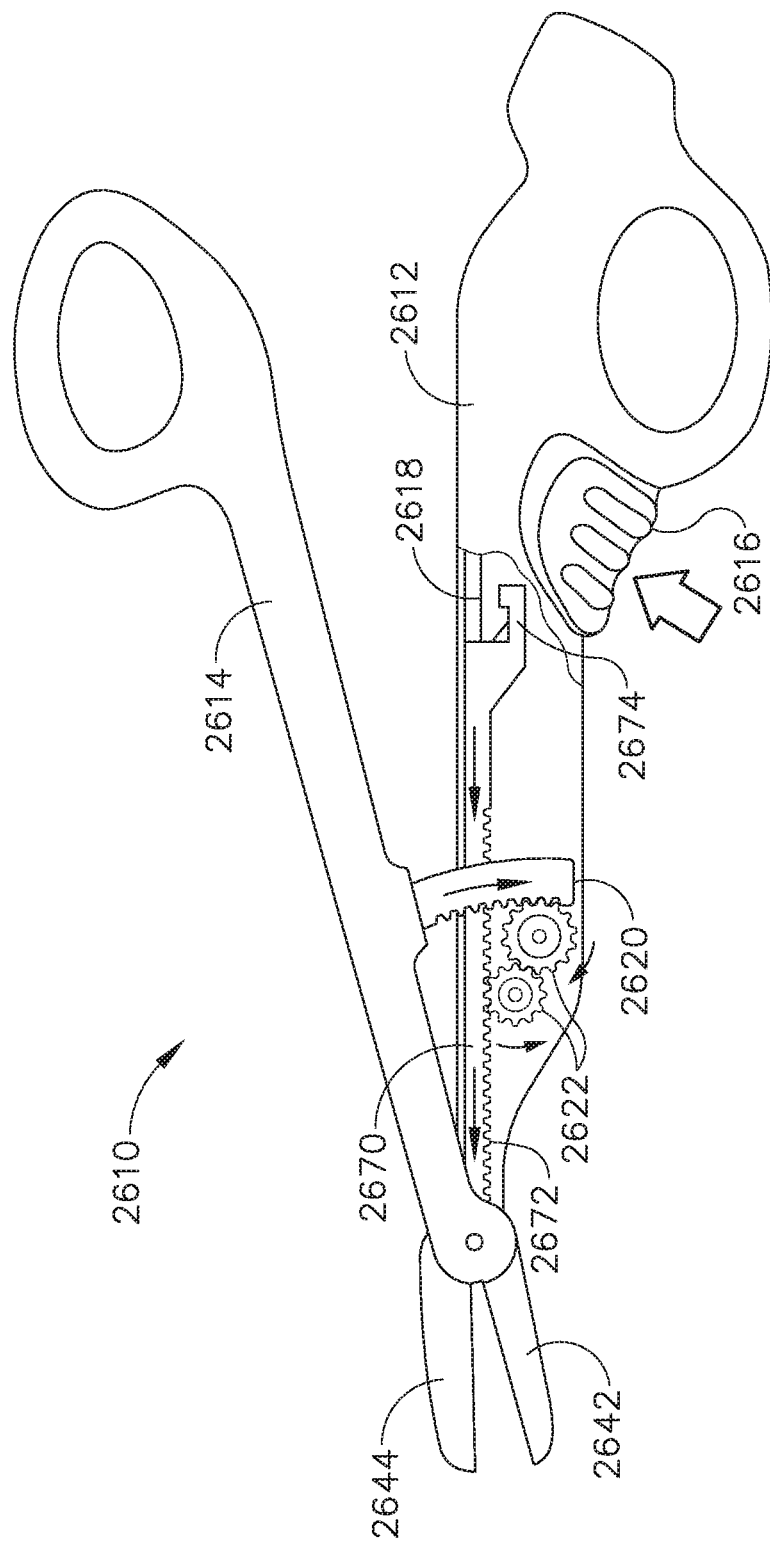
FIG. 45 depicts a side view of another exemplary alternative forceps instrument with a knife lockout feature.
Figure 46:
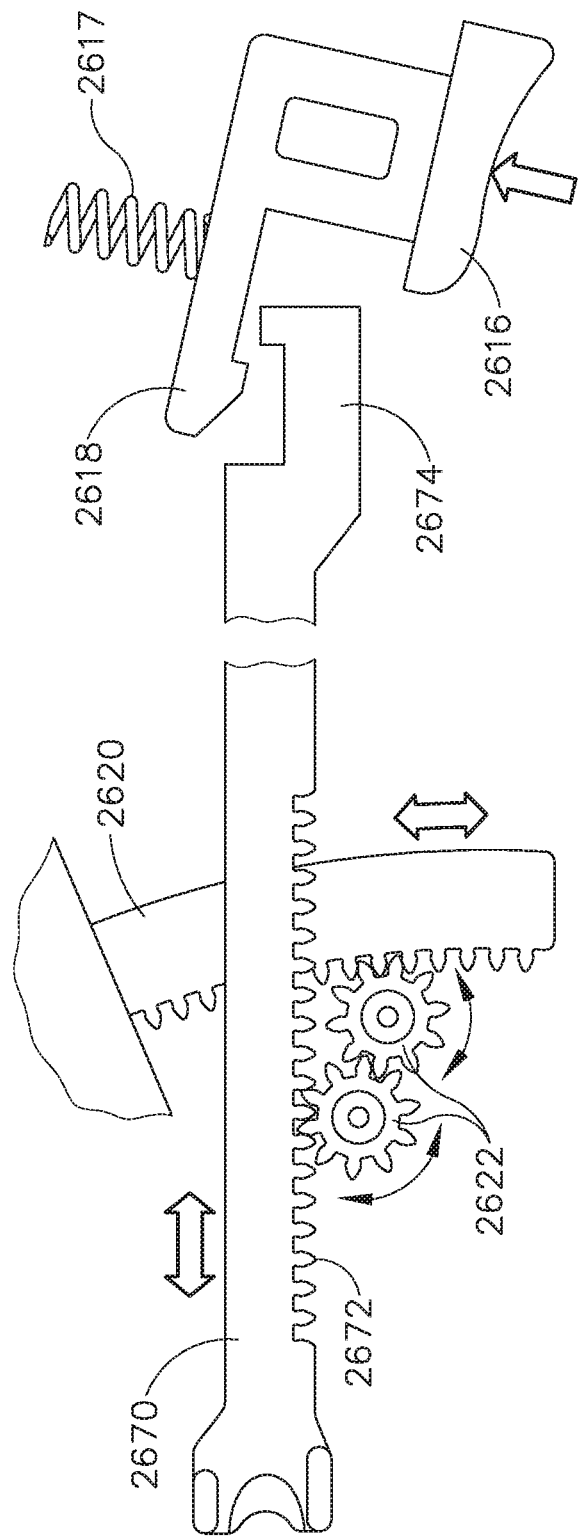
FIG. 46 depicts a side partial view of the knife lockout feature of FIG. 45 with the knife lockout trigger disengaged.

FIGS. 45-46 show yet another exemplary forceps instrument (2610) with jaws (2642, 2644) and handles (2612, 2614) and a mechanism for controlling the advancement of a knife (2670). Instrument (2610) comprises knife (2670) that is operable to advance within a handle (2612) and that has a distal end with an I-beam configuration. Handle (2614) comprises a rack (2620) engaged with a pair of pinions (2622), which are further engaged with rack teeth (2672) on knife (2670). When handle (2614) is squeezed downward toward handle (2612), rack (2620) moves downward to rotate pinions (2622) and thereby advance knife (2670) distally as seen in FIG. 46. However, the advancement of knife (2670) is selectively prevented using a spring biased trigger (2616) with a latch (2618) that is operable to engage a receiving latch (2674) at the proximal end of knife (2670). The positioning and configuration of latches (2618, 2674) prevents knife (2670) from advancing distally when latches (2618, 2674) are engaged. Latches (2618, 2674) may be disengaged by a user depressing trigger (2616), such that the user must hold trigger (2616) in a depressed position in order to advance knife (2670) distally. A spring (2617) biases latch (2618) into engagement with latch (2674). By way of example only, an RF activation button may be incorporated into trigger (2616) and/or elsewhere within instrument (2610), to provide activation of electrode surfaces that are operable to deliver bipolar RF energy to tissue clamped between jaws (2642, 2644), to thereby weld/seal/coagulate the tissue.

Figure 47A:
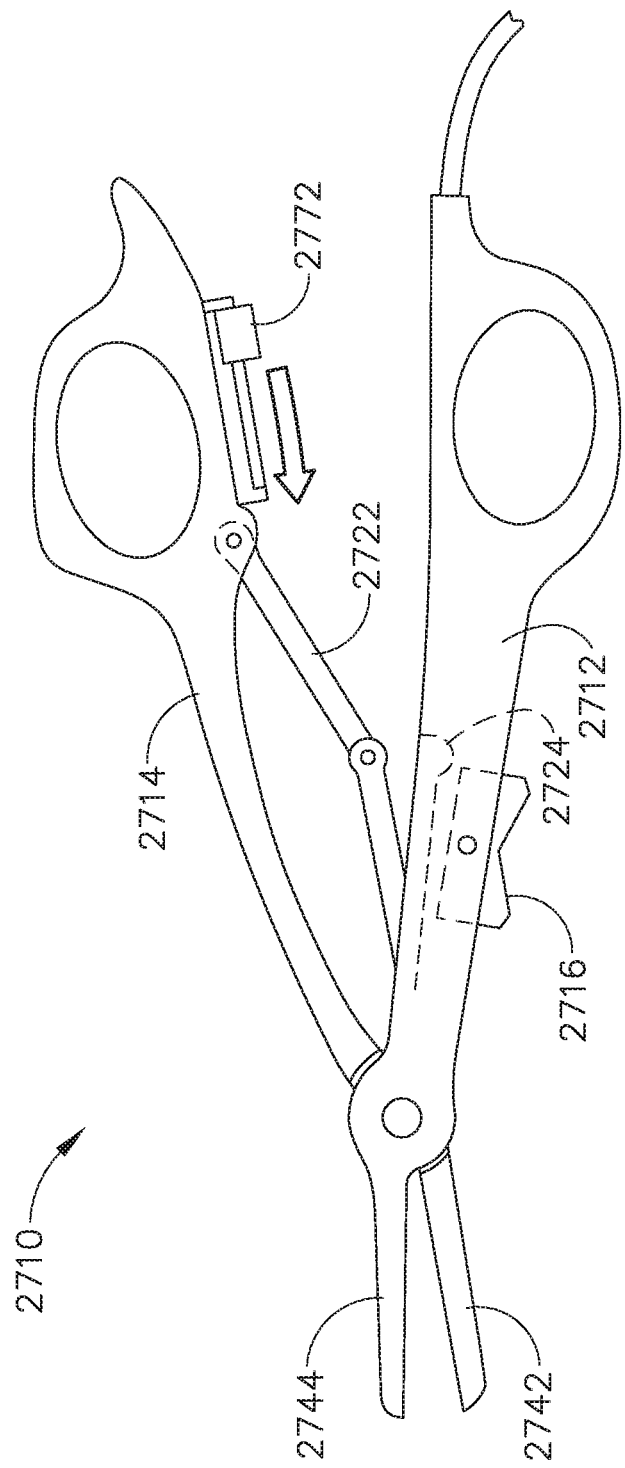
FIG. 47A depicts a side view of an exemplary alternative forceps instrument with a curved knife advancement rod.
Figure 47B:
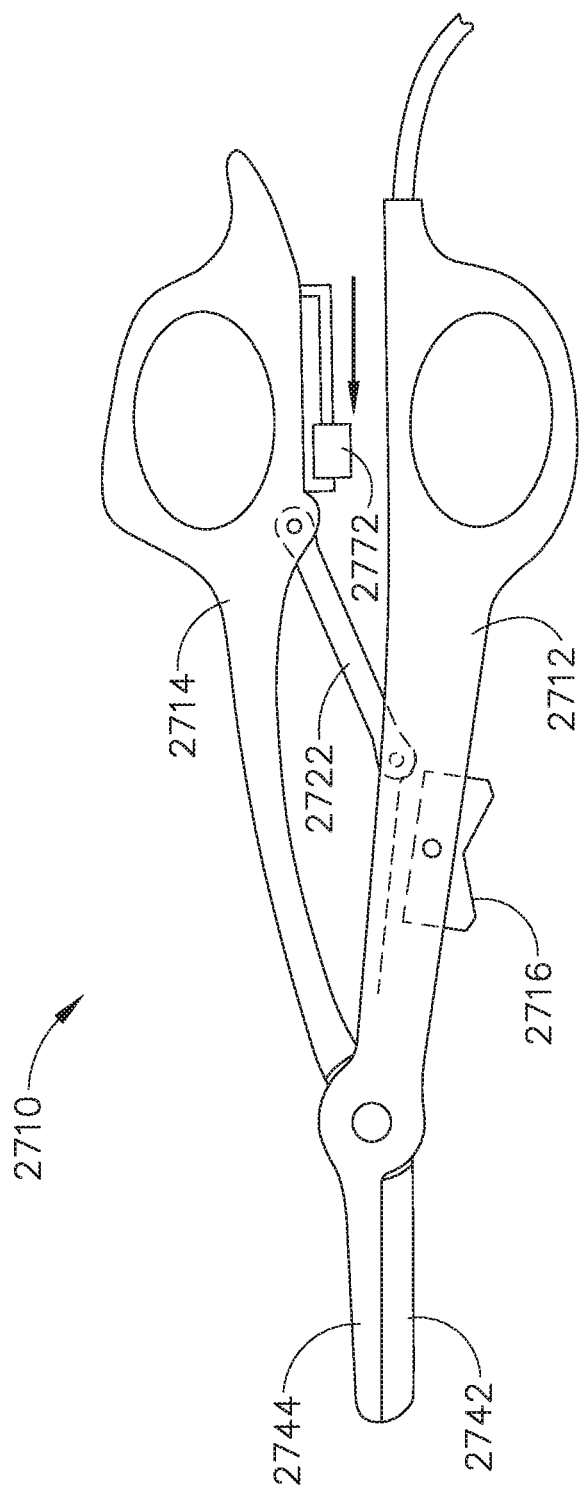
FIG. 47B depicts a side view of the forceps instrument of FIG. 47A with the curved knife advancement rod advanced.

FIGS. 47A-47B show yet another exemplary version of a forceps instrument (2710) with jaws (2742, 2744) and handles (2712, 2714) and a mechanism for controlling the advancement of a knife (not shown). In particular, handle (2714) is in communication with a link (2722) that is operable to engage a notch (2724) of handle (2712). Engagement between link (2722) and (2724) may provide added stability for the user to slide knife button (2772) as seen in FIG. 47B. While knife button (2772) is shown as a slider switch in the exemplary version, it will be appreciated that knife button (2772) may comprise any suitable switch as will be apparent to one of ordinary skill in the art in view of the teachings herein. Actuating knife button (2772) is operable to advance a curved blade through handle (2714) to cut tissue between jaws (2742, 2744). In some versions, handle (2714) is at least partially flexible to facilitate advancement of the knife. A trigger (2716) is operable to selectively activate exposed electrode surfaces in jaws (2742, 2744) to deliver bipolar RF energy to tissue clamped between jaws (2742, 2744), to thereby weld/seal/coagulate the tissue.

Figure 48:
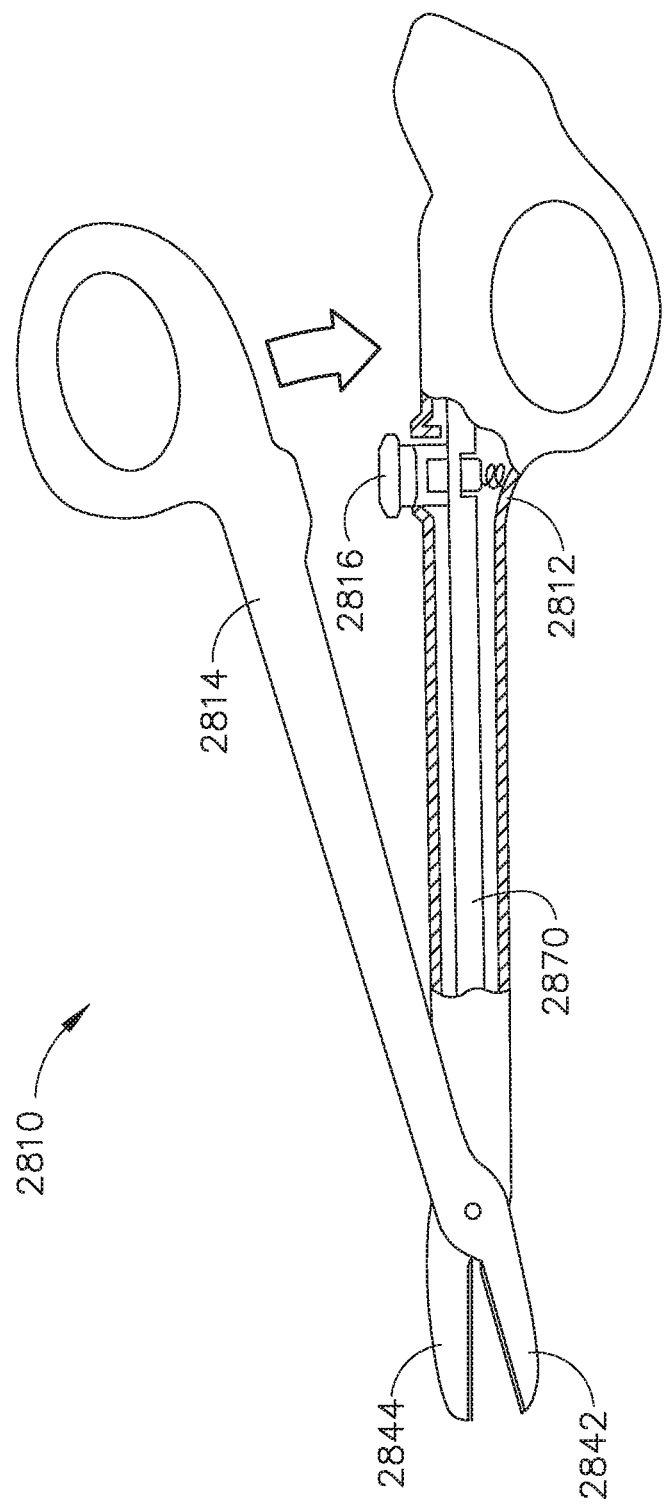
FIG. 48 depicts a side view of an exemplary alternative forceps instrument with a spring loaded knife lockout feature.
Figure 49A:
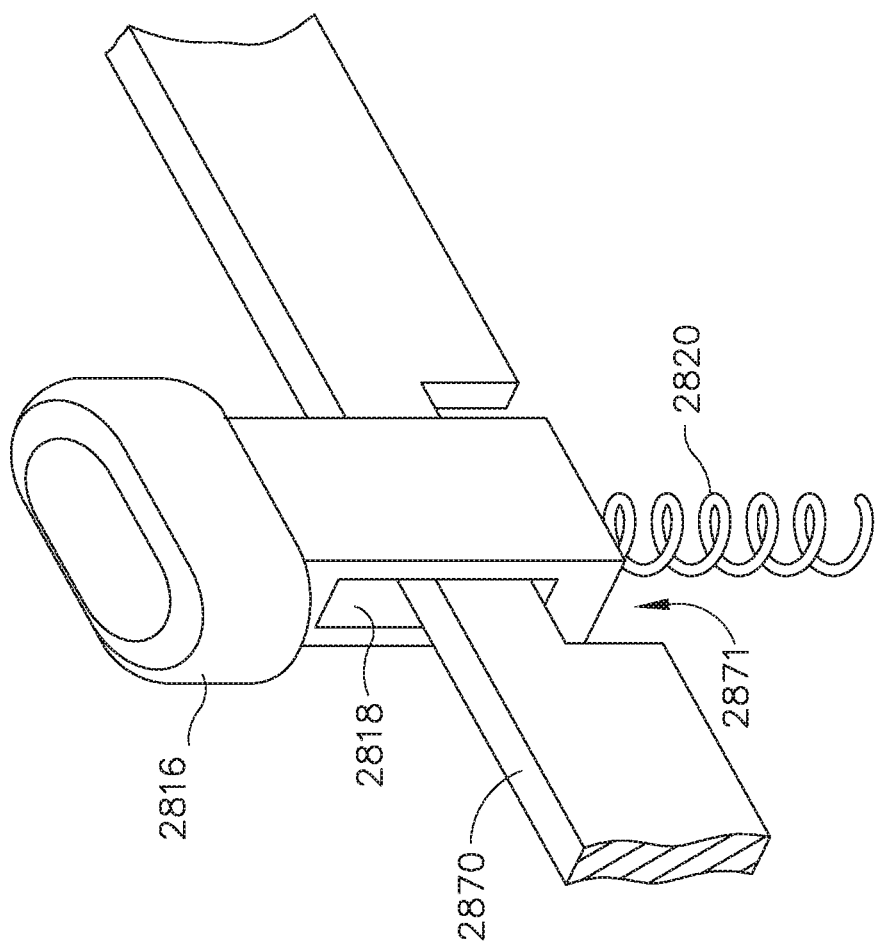
FIG. 49A depicts a perspective view of the spring loaded knife lockout feature of FIG. 48 engaging the knife.

FIG. 48 shows yet another exemplary version of a forceps instrument (2810) with jaws (2842, 2844) and handles (2812, 2814) and a mechanism for controlling the advancement of a knife (2870). Instrument (2810) includes a handle trigger (2816) that is actuated by closing handle (2814) against handle (2812). As seen in FIG. 49A, trigger (2816) forms a passageway (2818) for knife (2870) to pass through. A spring (2820) biases trigger (2816) to an upward position, as best seen in FIG. 49A. In this position, trigger (2816) is disposed in a lateral notch (2871) formed in knife (2870). This engagement prevents knife (2870) from moving longitudinally. When handle (2814) is closed against handle (2812) to close jaws (2842, 2844), handle (2814) eventually drives trigger (2816) downwardly, against the bias of spring (2820). As shown in FIG. 49B, this disengages trigger (2816) from lateral notch (2871) and enables knife (2870) to travel distally. In some versions, knife (2870) is resiliently biased distally such that knife (2870) will translate distally as soon as trigger (2816) is disengaged from lateral notch (2871). In some other versions, a separate actuator is used to drive knife (2870) distally. In addition to effectively unlocking knife (2870), trigger (2816) also closes an electrical switch when trigger (2816) is driven to the downward position shown in FIG. 49B. In particular, this completes an electrical circuit that activates exposed electrode surfaces in jaws (2842, 2844) to deliver bipolar RF energy to tissue clamped between jaws (2842, 2844), to thereby weld/seal/coagulate the tissue. Alternatively, a separate activation feature may be used to complete the circuit.

Figure 50:
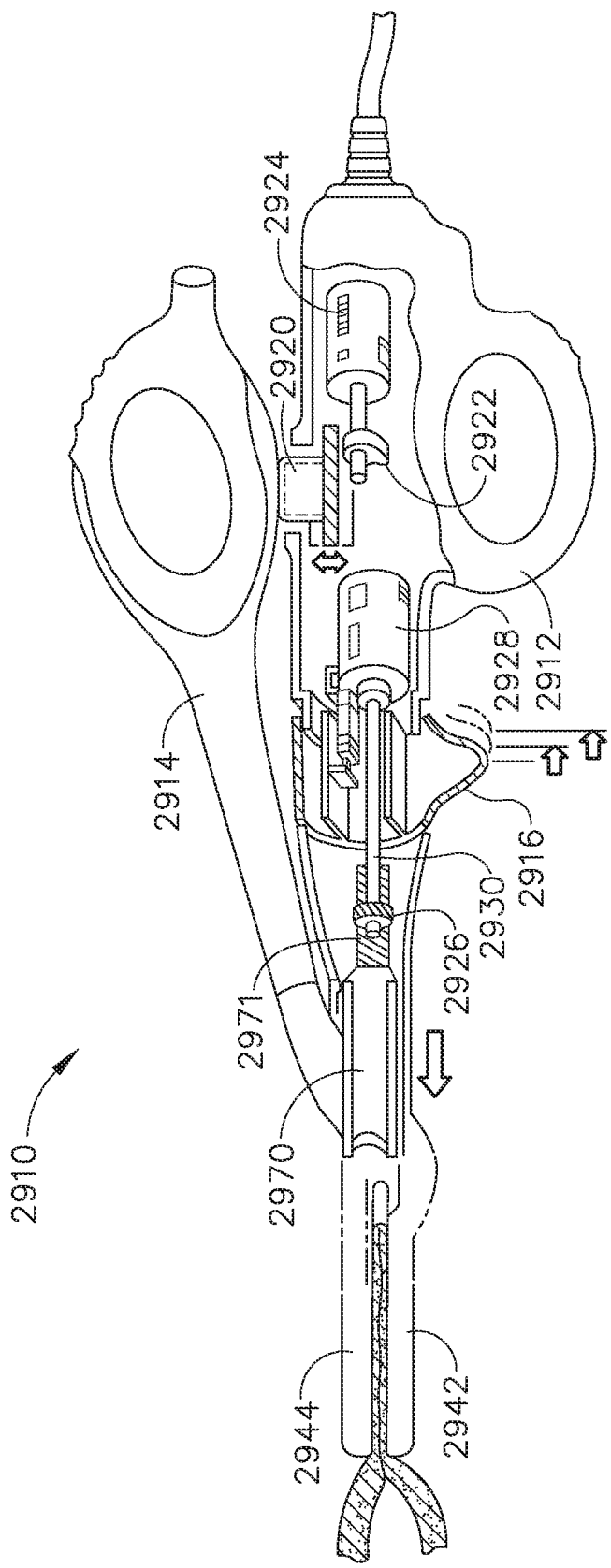
FIG. 50 depicts side cross sectional view of an exemplary alternative forceps instrument with a motor driven knife.

FIG. 50 shows yet another exemplary version of a forceps instrument (2910) with jaws (2942, 2944) and handles (2912, 2914) and a mechanism for controlling the advancement of a knife (2970). Knife (2970) has a distal end with an I-beam configuration and a proximal end with a drive feature (2971) that is engaged with a gear (2926). Gear (2926) is coupled with a drive shaft (2930) of a motor (2928). Thus, motor (2928) is operable to drive knife (2970) distally to sever tissue clamped between jaws (2942, 2944). Handle (2912) includes a trigger (2916) that is operable to both activate motor (2928) and activates exposed electrode surfaces in jaws (2942, 2944) to deliver bipolar RF energy to tissue clamped between jaws (2942, 2944), to thereby weld/seal/coagulate the tissue. In this example, trigger (2916) is configured to provide two-stage actuation, similar to trigger button (1616) described above, such that trigger (2916) is operable to activate the bipolar RF electrodes when trigger (2916) is actuated to a first position, and such that trigger (2916) is operable to activate motor (2928) when trigger (2916) is actuated to a second position. Of course, any other suitable user input feature(s) may be provided.

Handle (2912) also includes a stopper (2920) that is positioned to arrest pivoting of handle (2914) toward handle (2912). In particular, a rotary cam (2922) is positioned under stopper (2920) and is operable to either hold stopper (2920) in the upper position or allow stopper (2920) to travel downwardly, depending on the rotational position of cam (2922). A motor (2924) is operable to selectively rotate cam (2922). Motor (2924) is in communication with the same circuit as trigger (2916). A control logic is configured to activate motor (2924) in response to one or more conditions. In some versions, motor (2924) is activated when trigger (2916) is actuated to the second position. In addition or in the alternative, a control logic may activate motor (2924) only when an impedance value associated with the tissue reaches a level indicating sufficient welding/sealing of the tissue by the RF energy after trigger (2916) reaches the second position. Other suitable conditions for activating motor (2924) will be apparent to those of ordinary skill in the art in view of the teachings herein. It should be understood that, when stopper (2920) is in the upper position, jaws (2942, 2944) may only travel to a partially closed position due to the inability of handle (2914) to fully pivot toward handle (2912). Even in this partially closed position, jaws (2942, 2944) clamp down on tissue enough to weld/seal/coagulate the tissue. However, the merely partial closing of jaws (2942, 2944) will prevent knife (2970) from being able to translate distally through jaws (2942, 2944). In other words, jaws (2942, 2944) must be fully closed in order for knife (2970) to translate distally in this example, and full closure of jaws (2942, 2944) is only possible when stopper (2920) is in the downward position.

VIII. Exemplary Energy Control Features

In the examples described above, a trigger, button, or other type of user input feature is used to selectively activate exposed electrode surfaces in jaws to deliver bipolar RF energy to tissue clamped between the jaws, to thereby weld/seal/coagulate the tissue. In some instances, these user input features may be actuated before the jaws are sufficiently closed on tissue. It may therefore be desirable in some instances to provide a circuit feature that requires the jaws to be closed to a certain degree before the RF energy may be delivered to the electrode surfaces in the jaws. Several examples of such features will be described in greater detail below, while additional examples will be apparent to those of ordinary skill in the art in view of the teachings herein. It should be understood that the below features may be used in addition to or in lieu of a trigger, button, or other type of user input feature. In other words, the below features may be used to provide automatic activation of electrodes upon sufficient closure of jaws (e.g., such that a trigger, button, or other user input feature is omitted); or to provide a circuit lockout or safety switch that renders a trigger, button, or other type of user input feature inoperable until the jaws are sufficiently closed. Various suitable ways in which the below teachings may be incorporated into the numerous instruments described above will be apparent to those of ordinary skill in the art in view of the teachings herein.

Figure 51A:
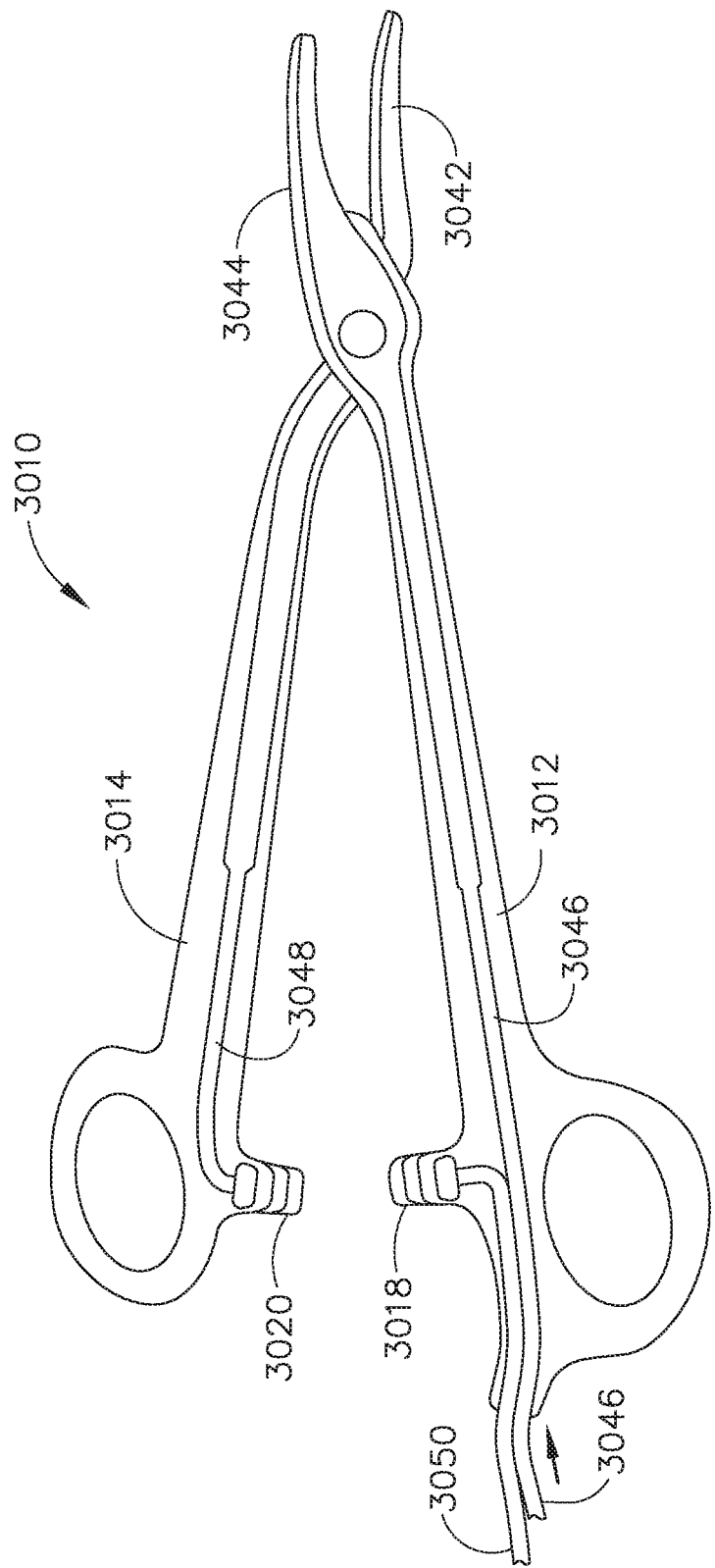
FIG. 51A depicts a side view of an exemplary alternative forceps instrument with ratcheting pads.
Figure 51B:
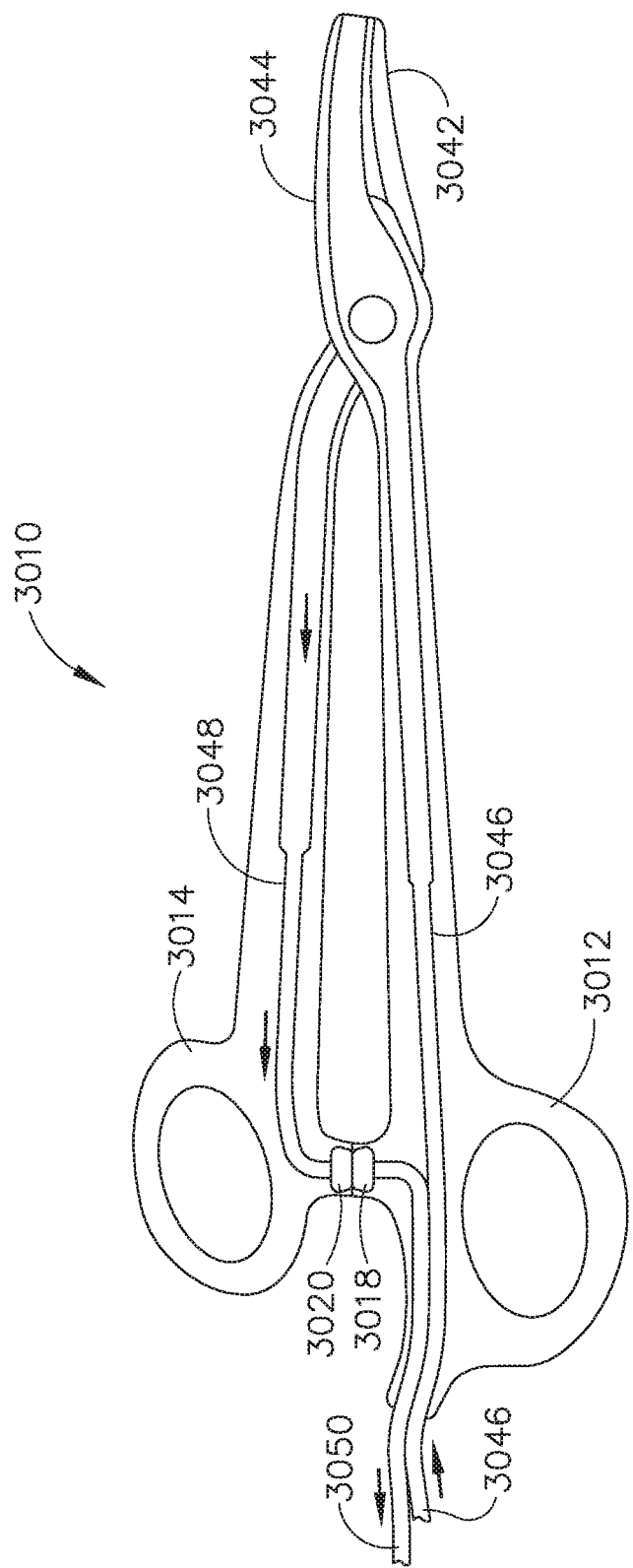
FIG. 51B depicts a side view of the forceps instrument of FIG. 51A with the ratcheting pads closed.

FIG. 51A shows an exemplary version of a forceps instrument (3010) with jaws (3042, 3044) and handles (3012, 3014) and a mechanism for controlling the flow of electricity through instrument (3010). A first wire (3046) is in communication with one or more electrode surfaces in jaw (3044); while a second wire (3048) is in electrical communication with one or more electrode surfaces in jaw (3042). A third wire (3050) and first wire (3046) are in communication with a power source (not shown). Third wire (3050) is also in communication with a first ratcheting contact pad (3018) of handle (3012); while second wire (3048) is in communication with a second ratcheting contact pad (3020) of handle (3014). First pad (3018) and second pad (3020) are configured to ratchet together as handles (3012, 3014) are pivoted toward each other to close jaws (3042, 3044). When pads (3018, 3020) are coupled together, pads (3018, 3020) complete an electrical path between second wire (3048) and third wire (3050), thereby coupling second wire (3048) with the power source. With first and second wires (3046, 3048) being coupled with the power source, the power source is operable to deliver bipolar RF energy to wires (3046, 3048), to thereby weld/seal/coagulate tissue clamped between jaws (3042, 3044).

Figure 52:
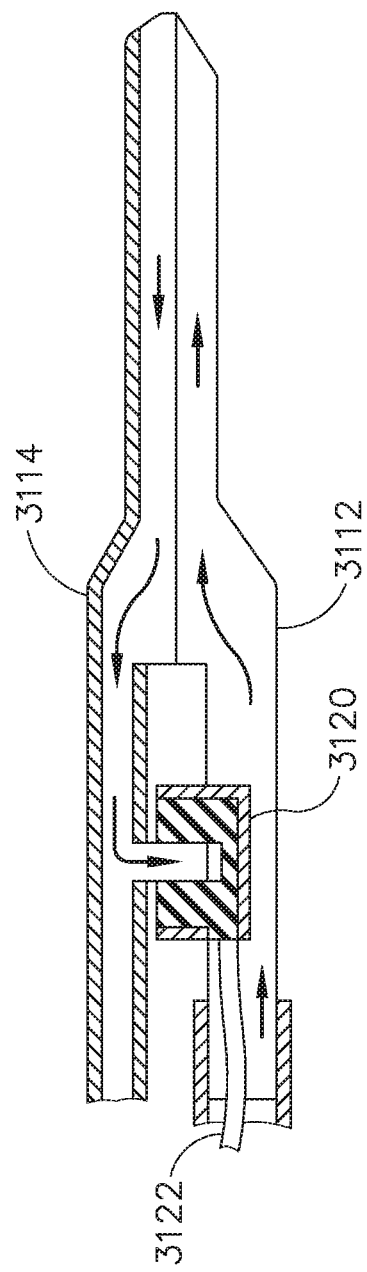
FIG. 52 depicts an enlarged side cross sectional view of the closure triggered energizing feature using a slip ring.

FIG. 52 shows yet another exemplary version of a portion of handles (3112, 3114) having a slip ring (3120) to prevent the flow of energy unless handles (3112, 3114) are closed. In particular, insulated wire (3122) is broken at slip ring (3120) until handle (3114) closes into slip ring (3120). It will be appreciated that either of handles (3112, 3114) may house the active wire while the other may house the return wire.

Figure 53A:
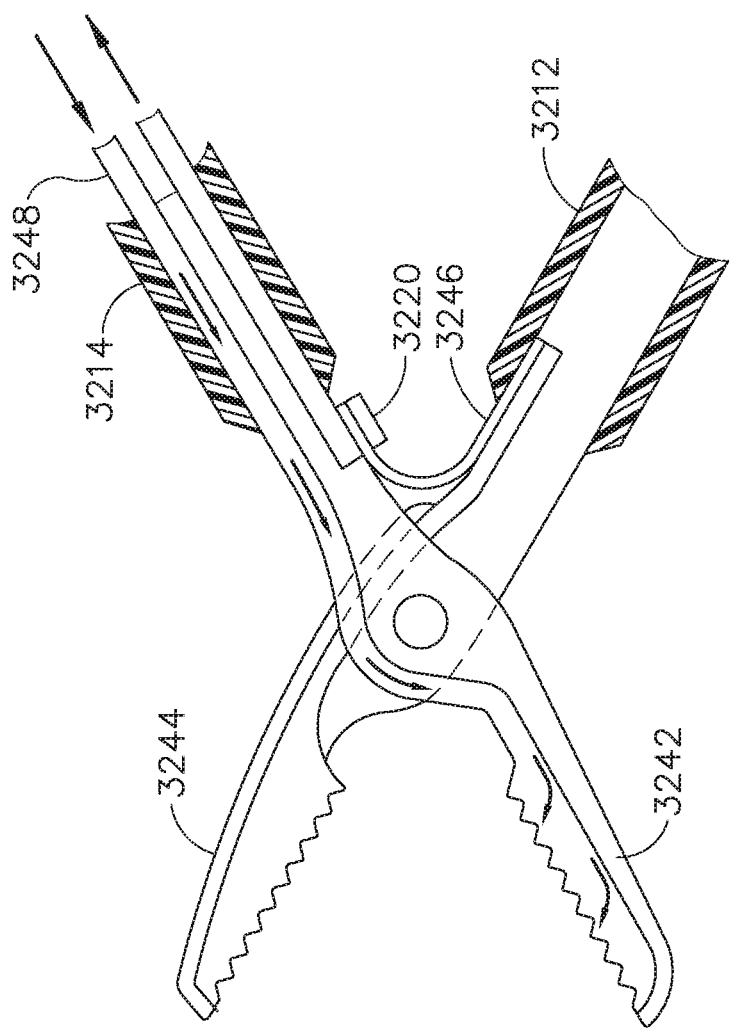
FIG. 53A depicts a side view of an exemplary alternative forceps instrument with a closure triggered energizing feature located near the jaws of the forceps instrument.
Figure 53B:
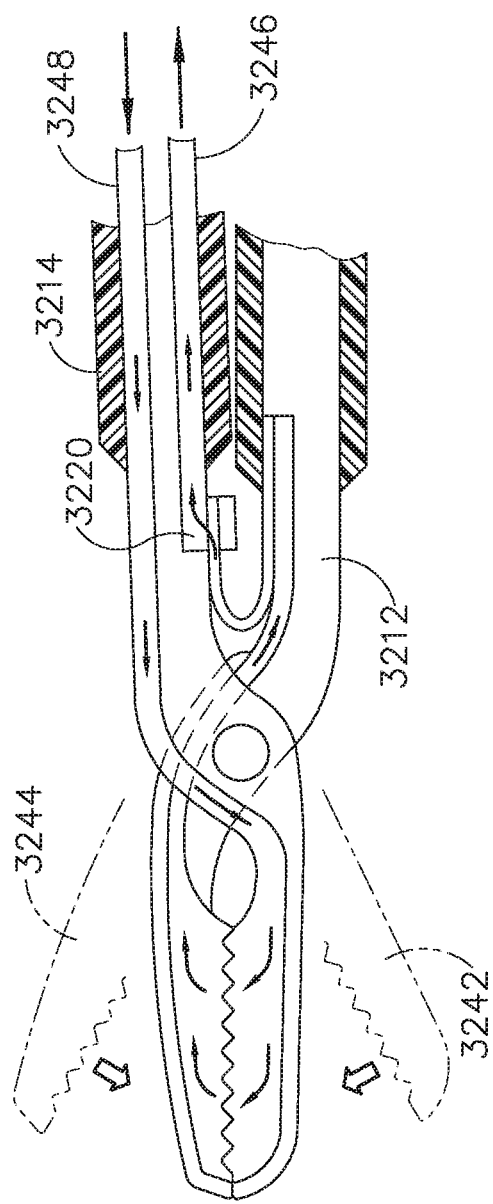
FIG. 53B depicts a side view of the forceps instrument of FIG. 53A with the jaws closed and the closure triggered energizing feature engaged.

FIGS. 53A-53B show yet another version of jaws (3242, 3244) with a portion of handles (3212, 3214). Wires (3246, 3248) are in communication with a power source and are thereby operable to deliver bipolar RF energy to jaws (3242, 3244). A spring contact (3220) is operable to selectively provide electrical communication to jaw (3244) by opening wire (3246) when in the position shown in FIG. 53A. As handles (3212, 3214) and jaws (3242, 3244) close, spring contact (3220) also closes, allowing energy to be delivered to jaw (3244) as shown in FIG. 53B. It will be appreciated that other suitable ways of regulating the flow of electricity to jaws (3242, 3244) may be used as would be apparent to one of ordinary skill in the art in view of the teachings herein.

IX. Miscellaneous

It should be understood that any of the versions of instrument (10) described herein may include various other features in addition to or in lieu of those described above. By way of example only, any of the devices herein may also include one or more of the various features disclosed in any of the various references that are incorporated by reference herein. In addition or in the alternative, any of the devices herein may also include one or more of the various features disclosed in U.S. Provisional Application Ser. No. 61/641,443, entitled "Electrosurgical Device for Cutting and Coagulating," filed May 2, 2012, the disclosure of which is incorporated by reference herein. Various suitable ways in which such teachings may be combined will be apparent to those of ordinary skill in the art in view of the teachings herein.

It should also be understood that any of the devices described herein may be modified to include a motor or other electrically powered device to drive an otherwise manually moved component. Various examples of such modifications are described in U.S. Pub. No. 2012/0116379, entitled "Motor Driven Electrosurgical Device with Mechanical and Electrical Feedback," published May 10, 2012, now U.S. Pat. No. 9,161,803, issued on Oct. 20, 2015, the disclosure of which is incorporated by reference herein. Various other suitable ways in which a motor or other electrically powered device may be incorporated into any of the devices herein will be apparent to those of ordinary skill in the art in view of the teachings herein.

It should also be understood that any of the devices described herein may be modified to contain most, if not all, of the required components within the medical device itself. More specifically, the devices described herein may be adapted to use an internal or attachable power source instead of requiring the device to be plugged into an external power source by a cable. Various examples of how medical devices may be adapted to include a portable power source are disclosed in U.S. Provisional Application Ser. No. 61/410,603, filed Nov. 5, 2010, entitled "Energy-Based Surgical Instruments," the disclosure of which is incorporated by reference herein. Various other suitable ways in which a power source may be incorporated into any of the devices herein will be apparent to those of ordinary skill in the art in view of the teachings herein.

While the examples herein are described mainly in the context of electrosurgical instruments, it should be understood that various teachings herein may be readily applied to a variety of other types of devices. By way of example only, the various teachings herein may be readily applied to other types of electrosurgical instruments, tissue graspers, tissue retrieval pouch deploying instruments, surgical staplers, surgical clip appliers, ultrasonic surgical instruments, etc. It should also be understood that the teachings herein may be readily applied to any of the instruments described in any of the references cited herein, such that the teachings herein may be readily combined with the teachings of any of the references cited herein in numerous ways. Other types of instruments into which the teachings herein may be incorporated will be apparent to those of ordinary skill in the art.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
   (a) a body; and
   (b) an end effector positioned distal to the body, wherein the end effector comprises:
      (i) a first jaw having a first grasping surface, the first grasping surface comprising a first electrode surface and a downwardly facing protrusion, wherein the downwardly facing protrusion comprises a first PTC thermistor material, and
      (ii) a second jaw having a second grasping surface, the second grasping surface comprising a second electrode surface and an upwardly facing protrusion laterally offset from the downwardly facing protrusion of the first grasping surface, wherein the upwardly facing protrusion comprises a second PTC thermistor material,
   wherein the first jaw and the second jaw are configured to transition between an open position, a first closed position, a second closed position, and a third closed position,
   wherein the first jaw and the second jaw are closer together in the second closed position as compared to the first closed position,
   wherein the first jaw and the second jaw are closer together in the third closed position as compared to the second closed position,
   wherein the first jaw and the second jaw are operable to grasp tissue in the first closed position,
   wherein the first electrode surface and the second electrode surface are operable to transmit bipolar RF energy to tissue grasped between the first jaw and the second jaw in the second closed position,
   wherein the downwardly facing protrusion and the upwardly facing protrusion are configured to cooperatively sever tissue captured between the first jaw and the second jaw in the third closed position,
   wherein at least one of the downwardly facing protrusion or the upwardly facing protrusion is configured to contact only a portion of the second electrode surface or the first electrode surface, respectively, in the third closed position,
   wherein the first PTC thermistor material is configured to contact the portion of the second electrode surface in the third closed position, wherein the second PTC thermistor material is configured to contact the portion of the first electrode surface in the third closed position,
   wherein the first PTC thermistor material and the second PTC thermistor material define a lateral gap in the third closed position,
   wherein the first electrode surface and the second electrode surface extend along the lateral gap in the third closed position.

2. The apparatus of claim 1, wherein the upwardly facing protrusion comprises a hump.

3. The apparatus of claim 1, wherein the upwardly facing protrusion comprises a ridge.

4. The apparatus of claim 3, wherein the ridge comprises a rounded profile.

5. The apparatus of claim 3, wherein the ridge comprises a square profile.

6. The apparatus of claim 3, wherein the ridge comprises a triangular profile.

7. The apparatus of claim 1, wherein the body comprises a first handle and a second handle, wherein the first and second handles are pivotally coupled together, wherein the first and second handles are operable to drive the first and second jaws to transition between the open position, the first closed position, the second closed position, and the third closed position.

8. The apparatus of claim 1, wherein the upwardly facing protrusion is in direct contact with the first grasping surface in the third closed position, wherein the upwardly facing protrusion is not in direct contact with the first grasping surface in the second closed position.

9. The apparatus of claim 1, wherein the first electrode surface extends laterally away from the downwardly presented protrusion toward the upwardly presented protrusion.

10. The apparatus of claim 9, wherein the second electrode surface extends laterally away from the upwardly presented protrusion toward the downwardly presented protrusion.

11. The apparatus of claim 10, wherein the first electrode surface and the second electrode surface are operable to transmit bipolar RF energy to tissue in the third closed position.

12. The apparatus of claim 1, further comprising an activation button configured to activate the first electrode surface and the second electrode surface to provide bipolar RF energy.

13. The apparatus of claim 1, wherein the downwardly facing protrusion comprises an insert configured to be coupled with a remaining portion of the first jaw.

14. The apparatus of claim 1, wherein the upwardly facing protrusion comprises an insert configured to be coupled with a remaining portion of the second jaw.

15. The apparatus of claim 1, wherein the upwardly facing protrusion and the downwardly facing protrusion each comprise electrically insulative material.

16. An apparatus comprising:
   (a) a body; and
   (b) an end effector positioned distal to the body, wherein the end effector comprises:
      (i) a first jaw comprising a first electrode surface configured to apply bipolar RF energy to tissue and a downwardly facing protrusion, wherein the downwardly facing protrusion comprises a first PTC thermistor material, and (ii) a second jaw comprising a second electrode surface configured to apply bipolar RF energy to tissue and an upwardly facing protrusion comprising a second PTC thermistor material, wherein the upwardly facing protrusion is laterally offset from the downwardly facing protrusion of the first jaw to define a lateral gap, wherein the first electrode surface and the second electrode surface laterally extend along the lateral gap, wherein the first and second jaws are configured to transition between an open position, a first closed position, a second closed position, and third closed position, wherein the first jaw and the second jaw are operable to grasp tissue in the first closed position, wherein the first electrode surface and the second electrode surface are operable to transmit bipolar RF energy to tissue grasped between the first jaw and the second jaw in the second closed position, wherein the downwardly facing protrusion and the upwardly facing protrusion are configured to cooperatively sever tissue captured between the first jaw and the second jaw in the third closed position, and wherein the first PTC thermistor material is configured to contact a portion of the second electrode surface and the second PTC thermistor material is configured to contact a portion of the first electrode surface in the third closed position to define the lateral gap.

17. The apparatus of claim 16, wherein the downwardly facing protrusion is configured to abut against the second jaw in the third closed position.

18. The apparatus of claim 16, wherein the upwardly facing protrusion is configured to abut against the first jaw in the third closed position.

19. An apparatus comprising:
(a) a body; and
(b) an end effector positioned distal to the body, wherein the end effector comprises:
  (i) a first jaw comprising a first electrode surface configured to apply bipolar RF energy to tissue and a downwardly facing protrusion, wherein the downwardly facing protrusion comprises a first PTC thermistor material, and
  (ii) a second jaw comprising a second electrode surface configured to apply bipolar RF energy to tissue and an upwardly facing protrusion, wherein the upwardly facing protrusion comprises a second PTC thermistor material, wherein the upwardly facing protrusion is laterally offset from the downwardly facing protrusion of the first jaw, wherein the first and second jaws are configured to transition between an open position, a first closed position, a second closed position, and third closed position, wherein the first jaw and the second jaw are operable to grasp tissue in the first closed position, wherein the first electrode surface and the second electrode surface are operable to transmit bipolar RF energy to tissue grasped between the first jaw and the second jaw in the second closed position, wherein the downwardly facing protrusion and the upwardly facing protrusion are configured to cooperatively sever tissue captured between the first jaw and the second jaw in the third closed position, wherein the first PTC thermistor material of the downwardly facing protrusion is configured to contact a portion of the second electrode surface in the third closed position, and wherein the second PTC thermistor material of the upwardly facing protrusion is configured to contact a portion of the first electrode surface in the third closed position, wherein the first PTC thermistor material and the second PTC thermistor material define a lateral gap in the third closed position, wherein the first electrode surface and the second electrode surface extend along the lateral gap in the third closed position.

* * * * *